(12) United States Patent
Tsuboi et al.

(10) Patent No.: US 9,227,962 B2
(45) Date of Patent: Jan. 5, 2016

(54) HETEROCYCLIC SUBSTITUTED-3-HETEROARYLIDENYL-2-INDOLINONE DERIVATIVE

(71) Applicant: Dainippon Sumitomo Pharma Co., Ltd., Osaka (JP)

(72) Inventors: Katsunori Tsuboi, Osaka (JP); Yosuke Takanashi, Osaka (JP); Shingo Tojo, Osaka (JP); Tomohiro Kodama, Osaka (JP); Katsumi Kubota, Osaka (JP); Toshio Kanai, Osaka (JP)

(73) Assignee: Boston Biomedical, Inc., Cambridge, MA (US)

( * ) Notice: Subject to any disclaimer, the term of this patent is extended or adjusted under 35 U.S.C. 154(b) by 0 days.

(21) Appl. No.: 14/208,289

(22) Filed: Mar. 13, 2014

(65) Prior Publication Data
US 2014/0275076 A1  Sep. 18, 2014

Related U.S. Application Data

(60) Provisional application No. 61/780,263, filed on Mar. 13, 2013.

(51) Int. Cl.
C07D 403/14 (2006.01)
C07D 417/14 (2006.01)
C07D 409/14 (2006.01)

(52) U.S. Cl.
CPC ............ C07D 417/14 (2013.01); C07D 403/14 (2013.01); C07D 409/14 (2013.01)

(58) Field of Classification Search
CPC .................................................... C07D 403/14
USPC ........................................................ 548/466
See application file for complete search history.

(56) References Cited

U.S. PATENT DOCUMENTS 7,026,330 B2   4/2006   Grupp et al.
7,176,234 B2   2/2007   Cai et al.
7,342,016 B2   3/2008   Zhu et al.
2006/0094674 A1   5/2006   Neel et al.
2014/0275033 A1   9/2014   Li et al.

FOREIGN PATENT DOCUMENTS

WO   2004/000300 A1   12/2003
WO   2009/033033 A2   3/2009

OTHER PUBLICATIONS

Li, et al. Document No. 150:306636, retrieved from STN; Mar. 12, 2009.*
Guan et al., Bioorganic & Medicinal Chemistry Letters (2004), 14(1), 187-190.

* cited by examiner

*Primary Examiner* — Shawquia Jackson
(74) *Attorney, Agent, or Firm* — Arent Fox LLP; Yi Liu; Tony K. Uhm

(57) ABSTRACT

Disclosed is a compound represented by formula (1) or a pharmacologically acceptable salt thereof. (In the formula, $R_1$ is optionally substituted heteroaryl etc.; $R_2$ is hydrogen etc.; $R_3$ and $R_4$ are each independently hydrogen etc., $R_5$ is the following group: (wherein Y is optionally substituted five membered heteroaryl etc., $R_{9a}$ is optionally substituted aryl etc., $R_{9b}$ and $R_{9c}$ are each dependently hydrogen etc., and m is the integral 0 etc.) etc.; $R_6$ is hydrogen etc.; and $R_7$ is hydrogen etc.

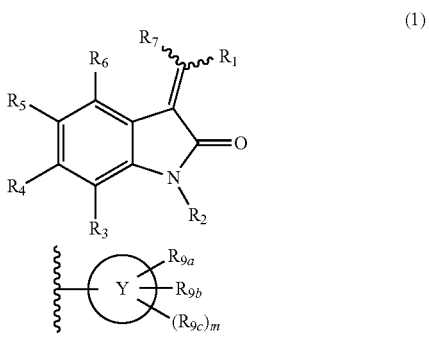

(1)

18 Claims, No Drawings

HETEROCYCLIC SUBSTITUTED-3-HETEROARYLIDENYL-2-INDOLINONE DERIVATIVE

RELATED APPLICATIONS

The present application claims the benefit of U.S. Provisional Application No. 61/780,263, filed Mar. 13, 2013. The contents of this application are hereby incorporated by reference in their entirety.

TECHNICAL FIELD

The present invention relates to novel heterocyclic substituted-3-heteroarylidenyl-2-indolinone derivative, or a pharmaceutically acceptable salts thereof which modulate the activity of protein kinases ("PKs"). The present invention also relates to pharmaceutical composition comprising heterocyclic substituted-3-heteroarylidenyl-2-indolinone derivative, or a pharmaceutically acceptable salts thereof. The present invention also relates to a therapeutic or preventive agent or method for treating disorders related to abnormal PK activity.

BACKGROUND ART

The protein kinases represent a large family of proteins, which plays a central role of in the regulation of wide variety of cellular processes and maintaining control over cellular function as enzymes that catalyze the phosphorylation of hydroxyl groups on tyrosine, serine and threonine residues of protein. A partial, non-limiting, list of these kinases include: receptor tyrosine kinases such as platelet-derived growth factor receptor kinase (PDGFR), insulin-like growth factor receptor (IGFR), the nerve growth factor receptor, TrkB, Met, and the fibroblast growth factor receptor, FGFR-3; non-receptor tyrosine kinase such as Abl and the function kinase Bcr-Abl, Lck, Csk, Fes, Bmx, and Src; and serine/threonint kinases such as B-Raf, C-Raf, Sgk, MAP kinases (e.g., MKK4, MKK6, etc.) and SAPK2a, SAPK2b and SAPK3. The consequences of phosphorylation with PKs are staggering; cell growth, differentiation and proliferation. Furthermore, aberrant kinase activity has been observed in many disease states including benign and malignant proliferative disorders, as well as diseases resulting from inappropriate activation of the immune and nerve systems. In view of the apparent link between PK-related cellular activities and wide variety of human disorders, a great deal of effort is being expended in an attempt to identify ways to modulate PK activity.

Some of this effort has involved biomimetic approaches using large molecules patterned on those involved in the actual cellular processes (mutant ligands (Patent Document 1); soluble receptors and antibodies (Patent Document 2) and tyrosine kinase inhibitors (Patent Document 3.).

In addition to the above, attempts have been made to identify small molecules which act as PK inhibitors, For example, bis-monocyclic, bicyclic and heterocyclic aryl compounds (Patent Document 4), vinylene azaindole derivatives (Patent Document 5) have been described as tyrosine kinase inhibitors. However these compounds have limited utility because of toxicity, poor bioavailability, or less potency.

On the other hand, some of indolinone derivatives are reported as PK inhibitors (Patent Document 6). Especially, 4-phenyl- or 4-pyridyl indolinone derivatives (Patent Document 7), and 5-(thiazol-4-yl)indolin-2-one derivatives (Patent Document 8) are reported.

However these prior arts do not disclose derivatives with other five-membered heteroaryl groups or heteroalicyclic group at $5^{th}$, $6^{th}$, or $7^{th}$ position on indolinone and indolin.
[Patent Document 1] U.S. Pat. No. 4,966,849
[Patent Document 2] WO94/10202 pamphlet
[Patent Document 3] WO92/21660 pamphlet
[Patent Document 4] WO92/20642 pamphlet
[Patent Document 5] WO94/14808 pamphlet
[Patent Document 6] U.S. Pat. No. 5,792,783
[Patent Document 7] WO02/02551 pamphlet
[Patent Document 8] WO2009/033033 pamphlet

SUMMARY OF INVENTION

Problems to be Solved by the Invention

Recently, a pharmaceutically satisfiable compound inhibiting CSCPKs has been desired as an agent for treating diseases including cancer etc.

According to the extensive studies for solving the problem, the inventors have found the following heterocyclic substituted-3-heteroarylidenyl-2-indolinone derivatives structurally characterized by specific group substituted the five-membered heteroaryl groups or heteroalicyclic group at $5^{th}$, $6^{th}$, or $7^{th}$ position on indolinone have potent CSCPKs inhibitory activity.

The inventors have also found that the derivatives have suitable properties essential for a medicament, including solubility, membrane permeability, metabolic stability, bioavailability, safety for heart (such as hERG), as well as CSCPKs inhibitory activity, and achieved the present invention.

Means of Solving the Problems

Specifically, the present invention is as follows.
Item1. A compound of formula 1:

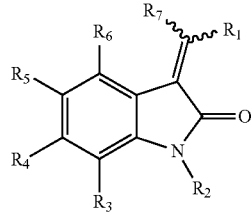

(1)

or pharmaceutically acceptable salt thereof,
$R_1$ is optionally substituted heteroaryl, or optionally substituted heteroalicyclic;
$R_2$ is hydrogen, optionally substituted alkyl, optionally substituted alkylcarbonyl, optionally substituted alkoxycarbonyl, or optionally substituted aminocarbonyl;
$R_3$ and $R_4$ are each independently hydrogen, halogen, cyano, nitro, hydroxy, optionally substituted alkyl, optionally substituted alkoxy, optionally substituted amino, optionally substituted alkoxycarbonyl, optionally substituted alkyl carbonyl, optionally substituted aminocarbonyl, or the following group:

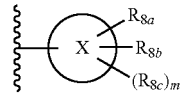

(wherein
X is optionally substituted five membered heteroaryl or optionally substituted heteroalicyclic,
$R_{8a}$ is optionally substituted aryl, optionally substituted heteroaryl, or optionally substituted heteroalicyclic,
$R_{8b}$ and $R_{8c}$ are each independently hydrogen, alkyl, halogen, cyano, amino, nitro, hydroxy, trifluoromethyl, optionally substituted aryl, optionally substituted heteroaryl, or optionally substituted heteroalicyclic, and
n is the integral 0 to 2),
$R_5$ is hydrogen, halogen, cyano, nitro, hydroxy, optionally substituted alkyl, optionally substituted alkoxy, optionally substituted amino, optionally substituted alkoxycarbonyl, optionally substituted alkylcarbonyl, optionally substituted aminocarbonyl, or the following group:

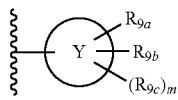

(wherein
Y is optionally substituted five membered heteroaryl(provided that the five membered heteroaryl is not the following group:

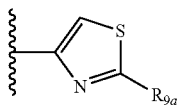

wherein $R_{9a}$ is same as the above definition),
$R_{9a}$ is optionally substituted aryl, optionally substituted heteroaryl, or optionally substituted heteroalicyclic,
$R_{9b}$ and $R_{9c}$ are each dependently hydrogen, alkyl, halogen, cyano, amino, nitro, hydroxy, trifluoromethyl, and
m is the integral 0 to 2), and
at least one of $R_3$, $R_4$ and $R_5$ is the following group:

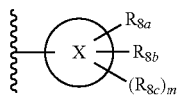

(X, $R_{8a}$, $R_{8b}$, $R_{8c}$ and n are same as the above definition), or the following group:

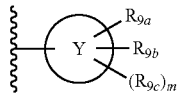

(Y, $R_{9a}$, $R_{9b}$, $R_{9c}$ and m are same as the above definition);
$R_6$ is hydrogen, halogen, cyano, nitro, hydroxy, amino, optionally substituted alkyl, optionally substituted alkoxy, optionally substituted amino, optionally substituted alkoxy carbonyl, optionally substituted alkyl carbonyl, or optionally substituted aminocarbonyl; and
$R_7$ is hydrogen, optionally substituted alkyl, or optionally substituted cycloalkyl.

Item2. The compound according to Item 1, or pharmaceutically acceptable salt thereof,
$R_1$ is optionally substituted heteroaryl, or optionally substituted heteroalicyclic,
wherein the heteroaryl is selected from the group consisting of pyrrole, furan, thiophene, pyridine, pyrimidine, pyrazine, pyridazine, indole, and pyrrolopyridinone, and heteroalicyclic is selected from the group consisting of pyridone, pyrrolidine, and piperidine.

Item3. The compound according to Item 2, or pharmaceutically acceptable salt thereof,
$R_1$ is optionally substituted heteroaryl, or optionally substituted heteroalicyclic,
wherein heteroaryl is pyrrole, or pyrrolopyridinone, and heteroalicyclic is pyridone.

Item4. The compound according to anyone of Items 1-3, or pharmaceutically acceptable salt thereof,
the substituent of optionally substituted heteroaryl and optionally substituted heteroalicyclic in $R_1$ is one or more substituent(s) selected from the group consisting of halogen, alkyl, optionally substituted alkoxy, optionally substituted amino, optionally substituted alkoxy carbonyl, optionally substituted alkylcarbonyl, or optionally substituted aminocarbonyl.

Item5. The compound according to anyone of Items 1-4, or pharmaceutically acceptable salt thereof,
$R_1$ is one of the group selected from the following group:

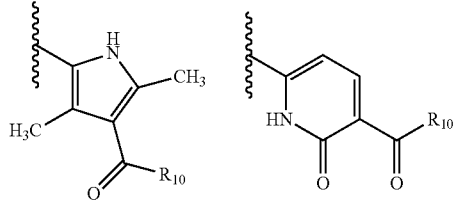

(wherein $R_{10}$ is hydroxyl, optionally substituted alkyl, optionally substituted alkoxy, or optionally substituted amino).

Item6. The compound according to Item 5, or pharmaceutically acceptable salt thereof,
$R_{10}$ is hydroxy, mono-substituted alkyl amino (said alkyl is substituted by di-substituted alkyl amino, or heteroalicyclic), piperazynyl, homopiperazynyl, or morphorinyl . . . .

Item7. The compound according to Item 6, or pharmaceutically acceptable salt thereof,
$R_{10}$ is hydroxy, ethyl amino (said ethyl is substituted by di-ethyl amino, 1-pyrrolidino), or 4-piperazinyl (said piperazinyl is substituted with alkyl).

Item8. The compound according to Item 7, or pharmaceutically acceptable salt thereof,
$R_{10}$ is hydroxy, 2-(di-ethyl amino)ethyl amino, 2-pyrrolidino ethyl amino, 4-methyl piperazinyl, or morpholino.

Item9. The compound according to anyone of Items 1-8, or pharmaceutically acceptable salt thereof,
$R_2$ is hydrogen, or optionally substituted alkoxy carbonyl.

Item10. The compound according to Item 9, or pharmaceutically acceptable salt thereof,
$R_2$ is hydrogen.

Item11. The compound according to anyone of Items 1-10, or pharmaceutically salt thereof,
$R_3$ and $R_4$ are each independently
  1: hydrogen,
  2: halgen,
  3: cyano,
  4: nitoro,
  5: hydroxy,
  6: alkyl.
  7: alkoxy,
  8: amino,
  9: alkylcarbonyl,
  10: alkoxycarbonyl,
  11: aminocarbonyl, and 12: the following group:

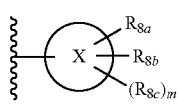

(wherein X, $R_{8a}$, $R_{8b}$, $R_{8c}$, and n are same as the above definition), wherein said alkyl, alkoxy, amino, alkylcarbonyl, alkoxycarbonyl, and aminocarbonyl are optionally substituted with one or more substitutent(s) selected from the group consisting of
- (a) alkyl,
- (b) alkenyl,
- (c) alkynyl,
- (d) hydroxy,
- (e) amino,
- (f) nitro,
- (g) cyano,
- (h) halogen,
- (i) alkoxy,
- (j) alkylcarbonyl,
- (k) alkoxycarbonyl,
- (l) aminocarbonyl,
- (m) aryl,
- (n) heteroaryl,
- (o) cycloalkyl, and
- (p) heteroalicyclic).

Item12. The compound according to Item 11, or pharmaceutically acceptable salt thereof,
$R_3$ and $R_4$ are each independently
1: hydrogen,
2: halogen,
3: alkyl(said alkyl is optionally substituted with one or more substituent(s) selected from the group consisting of
- (a) alkyl,
- (b) alkenyl,
- (c) alkynyl,
- (d) hydroxy,
- (e) amino,
- (f) nitro,
- (g) cyano,
- (h) halogen,
- (i) alkoxy,
- (j) alkylcarbonyl,
- (k) alkoxycarbonyl,
- (l) aminocarbonyl,
- (m) aryl,
- (n) heteroaryl,
- (o) cycloalkyl, and
- (p) heteroalicyclic)
4: the following group:

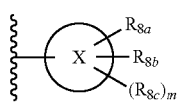

(wherein X, $R_{8a}$, $R_{8b}$, $R_{8c}$, and n are same as the above definition).

Item13. The compound according to Item 12, or pharmaceutically acceptable salt thereof,
$R_3$ and $R_4$ are each independently hydrogen, or the following group:

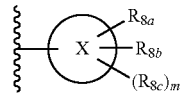

(wherein X, $R_{8a}$, $R_{8b}$, $R_{8c}$, and n are same as the above definition).

Item14. The compound according to anyone of Items 1-13, or pharmaceutically acceptable salt thereof,
X is pyrrole, furan, thiophene, imidazole, pyrazole, oxazole, isoxazole, thiazole, isothiazole, triazole, thiadiazole, oxadiazole, pyrrolidine, piperidine, azepane, tetrahydrofuran, oxane, or oxepane.

Item15. The compound according to Item 14, or pharmaceutically acceptable salt thereof,
X is pyrrole, furan, thiophene, imidazole, pyrazole, oxazole, isoxazole, thiazole, isothiazole, triazole, thiadiazole, or oxadiazole.

Item16. The compound according to Item 15, or pharmaceutically acceptable salt thereof,
X is thiophene, pyrazole, oxazole, thiazole, thiadiazole, or oxadiazole.

Item17. The compound according to Item 16, or pharmaceutically acceptable salt thereof,
X is pyrazole, thiazole, or oxazole.

Item18. The compound according to Item 14, or pharmaceutically acceptable salt thereof,
X is piperidine.

Item19. The compound according to anyone of Items 1-18, or pharmaceutically acceptable salt thereof,
$R_{8a}$, $R_{8b}$ and $R_{8c}$ are each independently hydrogen, alkyl, halogen, cyano, amino, nitro, hydroxy, trifluoromethyl, phenyl, or pyridyl.

Item20. The compound according to Item 19, or pharmaceutically acceptable salt thereof,
$R_{8a}$, $R_{8b}$ and $R_{8c}$ are each dependently hydrogen, alkyl, phenyl, or pyridyl.

Item21. The compound according to anyone of Items 1-20, or pharmaceutically acceptable salt thereof,
n is the integra 0.

Item22. The compound according to anyone of Items 1-10, or pharmaceutically acceptable salt thereof,
X is selected from the group consisting of the following group:

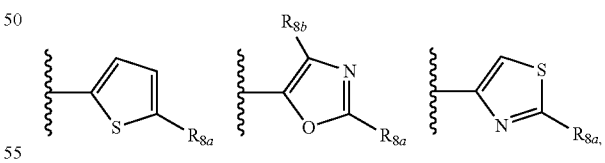

$R_{8a}$ is piperidinyl, pyranyl, phenyl, thiophenyl, pyrazinyl, pyrimidinyl, pyridazinyl, or pyridyl (said piperidinyl, pyranyl, phenyl, thiophenyl, pyrazinyl, pyrimidinyl, pyridazinyl, or pyridyl are optionally substituted with halogen, hydroxy, cyano, amino, nitro, alkyl, alkoxy, alkoxycarbonyl, alkylcarbonyl, or aminocarbonyl), and
$R_{8b}$ is alkyl.

Item23. The compound according to anyone of Items 1-10, or pharmaceutically acceptable salt thereof,
X is selected from the group consisting of the following group:

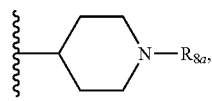

and $R_{8a}$ is 4-piperazinyl (said piperidinyl is substituted with alkyl or alkylcarbonyl), 4-tetrahydropyranyl, phenyl, pyrazinyl, pyrimidinyl, pyridazinyl, or pyridiyl (said phenyl, pyrazinyl, pyrimidinyl, pyridazinyl, or pyridyl are optionally substituted with halogen, hydroxy, cyano, amino, nitro, alkyl, alkoxy, alkoxycarbonyl, alkylcarbonyl, or aminocarbonyl).

Item24. The compound according to anyone of Items 1-10, or pharmaceutically acceptable salt thereof, $R_3$ and $R_4$ are hydrogen.

Item25. The compound according to anyone of Items 1-24, or pharmaceutically salt thereof, $R_5$ is
1: hydrogen,
2: halgen,
3: cyano,
4: nitoro,
5: hydroxy,
6: alkyl,
7: alkoxy,
8: amino,
9: alkylcarbonyl,
10: alkoxycarbonyl,
11: aminocarbonyl, and
12: the following group:

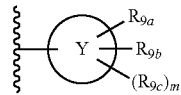

(wherein Y, $R_{9a}$, $R_{9b}$, $R_{9c}$, and m are same as the above definition), wherein said alkyl, alkoxy, amino, alkylcarbonyl, alkoxycarbonyl, and aminocarbonyl are optionally substituted with one or more substituent(s) selected from the group consisting of
(a) alkyl,
(b) alkenyl,
(c) alkynyl,
(d) hydroxy,
(e) amino,
(f) nitro,
(g) cyano,
(h) halogen,
(i) alkoxy,
(j) alkylcarbonyl,
(k) alkoxycarbonyl,
(l) aminocarbonyl,
(m) aryl,
(n) heteroaryl,
(o) cycloalkyl, and
(p) heteroalicyclic).

Item26. The compound according to Item 25, or pharmaceutically salt thereof, $R_5$ is hydrogen, or the following group:

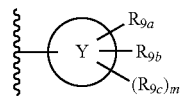

(wherein Y, $R_{9a}$, $R_{9b}$, $R_{9c}$, and m are same as the above definition).

Item27. The compound according to anyone of Items 1-26, or pharmaceutically acceptable salt thereof, Y is pyrrole, furan, thiophene, imidazole, pyrazole, oxazole, isoxazole, thiazole, isothiazole, triazole, thiadiazole, oxadiazole, pyrrolidine, piperidine, azepane, tetrahydrofuran, oxane, or oxepane.

Item28. The compound according to Item 27, or pharmaceutically acceptable salt thereof, Y is pyrrole, furan, thiophene, imidazole, pyrazole, oxazole, isoxazole, thiazole, isothiazole, triazole, thiadiazole, or oxadiazole.

Item29. The compound according to Item 28, or pharmaceutically acceptable salt thereof, Y is furan, thiophene, imidazole, pyrazole, oxazole, thiazole, triazole, thiadiazole, oxadiazole, Item30. The compound according to Item 27, or pharmaceutically acceptable salt thereof, Y is piperidine.

Item31. The compound according to anyone of Items 1-30, or pharmaceutically acceptable salt thereof, $R_{9a}$ is piperidinyl, pyranyl, phenyl, thiophenyl, or pyridyl (said pheny and pyridyl are optionally substituted with hydroxy, amino, nitro, cyano, alkyl, alkoxyl, trifluoromethyl, and halogen).

Item32. The compound according to anyone of Items 1-31, or pharmaceutically acceptable salt thereof, $R_{9b}$ and $R_{9c}$ are each dependently hydrogen, methyl, ethyl, halogen, cyano, amino, nitro, hydroxy, or trifluoromethyl.

Item33. The compound according to Item 32, or pharmaceutically acceptable salt thereof, $R_{9b}$ is each dependently hydrogen, methyl, ethyl, halogen, cyano, amino, nitro, hydroxy, or trifluoromethyl.

Item34. The compound according to anyone of Items 1-33, or pharmaceutically acceptable salt thereof, m is the integra 0.

Item35. The compound according to anyone of Items 1-24, or pharmaceutically acceptable salt thereof, $R_5$ is selected from the group consisting of the following group:

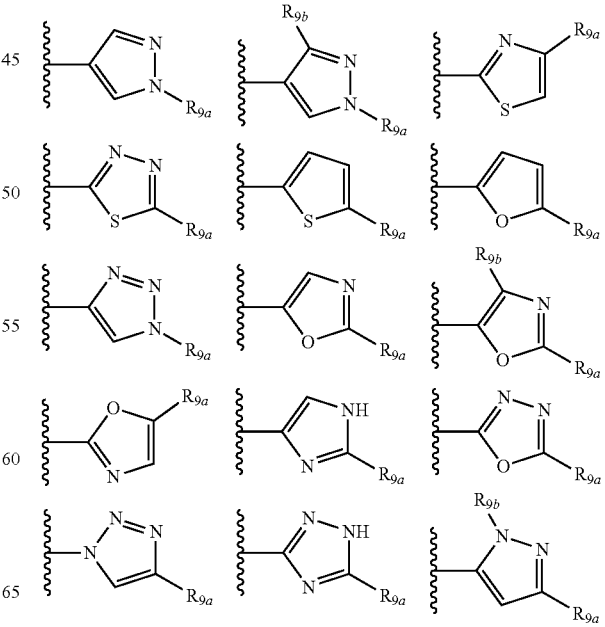

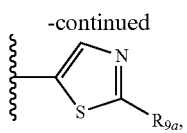

R$_{9a}$ is piperidinyl, pyranyl, phenyl, thiophenyl, pyrazinyl, pyrimidinyl, pyridazinyl, or pyridyl (said piperidinyl, pyranyl, phenyl, thiophenyl, pyrazinyl, pyrimidinyl, pyridazinyl, or pyridyl are optionally substituted with halogen, hydroxy, cyano, amino, nitro, alkyl, alkoxy, alkoxycarbonyl, alkylcarbonyl, or aminocarbonyl), and
R$_{9b}$ is alkyl.

Item36. The compound according to anyone of Items 1-24, or pharmaceutically acceptable salt thereof,
R$_5$ is selected from the group consisting of the following group:

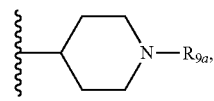

and
R$_{9a}$ is 4-piperazinyl (said piperidinyl is substituted with alkyl, or alkylcarbonyl), pyrazinyl, pyrimidinyl, pyridazinyl, or pyridiyl (said phenyl, pyrazinyl, pyrimidinyl, pyridazinyl, or pyridyl are optionally substituted with halogen, hydroxy, cyano, amino, nitro, alkyl, alkoxy, alkoxycarbonyl, alkylcarbonyl, or aminocarbonyl).

Item37. The compound according to anyone of Items 1-35, or pharmaceutically acceptable salt thereof,
R$_6$ is hydrogen, halogen, methyl, ethyl, n-propyl, isopropyl, trifluoromethyl, optionally substituted alkoxy, optionally substituted amino, optionally substituted alkoxycarbonyl, optionally substituted alkylcarbonyl, or optionally substituted aminocarbonyl.

Item38. The compound according to anyone of Items 1-36, or pharmaceutically acceptable salt thereof,
R$_7$ is hydrogen, methyl, ethyl, n-propyl, or isopropyl.

Item39. The compound according to anyone of Items 1-10, 19-21, 36 or 37, or pharmaceutically acceptable salt thereof,
R$_3$ is the following group:

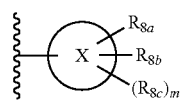

(wherein X, R$_{8a}$, R$_{8b}$, R$_{8c}$, and n are same as the above definition),
R$_4$ is hydrogen, and R$_5$ is hydrogen.

Item40. The compound according to anyone of Items 1-10, 19-21, 36 or 37, or pharmaceutically acceptable salt thereof,
R$_3$ is hydrogen,
R$_4$ is the following group:

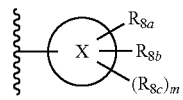

(wherein X, R$_{8a}$, R$_{8b}$, R$_{8c}$, and n are same as the above definition), and
R$_5$ is hydrogen.

Item41. The compound according to anyone of Items 1-10, 31-34, 36 or 37, or pharmaceutically acceptable salt thereof,
R$_3$ is hydrogen,
R$_4$ is hydrogen, and
R$_5$ is the following group:

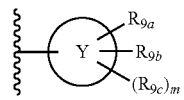

(Y, R$_{9a}$, R$_{9b}$, R$_{9c}$, and m are same as the above definition).

Item42. The compound according to Item1, or pharmaceutically acceptable salt thereof, wherein a compound of formula (1) is compounds of the following formulae:

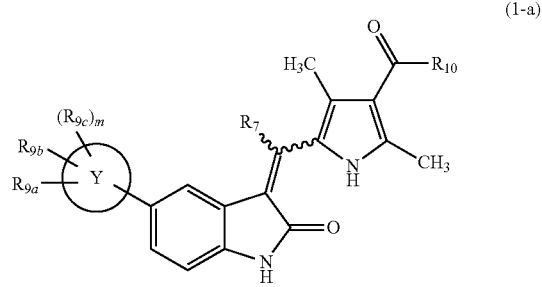

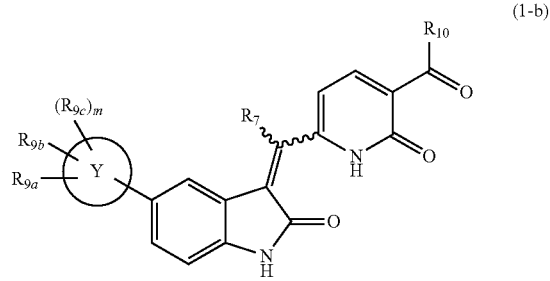

(wherein R$_7$, Y, R$_{9a}$, R$_{9b}$, R$_{9c}$, m, and R$_{10}$ are same as the above definition).

Item43. The compound according to Item1, or pharmaceutically acceptable salt thereof, wherein a compound of formula (1) is compounds of the following formulae:

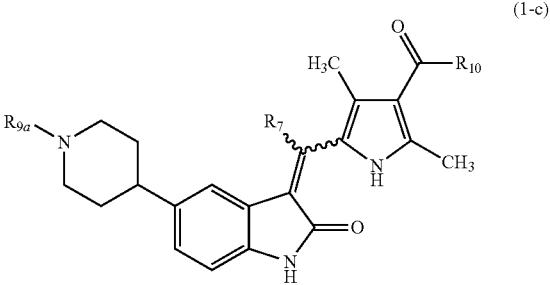

-continued

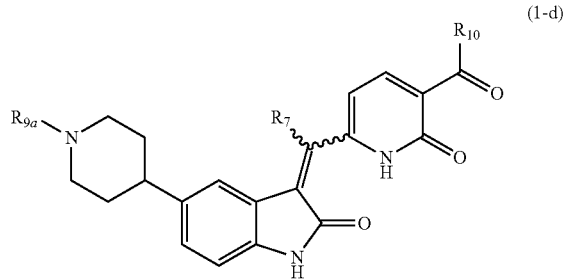

(wherein $R_7$, $R_{9a}$, and $R_{10}$ are same as the above definition).

Item44. The compound according to Item1, or pharmaceutically acceptable salt thereof, wherein a compound of formula (1) is compounds of the following formulae:

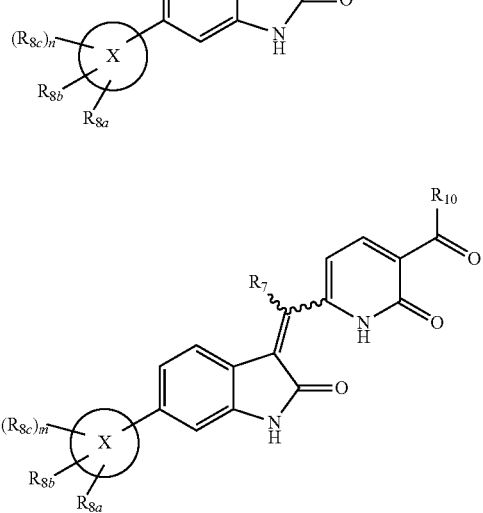

(wherein $R_7$, X, $R_{8a}$, $R_{8b}$, $R_{8c}$, n, and $R_{10}$ are same as the above definition).

Item45. The compound according to Item1, or pharmaceutically acceptable salt thereof, wherein a compound of formula (1) is compounds of the following formulae:

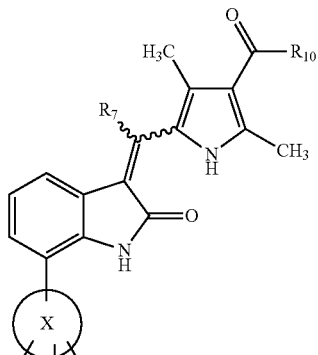

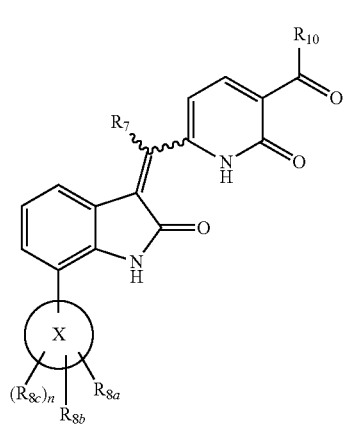

(wherein $R_7$, X, $R_{8a}$, $R_{8b}$, $R_{8c}$, n, and $R_{10}$ are same as the above definition).

Item46. The compound according to Item1, or pharmaceutically acceptable salt thereof, selected from the group consisting of:

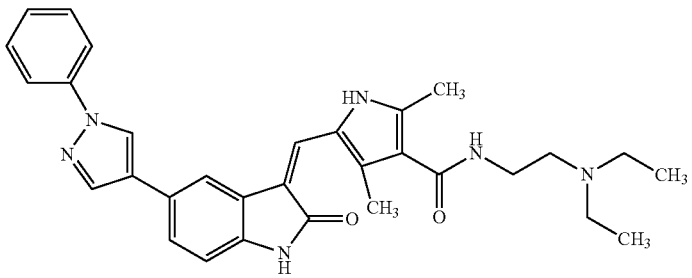

-continued
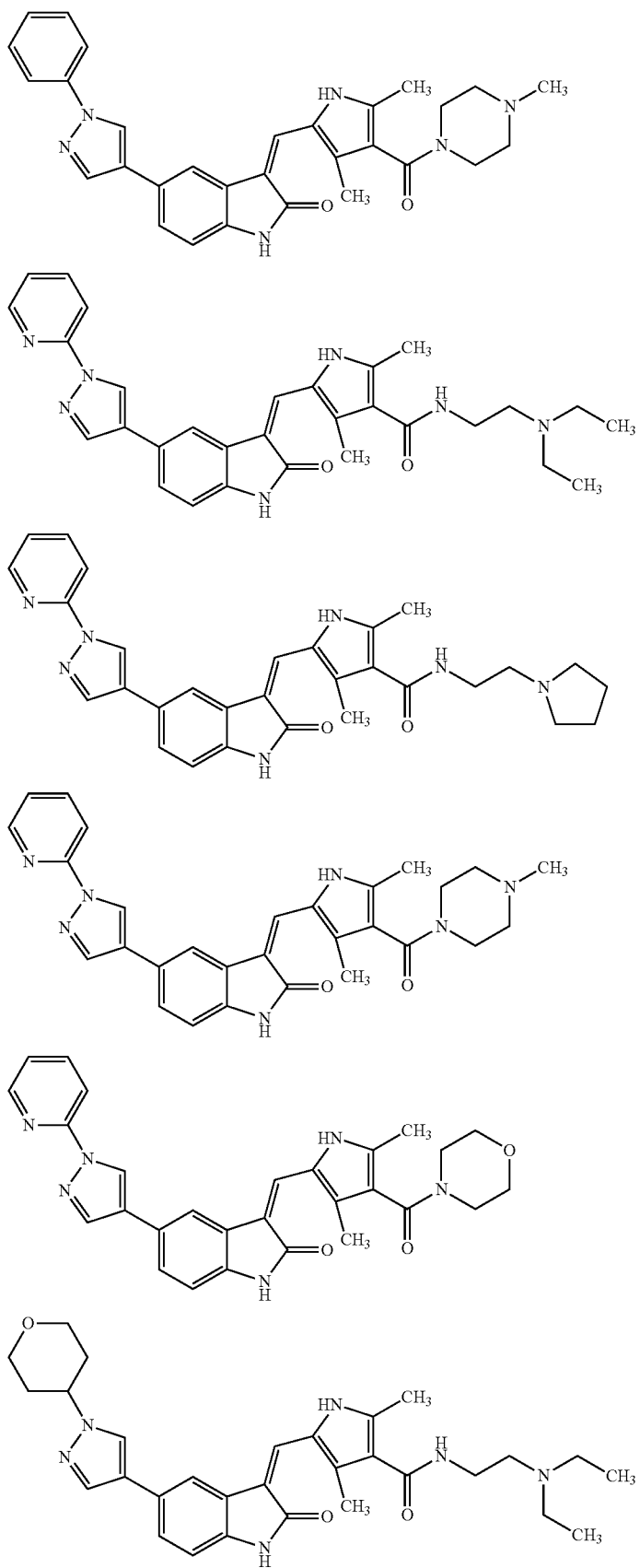

-continued
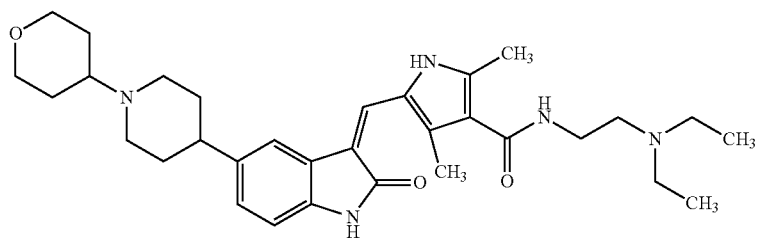
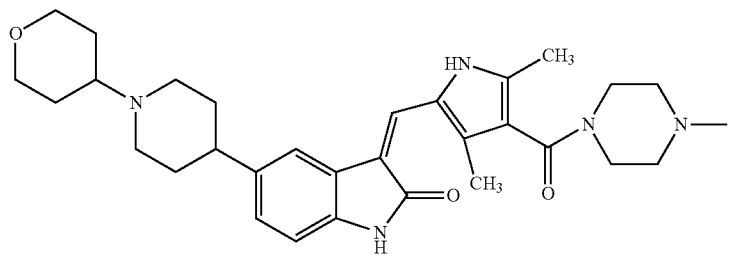
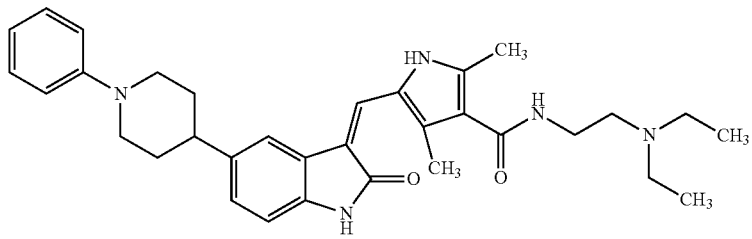
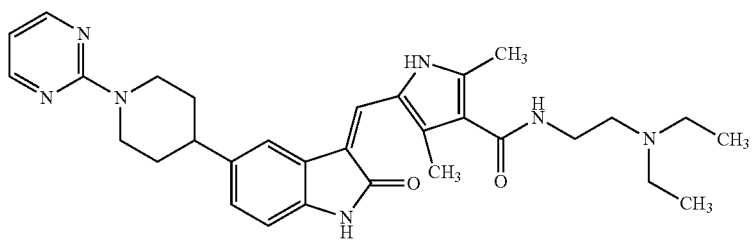
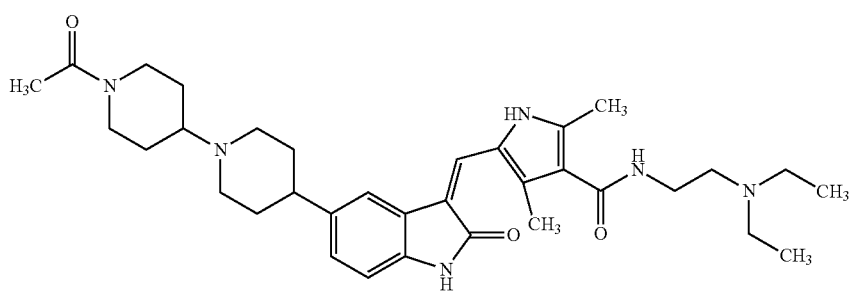
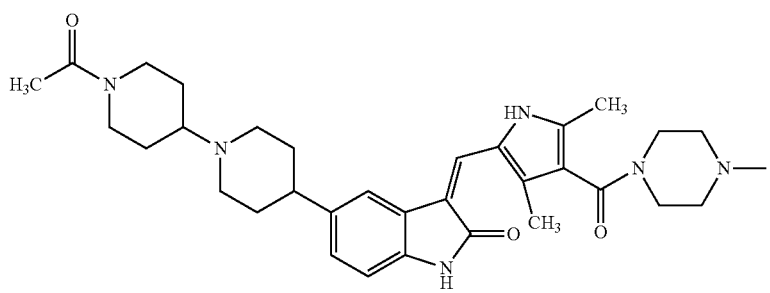

-continued

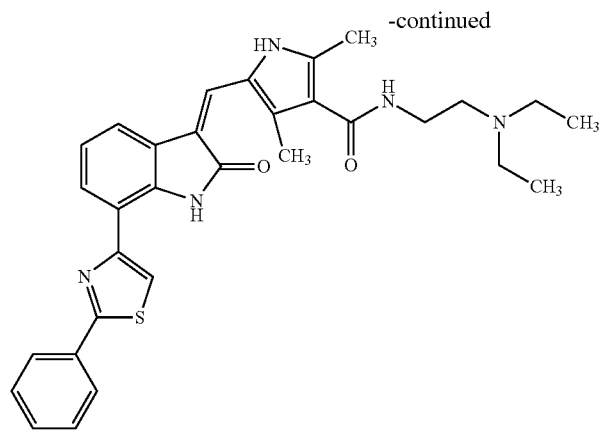

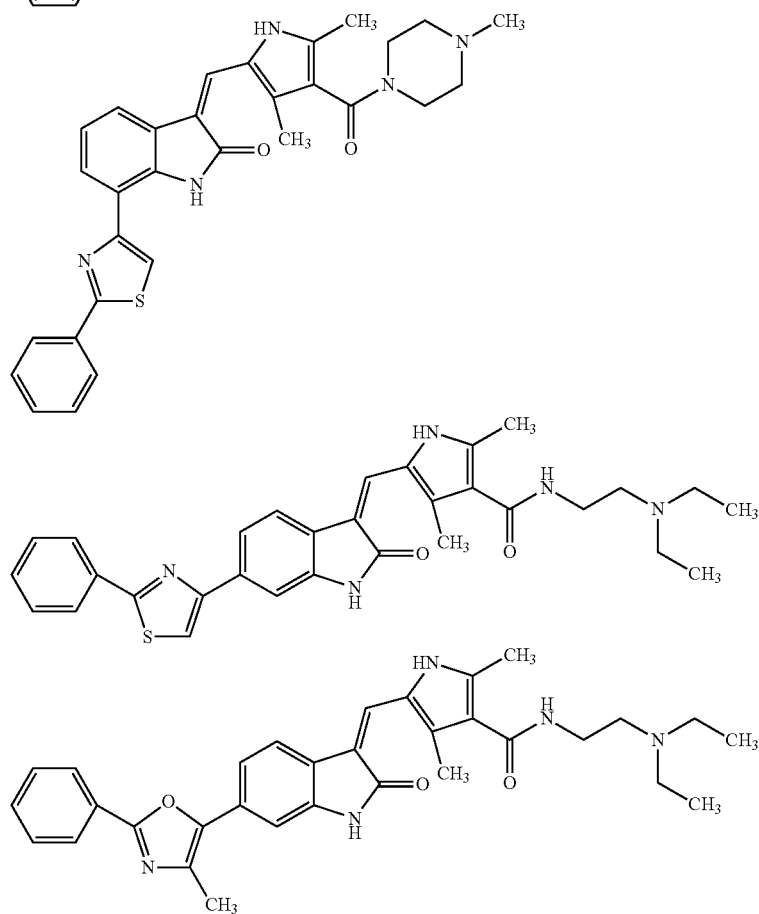

Item47. A pharmaceutical composition comprising the compound anyone of Items 1-46, or pharmaceutically acceptable salt thereof.

Item48. The pharmaceutical composition according to Item 47, for treating cancer in a mammal, comprising to the mammal in need thereof a therapeutically effective amount of said pharmaceutical composition.

Item49. The pharmaceutical composition according to Item 48, wherein the cancer is selected from the group consisting of lung cancer, bladder cancer, head and neck cancer, melanoma, ovarian cancer, prostate cancer, breast cancer, small-cell lung cancer, glioma, colorectal cancer, non-small cell lung cancer, genitourinary cancer, pancreatic cancer, thyroid cancer, Hodgkin's lymphoma, non-Hodgkin's lymphoma, gastrointestinal cancer, gastric cancer, hepatoma, gastrointestinal stromal tumor, squamous cell carcinoma, renal cell carcinoma, astrocytoma, Kaposi's sarcoma, chronic myelogenous leukemia, acute myelogenous leukemia, myeloproliferative disorders, and glioblastoma.

Item50. A method for treating cancer in a mammal, comprising administering to the mammal in need thereof a therapeutically effective amount of the active ingredient the compound of any one of Items 1-46, or pharmaceutically acceptable salt thereof.

Item51. A method for treating cancer in a mammal according to Item 50, wherein the cancer is selected from the group consisting of lung cancer, bladder cancer, head and neck cancer, melanoma, ovarian cancer, prostate cancer, breast cancer, small-cell lung cancer, glioma, colorectal cancer, non-small cell lung cancer, genitourinary cancer, pancreatic cancer, thyroid cancer, Hodgkin's lymphoma, non-Hodgkin's lymphoma, gastrointestinal cancer, gastric cancer, hepatoma, gastrointestinal stromal tumor, squamous cell carcinoma, renal cell carcinoma, astrocytoma, Kaposi's sarcoma, chronic myelogenous leukemia, acute myelogenous leukemia, myeloproliferative disorders, and glioblastoma.

Effect of the Invention

A compound of formula (1), or a pharmaceutically acceptable salt thereof is useful a CSCPKs inhibitor to inhibit, reduce or diminish cancer stem cell survival and/or proliferation in a mammal. A compound of formula (1), or a pharmaceutically acceptable salt thereof is also useful an anti cancer agent.

DESCRIPTION OF EMBODIMENT

The present invention is described in more detail below. The term "group" as used in the specification refers to a monovalent group. For example, the term "alkyl group" refers to a monovalent saturated hydrocarbon group. Moreover, the term "group" is sometimes omitted in the explanation of substituents in the specification.

The number of substituents in groups defined by the phrase "optionally substituted" or "substituted" is not particularly limited as long as the substituents are replaceable, and the number is one or more than one. Moreover, unless otherwise particularly specified, the explanation of each group is also applicable when the groups are part or substituents of other groups. Furthermore, in the specification, groups that are not modified by the phrase "optionally substituted" or "substituted" refer to "unsubstituted" groups.

The term "alkyl" refers to a straight or branched chain alkane (hydrocarbon) radical containing from 1 to 12 carbon atoms, preferably 1 to 6 carbon atoms, more preferably 1 to 4 carbon atoms. The example of "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. "Optionally substituted alkyl" refers to an alkyl group optionally substituted with one or more substituents, preferably 1 to 4 substituents, at any available point of attachment.

The substituents include, but are not limited to, one or more of the following groups: hydrogen, halogen, cyano, nitro, amino, cycloalkyl, alkenyl, cycloalkenyl, alkynyl, heteroalicyclic, aryl, heteroaryl, alkoxy, thioxo, sulfoxide, alkoxysulfonyl, aminosulfonyl, alkoxycarbonyl optionally substituted with hydroxyl or amino, alkylcarbonyl optionally substituted amino, or aminocarbonyl optionally substituted with hydroxyl or amino.

Preferable substituents are selected from the group consisting of alkyl, alkenyl, alkynyl, hydroxy, amino, nitro, cyano, halogen, alkoxy, alkylcarbonyl, alkoxycarbonyl, aminocarbonyl, aryl, heteroaryl, cycloalkyl, and heteroalicyclic.

The term "alkenyl" refers to a straight or branched chain hydrocarbon radical containing from 2 to 12 carbon atoms and at least one carbon-carbon double bond. The such groups include, for example, ethenyl or allyl.

The term "alkynyl" refers to a straight or branched chain hydrocarbon radical containing from 2 to 12 carbon atoms and at least one carbon to carbon triple bond. Examples of such group include, for example, ethinyl.

The term "cycloalkyl" refers to a fully saturated cyclic hydrocarbon group containing from 1 to 4 rings and 3 to 8 carbons per ring. Examples of such group include, for example, cyclopropyl, cyclobutyl, cyclopentyl, cyclohexyl, or cycloheptyl.

"Optionally substituted cycloalkyl" refers to a cycloalkyl group substituted with one or more substituents, preferably 1 to 4 substituents, at any available point of attachment. The examples of substituent in optionally substituted cycloalkyl include, but are not limited to, nitro, cyano, or alkyl optionally substituted with hydroxy or alkoxy.

The "alkyl" moiety of "alkoxy" has the same meaning as defined in the "alkyl".

Preferable one is a straight or branched chain alkoxy radical containing from 1 to 12 carbon atoms, preferably 1 to 6 carbon atoms, more preferably 1 to 4 carbon atoms. Examples of "alkoxy" include methoxy, ethoxy, propoxy, isopropoxy, butoxy, isobutoxy, sec-butoxy, or tert-butoxy.

"Optionally substituted alkoxy" refers to an alkoxy group optionally substituted with one or more substituents, preferably 1 to 4 substituents, at any available point of attachment.

The substituents include, but are not limited to, one or more of the following groups: hydrogen, halogen, cyano, nitro, amino, cycloalkyl, alkenyl, cycloalkenyl, alkynyl, heteroalicyclic, aryl, heteroaryl, alkoxy, thioxo, sulfoxide, alkoxysulfonyl, aminosulfonyl, alkoxycarbonyl optionally substituted with hydroxyl or amino, alkylcarbonyl optionally substituted amino, or aminocarbonyl optionally substituted with hydroxyl or amino.

Preferable substituents are selected form the groups consisting of alkyl, alkenyl, alkynyl, hydroxy, amino, nitro, cyano, halogen, alkoxy, alkylcarbonyl, alkoxycarbonyl, aminocarbonyl, aryl, heteroaryl, cycloalkyl, and heteroalicyclic The term "aryl" refers to cyclic, aromatic hydrocarbon groups that have 1 to 5 aromatic rings, especially monocyclic or bicyclic groups such as phenyl, biphenyl or naphthyl.

Where containing two or more aromatic rings (bicyclic, etc), the aromatic rings of the aryl group may be joined at a single point (e.g., biphenyl), or fused (e.g., naphthyl, phenanthrenyl and the like).

"Optionally substituted aryl" refers to an aryl group substituted by one or more substituents, preferably 1 to 3 substituents, at any point of attachment.

Examples of substituent include, but are not limited to, halogen, hydroxy, cyano, amino, nitro, optionally substituted with alkyl, optionally substituted with alkenyl, optionally substituted with alkynyl, optionally substituted with alkoxy, alkoxycarbonyl, alkylcarbonyl, or aminocarbonyl.

Preferable substituents are selected from the groups consisting of hydroxy, cyano, amino, nitro, alkyl, alkenyl, alkynyl, alkoxy, alkoxycarbonyl, alkylcarbonyl, and aminocarbonyl.

The term "heteroaryl" refers to 5 to 12-membered mono- or poly-cyclic aromatic group, and comprises the same or different and one or more (e.g., 1 to 4) heteroatoms selected from nitrogen atom, sulfur atom or oxygen atom. A preferable "polycyclic heteroaryl" is bi- or tri-cyclic group, more preferably bicyclic group. The polycyclic heteroaryl includes a condensed ring of the above monocyclic heteroaryl with an aromatic ring (including benzene, pyridine) or a non-aromatic ring (including cyclohexyl). The term "five membered heteroaryl" refers to 5-membered mono-cyclic aromatic group, and comprises the same or different and one or more (e.g., 1 to 4) heteroatoms selected from nitrogen atom, sulfur atom or oxygen atom.

Concrete examples of the "heteroaryl" include, but not limited to, pyrrole, furan, thiophene, imidazole, pyrazole, oxazole, isoxazole, thiazole, isothiazole, triazole, thiadiazole, oxadiazole, pyrrolidine, piperidine, azepane, tetrahydrofuran, oxane, or oxepane.

"Optionally substituted heteroaryl" and "optionally substituted five membered heteroaryl" refer to an heteroaryl group substituted by one or more substituents, preferably 1 to 3 substituents, at any point of attachment, more preferably 1 or 2.

Examples of substituent include, but are not limited to, halogen, hydroxy, cyano, amino, nitro, optionally substituted with alkyl, optionally substituted with alkenyl, optionally substituted with alkynyl, optionally substituted with alkoxy, alkoxycarbonyl, alkylcarbonyl, or aminocarbonyl.

Preferable substituents are selected from the groups consisting of hydroxy, cyano, amino, nitro, alkyl, alkenyl, alkynyl, alkoxy, alkoxycarbonyl, alkylcarbonyl, and aminocarbonyl.

The term "heteroalicyclic" refers to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system.

Examples of monocyclic heteroalicyclic group include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiomorpholinyl, thiomorpholinyl sulfoxide, thiomorpholinyl sulfone, 1,3-dioxolane or tetrahydro-1,1-dioxothienyl.

Examples of bicyclic heteroalicyclic group include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, or tetrahydroquinolinyl. Exemplary tricyclic heterocyclic groups include carbazolyl, benzidolyl, phenanthrolinyl, acridinyl, phenantliridinyl, or xanthenyl.

"Optionally substituted heteroalicyclic" refers to heteroalicyclic groups substituted with one or more substituents, preferably 1 to 4 substituents, at any available point of attachment.

Examples of substituent include, but are not limited to, halogen, hydroxy, cyano, amino, nitro, optionally substituted with alkyl, optionally substituted with alkenyl, optionally substituted with alkynyl, optionally substituted with alkoxy, alkoxycarbonyl, alkylcarbonyl, or aminocarbonyl.

Preferable substituents are selected from the groups consisting of hydroxy, cyano, amino, nitro, alkyl, alkenyl, alkynyl, alkoxy, alkoxycarbonyl, alkylcarbonyl, and amino carbonyl.

The terms "halogen" or "halo" refer to chlorine, bromine, fluorine or iodine.

The "alkoxycarbonyl" is a group wherein the "alkoxy" binds to carbonyl.

Preferable "alkoxycarbonyl" is the group having 1 to 12 carbon atoms, preferably 1 to 6 carbon atoms, more preferably 1 to 4 carbon atoms.

Specifically, it includes methoxycarbonyl, ethoxycarbonyl, propoxycarbonyl, 2-propoxycarbonyl, or tert-butoxycarbonyl.

"Optionally substituted alkoxycarbonyl" refers to an alkoxy group optionally substituted with one or more substituents, preferably 1 to 2 substituents, at any available point of attachment.

The substituents include, but are not limited to, one or more of the following groups: hydrogen, halogen, cyano, nitro, amino, cycloalkyl, alkenyl, cycloalkenyl, alkynyl, heteroalicyclic, aryl, heteroaryl, alkoxy, thioxo, sulfoxide, alkoxysulfonyl, aminosulfonyl, alkoxycarbonyl optionally substituted with hydroxyl or amino, alkylcarbonyl optionally substituted amino, or aminocarbonyl optionally substituted with hydroxyl or amino.

Preferable substituents are selected form the groups consisting of alkyl, alkenyl, alkynyl, hydroxy, amino, nitro, cyano, halogen, alkoxy, alkylcarbonyl, alkoxycarbonyl, aminocarbonyl, aryl, heteroaryl, cycloalkyl, and heteroalicyclic The "alkylcarbonyl" means a group wherein the "alkyl" binds to carbonyl.

Preferable "alkylcarbonyl" is the group having 1 to 12 carbon atoms, preferably 1 to 6 carbon atoms, more preferably 1 to 4 carbon atoms.

Specifically, it includes acetyl, propionyl or butyryl.

"Optionally substituted alkylcarbonyl" refers to an alkoxy group optionally substituted with one or more substituents, preferably 1 to 2 substituents, at any available point of attachment.

The substituents include, but are not limited to, one or more of the following groups: hydrogen, halogen, cyano, nitro, amino, cycloalkyl, alkenyl, cycloalkenyl, alkynyl, heteroalicyclic, aryl, heteroaryl, alkoxy, thioxo, sulfoxide, alkoxysulfonyl, aminosulfonyl, alkoxycarbonyl optionally substituted with hydroxyl or amino, alkylcarbonyl optionally substituted amino, or aminocarbonyl optionally substituted with hydroxyl or amino.

Preferable substituents are selected from the groups consisting of alkyl, alkenyl, alkynyl, hydroxy, amino, nitro, cyano, halogen, alkoxy, alkylcarbonyl, alkoxycarbonyl, aminocarbonyl, aryl, heteroaryl, cycloalkyl, and heteroalicyclic The substituent of "optionally substituted amino" refers to an amino group optionally substituted with one or more substituents, preferably 1 or 2 substituent(s), at any available point of attachment.

The substituents include, but are not limited to, one or more of the following groups: halogen, cyano, nitro, amino, cycloalkyl, alkenyl, cycloalkenyl, alkynyl, heteroalicyclic, aryl, heteroaryl, alkoxy, thioxo, sulfoxide, alkoxysulfonyl, aminosulfonyl, alkoxycarbonyl optionally substituted with hydroxyl or amino, alkylcarbonyl optionally substituted amino, or aminocarbonyl optionally substituted with hydroxyl or amino.

Preferable substituents are selected form the groups consisting of alkyl, alkenyl, alkynyl, hydroxy, amino, nitro, cyano, halogen, alkoxy, alkylcarbonyl, alkoxycarbonyl, aminocarbonyl, aryl, heteroaryl, cycloalkyl, and heteroalicyclic.

The "optionally substituted amino" in the "optionally substituted aminocarbonyl" has the same meaning as defined in the "optionally substituted amino".

A preferable embodiment in the present invention is explained in more detail.

R$_1$ is preferably optionally substituted heteroaryl, or optionally substituted heteroalicyclic, wherein the heteroaryl is selected from the group consisting of pyrrole, furan, thiophene, pyridine, pyrimidine, pyrazine, pyridazine, indole, and pyrrolopyridinone, and heteroalicyclic is selected from the group consisting of pyridone, pyrrolidine, and piperidine, more preferably, optionally substituted heteroaryl, or optionally substituted heteroalicyclic, wherein heteroaryl is pyrrole, or pyrrolopyridinone, and heteroalicyclic is pyridine.

R$_1$ is more preferably one of the group selected from the following group:

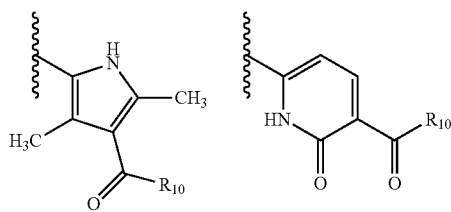

(wherein R$_{10}$ is same as the above definition).

R$_{10}$ is preferably hydroxy, mono-substituted alkyl amino (said alkyl is substituted by di-substituted alkyl amino, or heteroalicyclic), piperazynyl, homopiperazynyl or morphorinyl, more preferably, hydroxy, ethyl amino (said ethyl is substituted by di-ethyl amino, 1-pyrrolidino), or 4-piperazinyl (said piperazinyl is substituted with alkyl), more preferably, hydroxy, 2-(di-ethyl amino)ethyl amino, 2-pyrrolidino ethyl amino, 4-methyl piperazinyl or morpholino.

R$_2$ is preferably hydrogen, or optionally substituted alkyl, more preferably, hydrogen.

R$_3$, and R$_4$ are preferably each independently
1: hydrogen, 2: halgen, 3: cyano, 4: nitoro, 5: hydroxy, 6: alkyl. 7: alkoxy, 8: amino, 9: alkylcarbonyl, 10: alkoxycarbonyl, 11: aminocarbonyl, and
12: the following group:

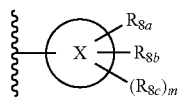

(wherein X, R$_{8a}$, R$_{8b}$, R$_{8c}$, and n are same as the above definition),
wherein said alkyl, alkoxy, amino, alkylcarbonyl, alkoxycarbonyl, and aminocarbonyl are optionally substituted with one or more substitutent(s) selected from the group consisting of (a) alkyl, (b) alkenyl, (c) alkynyl, (d) hydroxy, (e) amino, (f) nitro, (g) cyano, (h) halogen, (i) alkoxy, (j) alkylcarbonyl, (k) alkoxycarbonyl, (l) aminocarbonyl, (m) aryl, (n) heteroaryl, (o) cycloalkyl, and (p) heteroalicyclic), more preferably, R$_3$, and R$_4$ are each independently 1: hydrogen, 2: halogen, 3: alkyl(said alkyl is optionally substituted with one or more substituent(s) selected from the group consisting of (a) alkyl, (b) alkenyl, (c) alkynyl, (d) hydroxy, (e) amino, (f) nitro, (g) cyano, (h) halogen, (i) alkoxy, (j) alkylcarbonyl, (k) alkoxycarbonyl, (l) aminocarbonyl, (m) aryl, (n) heteroaryl, (l) ocycloalkyl, and (o) heteroalicyclic),
or
4: the following group:

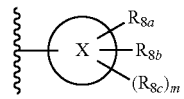

(wherein X, R$_{8a}$, R$_{8b}$, R$_{8c}$, and n are same as the above definition), more preferably, R$_3$, and R$_4$ are each independently hydrogen, or the following group:

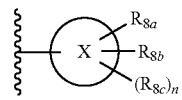

(wherein X, R$_{8a}$, R$_{8b}$, R$_{8c}$, and n are same as the above definition).

X is preferably thiophene, pyrazole, oxazole, thiazole, thiadiazole, or oxadiazole, more preferably, X is pyrazole, thiazole, or oxazole.

X is preferably piperidine.

R$_{8a}$, R$_{8b}$ and R$_{8c}$ are preferably each independently hydrogen, alkyl, halogen, cyano, amino, nitro, hydroxy, trifluoromethyl, phenyl, or pyridyl, more preferably, R$_{8a}$, R$_{8b}$ and R$_{8c}$ are each dependently hydrogen, alkyl, phenyl, or pyridyl.

n is preferably the integra 0.

In case that X is selected from the group consisting of the following group:

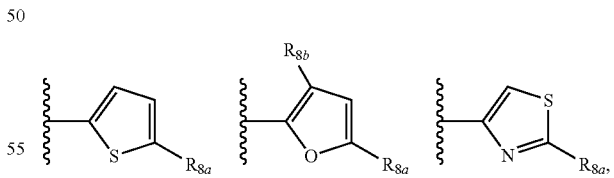

R$_{8a}$ is preferably piperidinyl, pyranyl, phenyl, thiophenyl, pyrazinyl, pyrimidinyl, pyridazinyl, or pyridyl (said piperidinyl, pyranyl, phenyl, thiophenyl pyrazinyl, pyrimidinyl, pyridazinyl, or pyridyl are optionally substituted with halogen, hydroxy, cyano, amino, nitro, alkyl, alkoxy, alkoxycarbonyl, alkylcarbonyl, or aminocarbonyl), and R$_{8b}$ is preferably alkyl.

In case that X is selected from the group consisting of the following group:

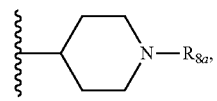

and

R$_{8a}$ is preferably 4-piperazinyl (said piperidinyl is substituted with alkyl or alkylcarbonyl), 4-tetrahydropyranyl, phenyl, pyrazinyl, pyrimidinyl, pyridazinyl, or pyridiyl (said phenyl, pyrazinyl, pyrimidinyl, pyridazinyl, or pyridyl are optionally substituted with halogen, hydroxy, cyano, amino, nitro, alkyl, alkoxy, alkoxycarbonyl, alkylcarbonyl, or aminocarbonyl).

In a compound of formula (1), R$_5$ is 1: hydrogen, 2: halgen, 3: cyano, 4: nitoro, 5: hydroxy, 6: alkyl, 7: alkoxy, 8: amino, 9: alkylcarbonyl, 10: alkoxycarbonyl, 11: aminocarbonyl, and 12: the following group:

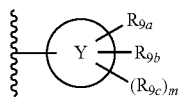

(wherein Y, R$_{9a}$, R$_{9b}$, R$_{9c}$, and m are same as the above definition), wherein said alkyl, alkoxy, amino, alkylcarbonyl, alkoxycarbonyl, and aminocarbonyl are optionally substituted with one or more substituent(s) selected from the group consisting of (a) alkyl, (b) alkenyl, (c) alkynyl, (d) hydroxy, (e) amino, (f) nitro, (g) cyano, (h) halogen, (i) alkoxy, (j) alkylcarbonyl, (k) alkoxycarbonyl, (l) aminocarbonyl, (m) aryl, (n) heteroaryl, (l) cycloalkyl, and (o) heteroalicyclic, more preferably, R$_5$ is hydrogen, or the following group:

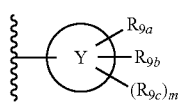

(wherein Y, R$_{9a}$, R$_{9b}$, R$_{9c}$, and m are same as the above definition).

Y is preferably pyrrole, furan, thiophene, imidazole, pyrazole, oxazole, isoxazole, thiazole, isothiazole, triazole, thiadiazole, or oxadiazole, more preferably, Y is furan, thiophene, imidazole, pyrazole, oxazole, thiazole, triazole, thiadiazole, oxadiazole.

Y is preferably piperidine.

R$_{9a}$ is preferably phenyl or pyridyl(said pheny and pyridyl are optionally substituted with hydroxy, amino, nitro, cyano, alkyl, alkoxyl, trifluoromethyl, and halogen.

R$_{9b}$ and R$_{9c}$ are preferably each dependently hydrogen, methyl, ethyl, halogen, cyano, amino, nitro, hydroxy, or trifluoromethyl.

R$_{9b}$ is preferably each dependently hydrogen, methyl, ethyl, halogen, cyano, amino, nitro, hydroxy, or trifluoromethyl.

m is preferably the integra 0.

In case that R$_5$ is selected from the group consisting of the following group:

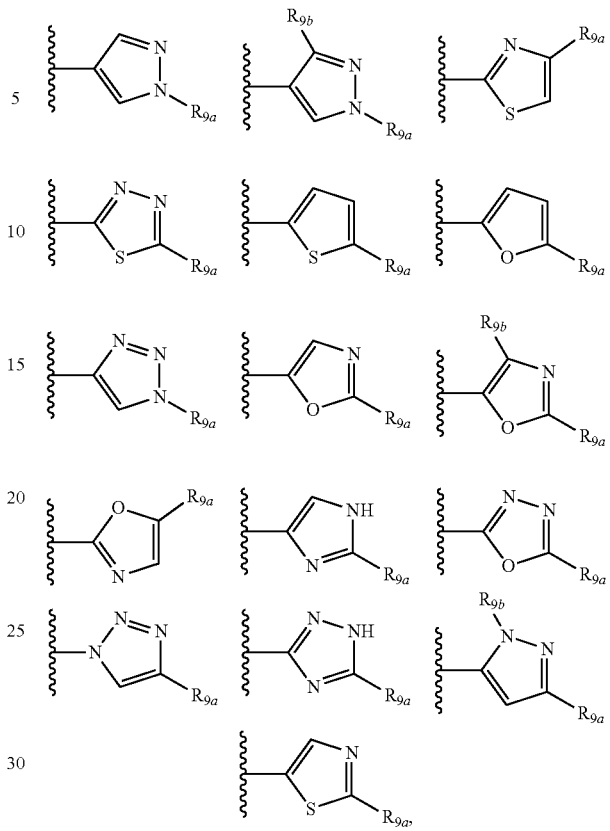

R$_{9a}$ is preferably piperidinyl, pyranyl, phenyl, thiophenyl, pyrazinyl, pyrimidinyl, pyridazinyl or pyridyl (said piperidinyl, pyranyl, phenyl, thiophenyl pyrazinyl, pyrimidinyl, pyridazinyl, or pyridyl are optionally substituted with halogen, hydroxy, cyano, amino, nitro, alkyl, alkoxy, alkoxycarbonyl, alkylcarbonyl, or aminocarbonyl), and R$_{9b}$ is preferably alkyl.

In case that Y is selected from the group consisting of the following group:

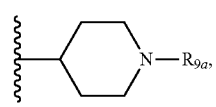

and

R$_{9a}$ is 4-piperazinyl (said piperidinyl is substituted with alkyl or alkylcarbonyl), 4-tetrahydropyranyl, phenyl, pyrazinyl, pyrimidinyl, pyridazinyl, or pyridiyl (said phenyl, pyrazinyl, pyrimidinyl, pyridazinyl, or pyridyl are optionally substituted with halogen, hydroxy, cyano, amino, nitro, alkyl, alkoxy, alkoxycarbonyl, alkylcarbonyl, or aminocarbonyl).

R$_6$ is preferably hydrogen halogen cyano, or optionally substituted alkyl, more preferably, R$_6$ is hydrogen.

R$_7$ is hydrogen, methyl, ethyl, n-propyl, or isopropyl, more preferably, R$_7$ is hydrogen.

Preferable compound in the present invention is the compound selected the group consisting of the following:

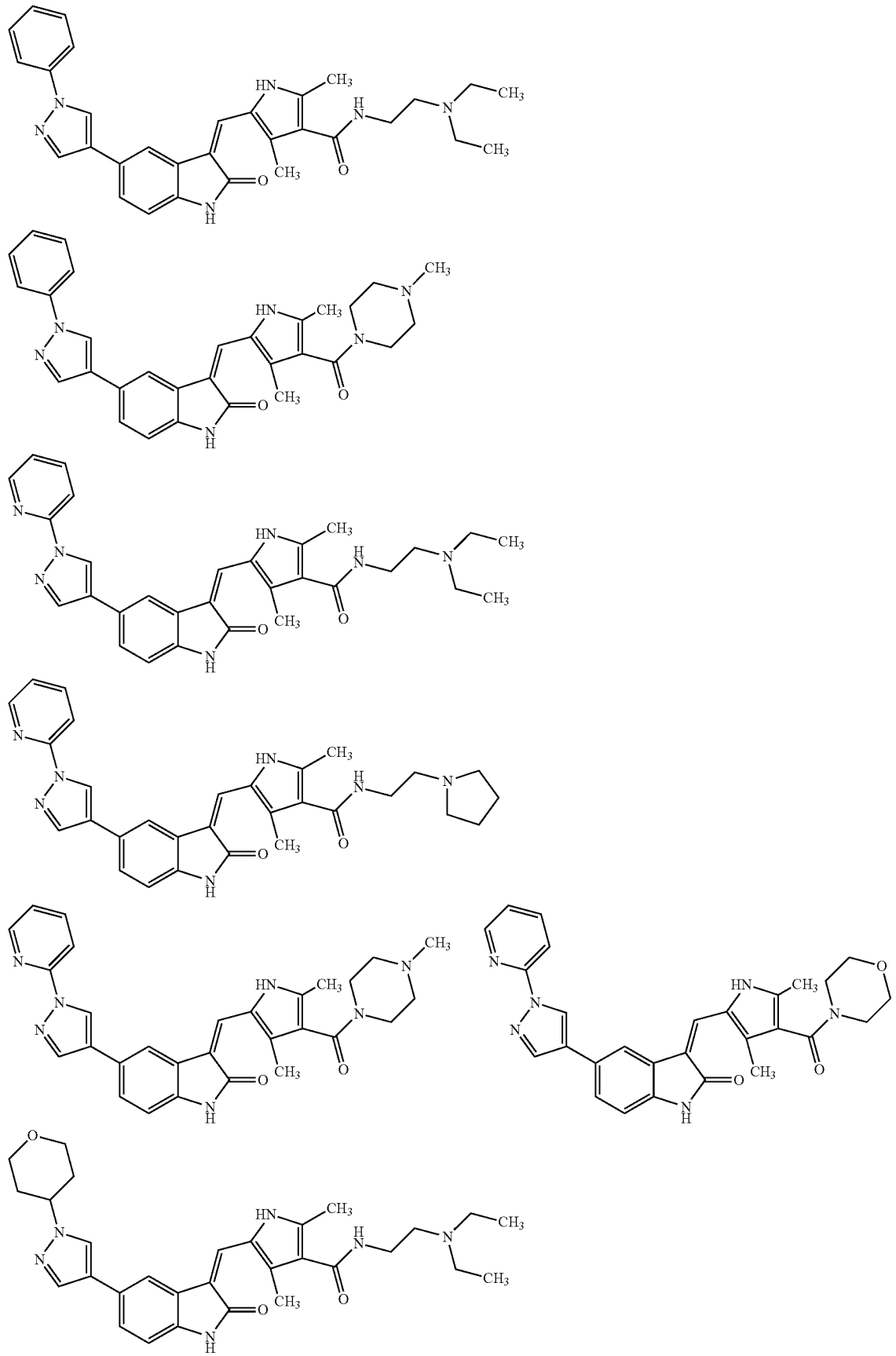

-continued
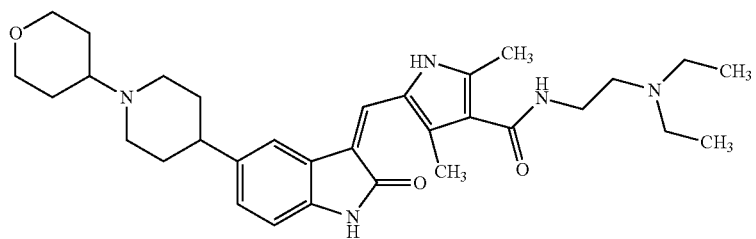
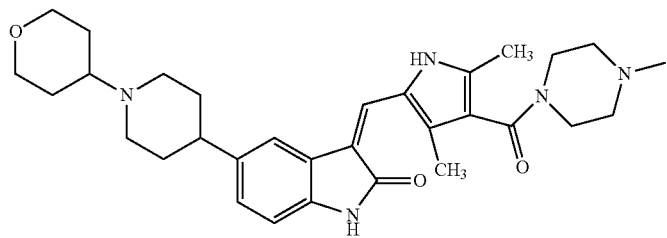
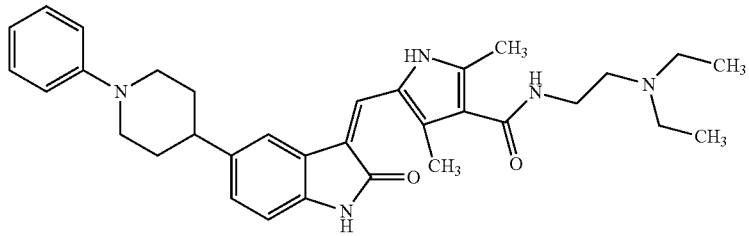
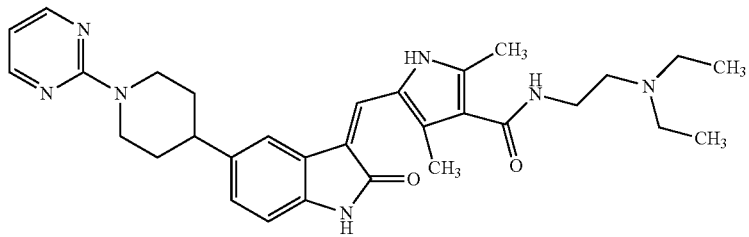
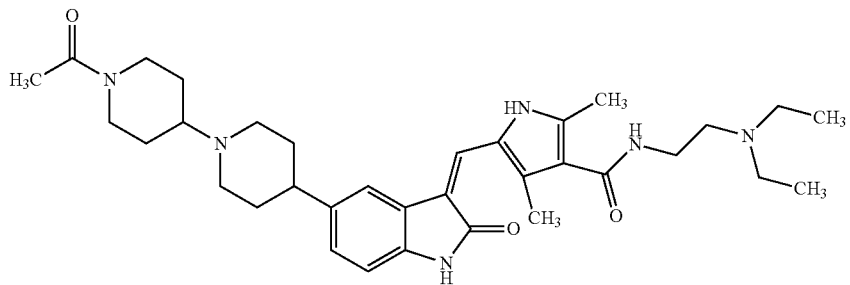
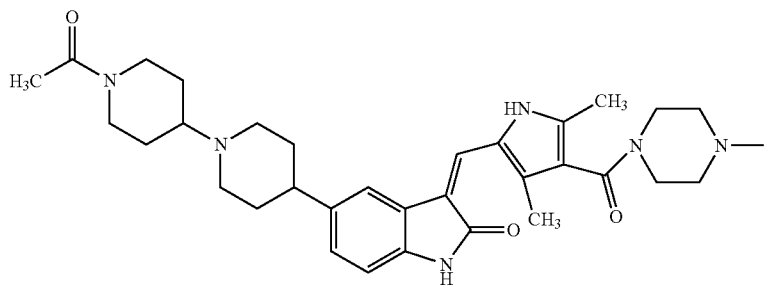

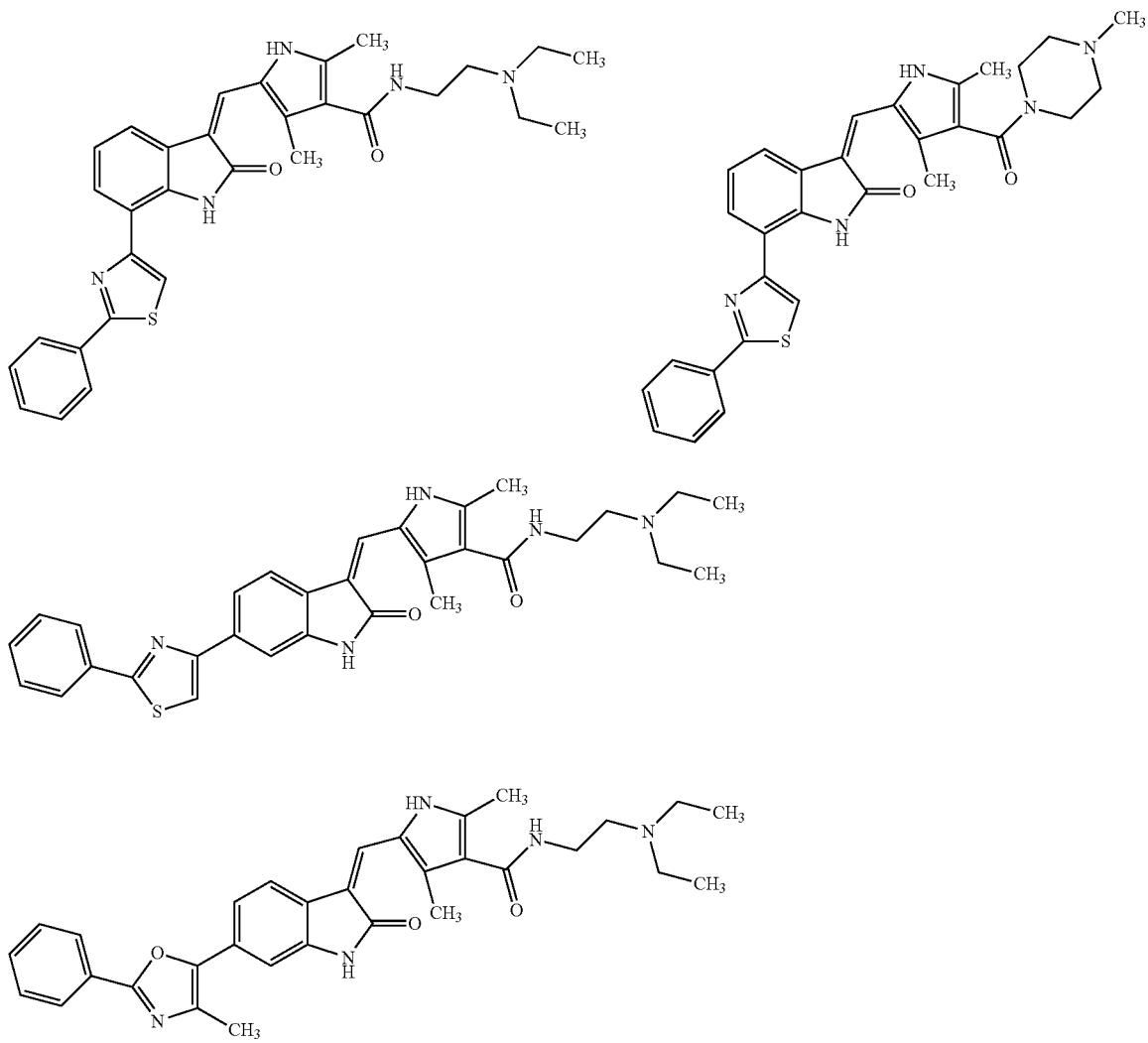

In case of compound of formula (1), preferably,
R_3 and R_4 are each hydrogen, and
R_5 is the following group:

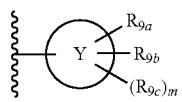

(wherein Y, $R_{9a}$, $R_{9b}$, $R_{9c}$, and m are same as the above definition); or
R_3 is the following group:

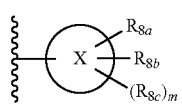

(wherein X, $R_{8a}$, $R_{8b}$, $R_{8c}$, and n are same as the above definition), and
R_4 and R_5 are each hydrogen; or
R_3 is hydrogen, R_4 is the following group:

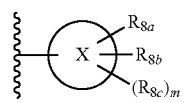

(wherein X, $R_{8a}$, $R_{8b}$, $R_{8c}$, and n are same as the above definition), and
R_5 is hydrogen, A compound of formula (1) is preferably compounds explained in the following (1) to (4). Each definition in these compounds is the same as defined above. A preferable embodiment of the definition is also the same as defined above.

(1) A compound of the following formula (1-a), or a pharmaceutically acceptable salt thereof.

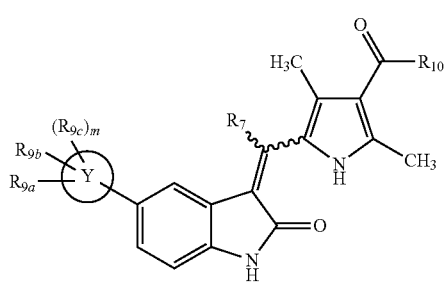

(1-a)

(2) A compound of the following formula (1-b), or a pharmaceutically acceptable salt thereof.

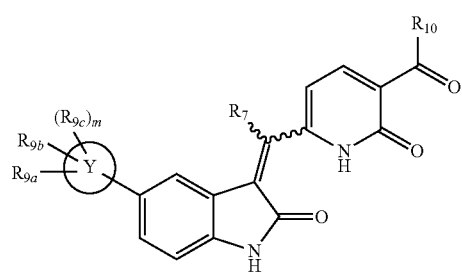

(1-b)

(3) A compound of the following formula (1-c), or a pharmaceutically acceptable salt thereof.

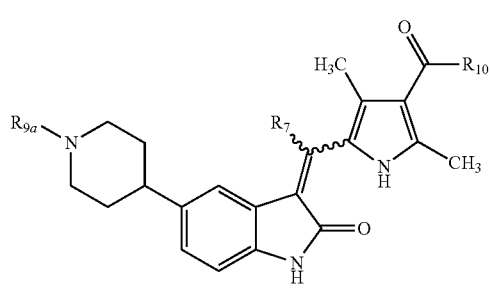

(1-c)

(4) A compound of the following formula (1-d), or a pharmaceutically acceptable salt thereof.

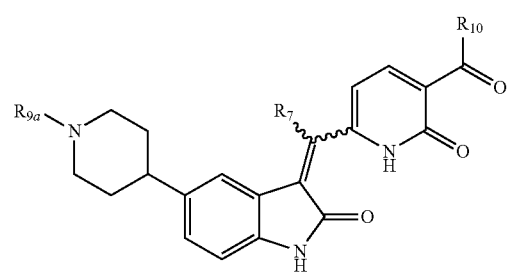

(1-d)

(5) A compound of the following formula (1-e), or a pharmaceutically acceptable salt thereof.

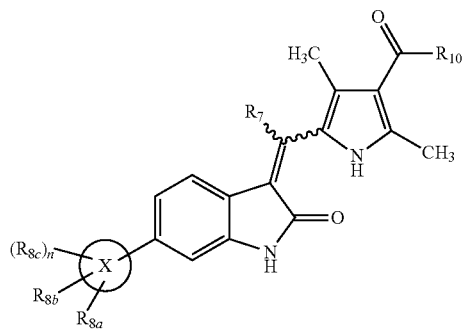

(1-e)

(6) A compound of the following formula (1-f), or a pharmaceutically acceptable salt thereof.

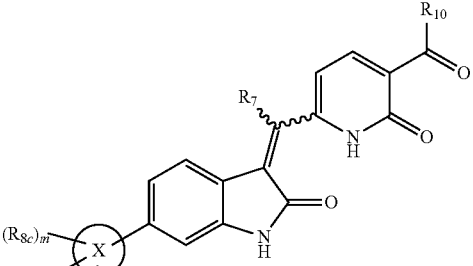

(1-f)

(7) A compound of the following formula (1-g), or a pharmaceutically acceptable salt thereof.

(1-g)

(8) A compound of the following formula (1-h), or a pharmaceutically acceptable salt thereof.

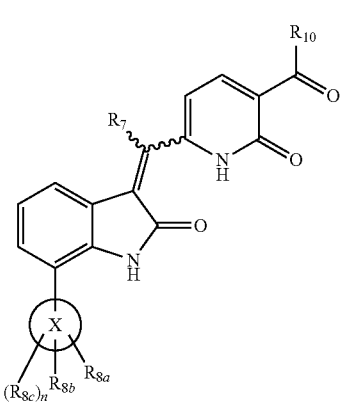

(1-h)

Preparation methods for a compound of formula (1) are explained. A compound formula (1) or a pharmaceutically acceptable salt thereof is illustrated, but the present invention is not intended to be limited thereto.

In the following method, the starting materials and the intermediates of the reaction may be isolated and purified if desired using conventional techniques, including but not limited to filtration, distillation, crystallization, chromatography and the like.

The materials of invention can be characterized by using conventional means including but not limited to physical constants and spectral data. The reactions are performed in solvents appropriate to the reagents and materials employed and are suitable for transformations being effected. The representative examples include, but are not limited to, tetrahyrdofuran, dimethylforamide, methanol, ethanol, water, dimethylforamide, chloroform, dichloromethane, hexane, toluene, 1,4-dioxane or ethyl acetate.

Unless specified, the reactions described herein were performed at atmospheric pressure over a temperature range from about −78° C. to about 150° C.

For heating, any methods can be used which depends on reagent and target material. The representative examples include, but are not limited to, water bath, oil bath, water bath, or microwave reactor.

The compound of formula (1) in the present invention may be prepared from known compounds by optionally combining the method of the following Preparation methods I to II, similar methods to the following Preparation methods, or synthetic known to a skilled person.

Preparation of Method

A compound of formula (1) may be synthesized by the following method.

Preparation of Method I

A compound of formula (1) may be synthesized by the following method.

Among a compound of formula (1), Compound 1-3 or a pharmaceutically acceptable salt thereof is prepared by the following method.

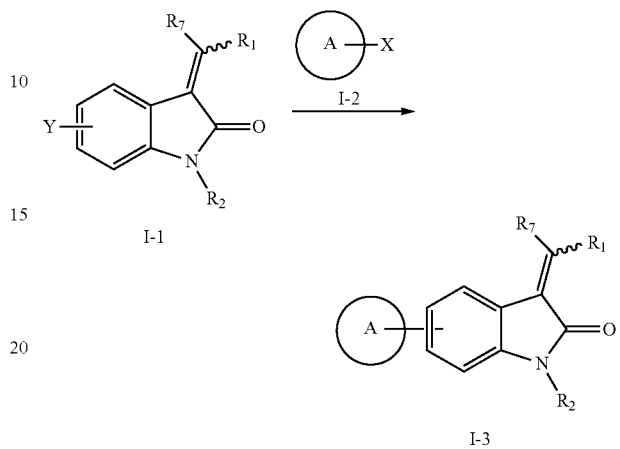

[In the scheme, $R_1$, $R_2$, and $R_7$ are as defined in the above item 1. A is optionally substituted heteroaryl group in $R_3$, $R_4$ and $R_5$ in the above item 1. X is metal containing group such as boronic acid, boronic acid pinacol ester, trifluoro boran, organic tin, zinc halide, magnesium halide, organic silicon, and organic lithium. Y is leaving group such as Cl, Br, I, and OTf.]

A compound of formula 1-1 can react with a compound of formula 1-2 in the presence of transition metal catalyst (rep-

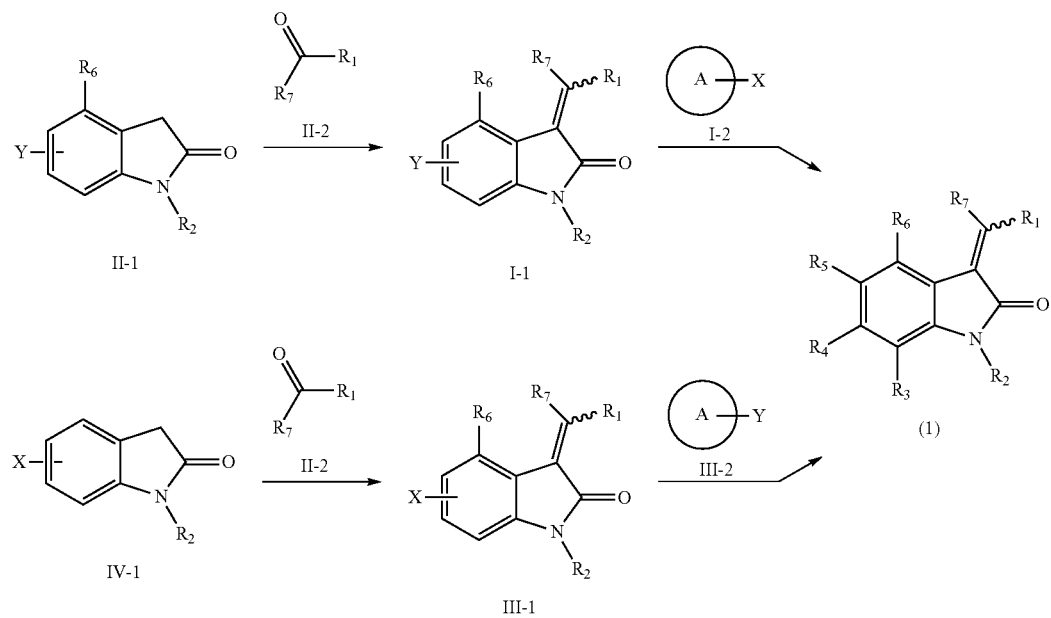

[In the scheme, $R_1$, $R_2$, $R_3$, $R_4$, $R_5$, $R_6$ and $R_7$ are as defined in the above item 1. A is optionally substituted heteroaryl group in $R_3$, $R_4$ and $R_5$ in the above item 1. X is metal containing group such as boronic acid, boronic acid pinacol ester, trifluoro boran, organic tin, zinc halide, magnesium halide, organic silicon, and organic lithium. Y is leaving group such as Cl, Br, I, and OTf.]

resentative examples include, but are not limited to tetrakis (triphenylphosphine)palladium(0), [1,1'-bis(diphenylphosphino)ferrocene]palladium(II) dichloride, palladium carbon, dichlorobis(triphenylphosphine)nickel(II), or bis(triphenylphosphine)palladium(II) dichloride.), alkali metal carbonate (representative examples include, but are not limited to potassium carbonate, sodium carbonate, or cesium carbonate.) or other alkali metal salt (sodium hydroxide, potassium hydroxide, dodium ethoxide, sodium methoxide, sodium tert-butoxide, potassium tert-butoxide, sodium hydride, sodium phosphate, potassium phosphate.) and appropriate solvent or without solvent to give a compound of formula 1-3.

Preparation Method II

A compound I-1 may be prepared from a compound II-2.

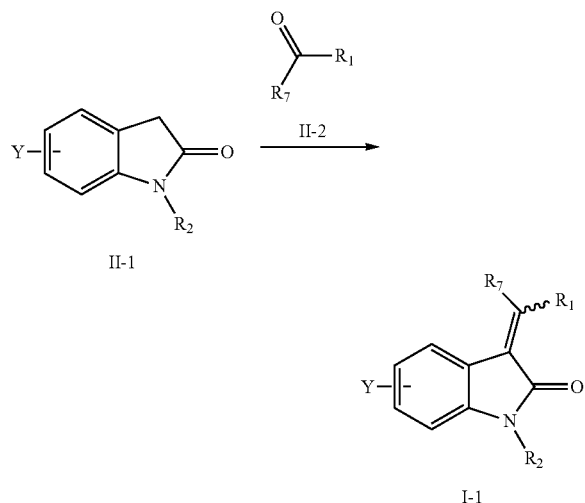

[In the scheme, the symbols have the same meaning as defined above.]

A compound of formula II-1 can react with a compound of formula II-2 in the presence of a base (representative examples include, but are not limited to pyrrolidine and piperidine) or an acid (representative examples include, but are not limited to hydrochloric acid, acetic acid, trifluoroacetic acid), and appropriate solvent or without solvent to give a compound of formula I-1.

Preparation Method III

A compound 1-3 may be prepared from a compound III-1.

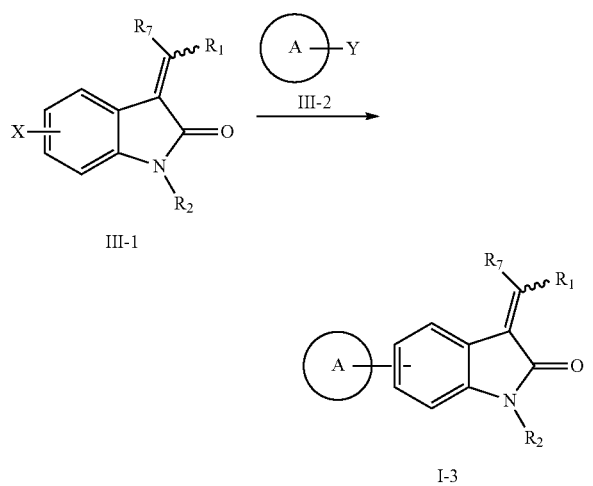

[In the scheme, the symbols have the same meaning as defined above.]

A compound of formula III-1 can react with a compound of formula III-2 in the presence of transition metal catalyst (representative examples include, but are not limited to, tetrakis (triphenylphosphine)palladium(0), [1,1'-bis(diphenylphosphino)ferrocene]palladium(II) dichloride, palladium carbon, dichlorobis(triphenylphosphine)nickel(II), or bis(triphenylphosphine)palladium(II) dichloride.), alkali metal carbonate (representative examples include, but are not limited to, potassium carbonate, sodium carbonate, or cesium carbonate.) or other alkali metal salt (sodium hydroxide, potassium hydroxide, dodium ethoxide, sodium methoxide, sodium tert-butoxide, potassium tert-butoxide, sodium hydride, sodium phosphate, potassium phosphate.), and appropriate solvent or without solvent to give a compound of formula I-3.

Preparation Method IV

A compound III-1 may be prepared from a compound IV-1.

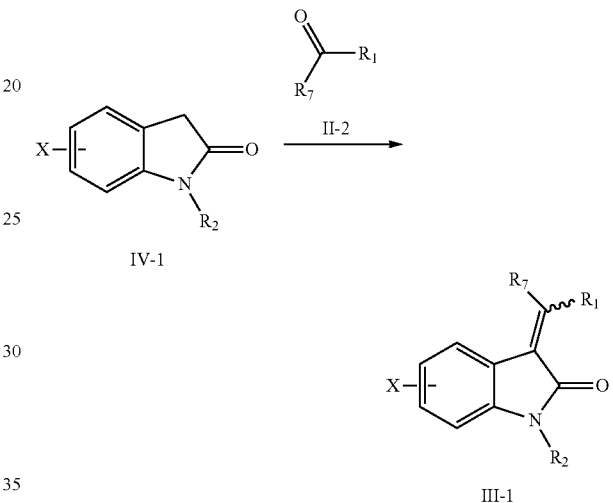

[In the scheme, the symbols have the same meaning as defined above.]

A compound of formula IV-1 can react with a compound of formula II-2 in the presence of a base (representative examples include, but are not limited to pyrrolidine and piperidine) or an acid (representative examples include, but are not limited to hydrochloric acid, acetic acid, trifluoroacetic acid), and appropriate solvent or without solvent to give a compound of formula III-1.

Preparation Method V

A compound of formula III-1 may be prepared from a compound I-1.

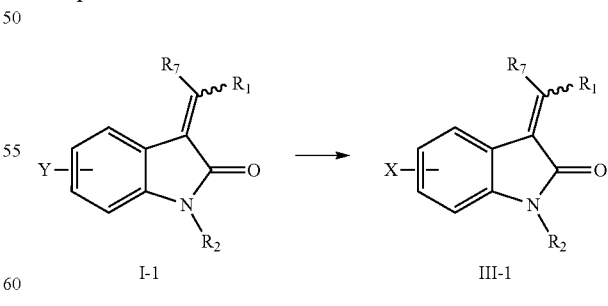

[In the scheme, the symbols have the same meaning as defined above.]

A compound of formula I-1 can react with a compound of boron reagent (representative examples include, but are not limited to, bis(pinacolato)diboron, bis(neopentyl Glycolato) diboron, or bis(catecholato)diboron.) in the presence of transition metal catalyst (representative examples include, but are not limited to, dichloro[1,1'-bis(diphenylphosphino)ferrocene]palladium, [1,1'-bis(diphenylphosphino)ferrocene]palladium(II) dichloride, or bis(triphenylphosphine)palladium(II) dichloride.), alkali metal carbonate or alkali metal acetate (representative examples include, but are not limited to, potassium carbonate, sodium carbonate, cesium carbonate, or potassium acetate.), and appropriate solvent or without solvent to give a compound of formula III-1.

Preparation Method VI

A compound of formula I-3 may be prepared from a compound VI-1.

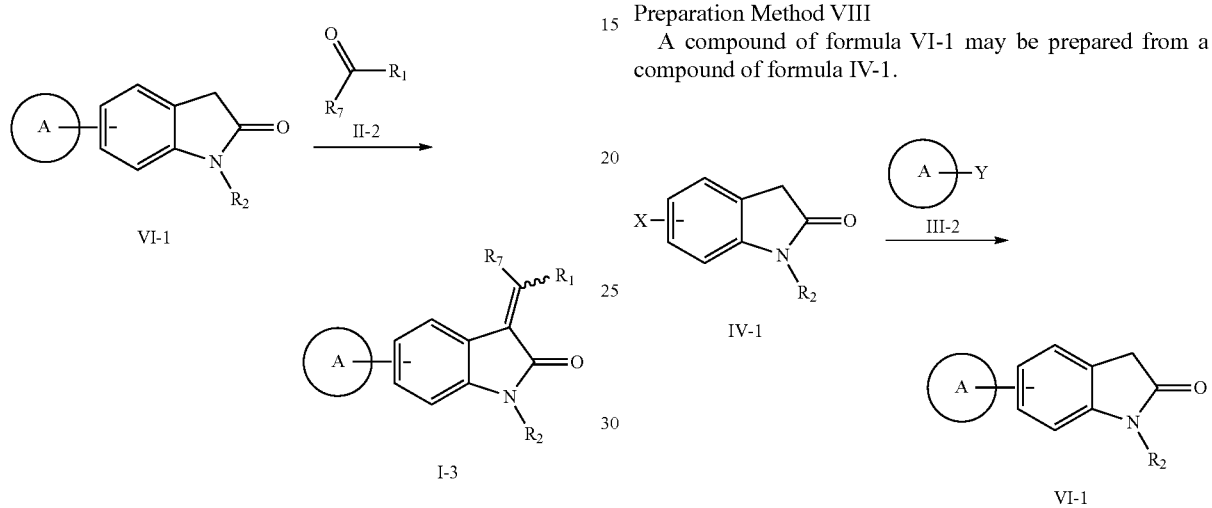

[In the scheme, the symbols have the same meaning as defined above.]

A compound of formula VI-1 can react with a compound of formula II-2 in the presence of a base (representative examples include, but are not limited to pyrrolidine and piperidine) or an acid (representative examples include, but are not limited to hydrochloric acid, acetic acid, trifluoroacetic acid), and appropriate solvent or without solvent to give a compound of formula I-3.

Preparation Method VII

A compound of formula VI-1 may be prepared from a compound of formula II-1.

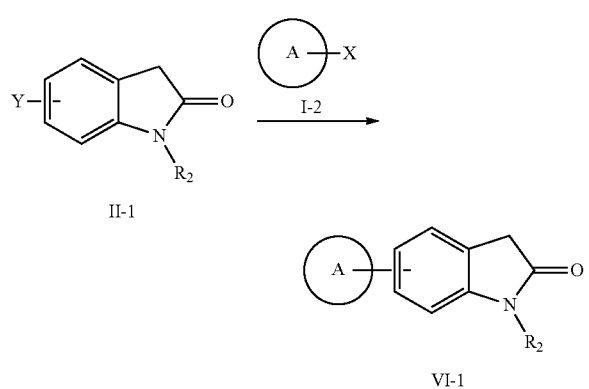

[In the scheme, the symbols have the same meaning as defined above.]

A compound of formula II-1 can react with a compound of formula I-2 in the presence of transition metal catalyst (representative examples include, but are not limited to, tetrakis(triphenylphosphine)palladium(0), [1,1'-bis(diphenylphosphino)ferrocene]palladium(II) dichloride, palladium carbon, dichlorobis(triphenylphosphine)nickel(II), or bis(triphenylphosphine)palladium(II) dichloride.), alkali metal carbonate (representative examples include, but are not limited to, potassium carbonate, sodium carbonate, or cesium carbonate.) or other alkali metal salt (sodium hydroxide, potassium hydroxide, dodium ethoxide, sodium methoxide, sodium tert-butoxide, potassium tert-butoxide, sodium hydride, sodium phosphate, potassium phosphate.), and appropriate solvent or without solvent to give a compound of formula VI-1.

Preparation Method VIII

A compound of formula VI-1 may be prepared from a compound of formula IV-1.

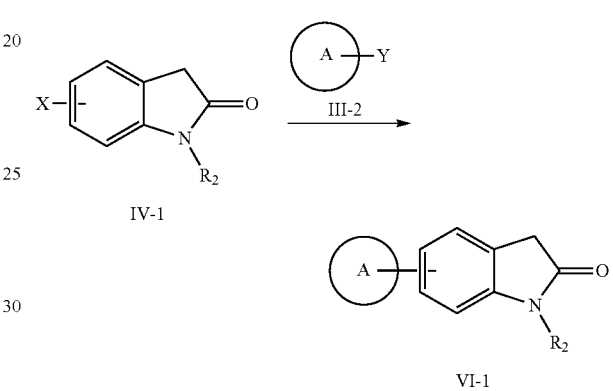

[In the scheme, the symbols have the same meaning as defined above.]

A compound of formula IV-1 can react with a compound of formula III-2 in the presence of transition metal catalyst (representative examples include, but are not limited to, tetrakis(triphenylphosphine)palladium(0), [1,1'-bis(diphenylphosphino)ferrocene]palladium(II) dichloride, palladium carbon, dichlorobis(triphenylphosphine)nickel(II), or bis(triphenylphosphine)palladium(II) dichloride), alkali metal carbonate (representative examples include, but are not limited to, potassium carbonate, sodium carbonate, or cesium carbonate) or other alkali metal salt (sodium hydroxide, potassium hydroxide, dodium ethoxide, sodium methoxide, sodium tert-butoxide, potassium tert-butoxide, sodium hydride, sodium phosphate, potassium phosphate), and appropriate solvent or without solvent to give a compound of formula VI-1.

Preparation Method IX

A compound of formula IX-3 may be prepared from a compound of formula IX-1.

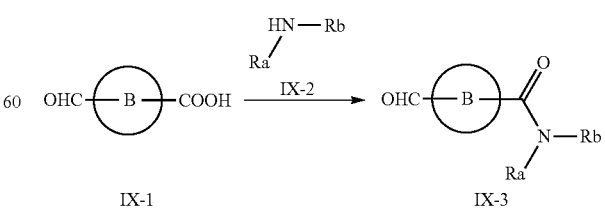

[In the scheme, $R_a$ and $R_b$ are each independently halogen, cyano, nitro, amino, cycloalkyl, alkenyl, cycloalkenyl, alkynyl, heteroalicyclic, aryl, heteroaryl, alkoxy, thioxo, sulfoxide, alkoxysulfonyl, aminosulfonyl, alkoxycarbonyl optionally substituted with hydroxyl or amino, alkylcarbonyl optionally substituted amino, or aminocarbonyl optionally substituted with hydroxyl or amino, B is optionally substituted heteroaryl group or optionally substituted heteroalicyclic group.]

A compound of formula IX-1 can react with a compound of formula IX-2 (representative examples include, but are not limited to, $N^1,N^1$-diethylethane-1,2-diamine, $N^1,N^1$-dimethylethane-1,2-diamine, 2-(pyrrolidin-1-yl)ethanamine, N-methyl-piperazine, N-methyl-homopiperazine, 2-morpholino-ethanamine, or morpholine.) in the presence of coupling reagent (representative examples include, but are not limited to, N,N'-dicyclohexylcarbodiimide, N,N'-diisopropylcarbodiimide, or 1-ethyl-3-(3-dimethylaminopropyl) carbodiimide hydrochloride.), and appropriate solvent or without solvent to give a compound of formula IX-3. This amide formation reaction can be performed in the presence of appropriate additives (representative examples include, but are not limited to, 1-hydroxybenzotriazole, or N-hydroxysuccinimide).

Preparation Method X

A compound of formula X-5 and X-6 may be prepared from a compound of formula IV-1.

(triphenylphosphine)palladium(0), [1,1'-bis(diphenylphosphino)ferrocene]palladium(II) dichloride, palladium carbon, dichlorobis(triphenylphosphine)nickel(II), or bis(triphenylphosphine)palladium(II) dichloride.), alkali metal carbonate (representative examples include, but are not limited to, potassium carbonate, sodium carbonate, or cesium carbonate) or other alkali metal salt (sodium hydroxide, potassium hydroxide, dodium ethoxide, sodium methoxide, sodium tert-butoxide, potassium tert-butoxide, sodium hydride, sodium phosphate, potassium phosphate), and appropriate solvent or without solvent to give a compound of formula X-2.

A compound of formula X-2 can further react in the presence of transition metal catalyst (representative examples include, but are not limited to, palladium carbon, platinum carbon or rhodium carbon.), and appropriate solvent or without solvent under hydrogen atmosphere to give a compound of formula X-3. The reaction can be performed in any hydrogen pressure which depends on reagent and target material. However, preferable pressure is between 1 to 10 atm, and even more preferably between 1 to 5 atm.

A compound of formula X-3 can react with a compound of formula X-4 in the presence of reducing reagent (representative examples include, but are not limited to, sodium triac-

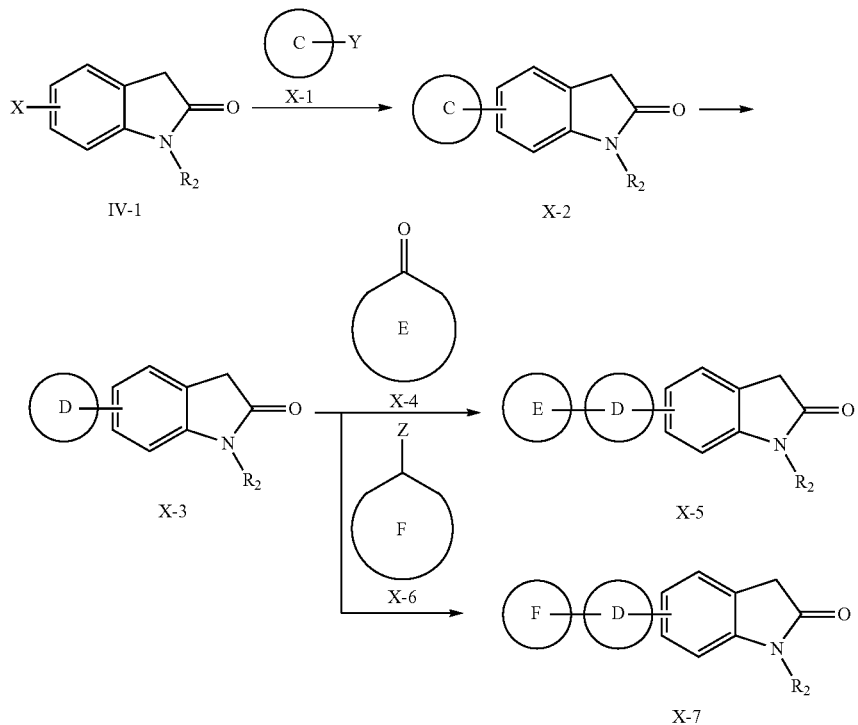

etoxyborohydride, tetramethyl triacetoxyborohydride, picolyl borane, or sodium cyanoborohydride.), acid (representative examples include, but are not limited to acetic acid, or trifluoroacetic acid), and appropriate solvent or without solvent to give a compound of formula X-5.

A compound of formula X-3 can react with a compound of formula X-6 (wherein Z is leaving group representative examples include, but are not limited to, chloro, bromo, iodo, trifluoromethanesulfonyl, or p-tosyl) in the presence of tertiary amine (representative examples include, but are not

[In the scheme, $R_2$, X and Y are same as the above definition. C is optionally substituted heteroalicyclic group (said heteroalicyclic group is unsaturated, and one of double bond is attached to X or Y). D is optionally substituted heteroalicyclic group (wherein heteroalicyclic group is saturated.). E is optionally substituted hetero alicyclic. F is optionally substituted heteroaryl or optionally substituted hetero alicyclic group.]

A compound of formula IV-1 can react with a compound of formula X-1 in the presence of transition metal catalyst (representative examples include, but are not limited to, tetrakis limited to, diisopyropylethylamine, triethylamine, or pyridine), and appropriate solvent or without solvent to give a compound of formula X-7.

Preparation Method XI

A compound of formula X-2 may be prepared from a compound of formula II-2.

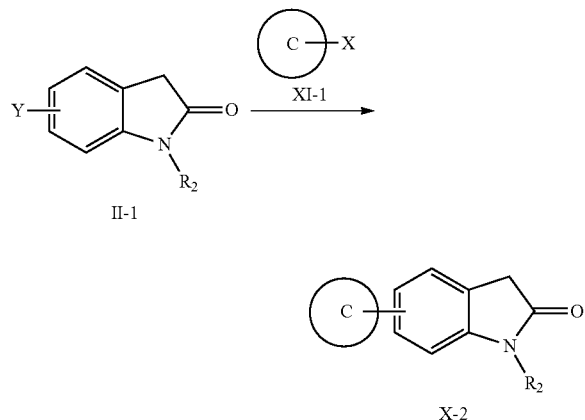

[In the scheme, the symbols have the same meaning as defined above.]

A compound of formula II-1 can react with a compound of formula XI-1 in the presence of transition metal catalyst (representative examples include, but are not limited to, tetrakis(triphenylphosphine)palladium(0), [1,1'-bis(diphenylphosphino)ferrocene]palladium(II) dichloride, palladium carbon, dichlorobis(triphenylphosphine)nickel(II) or bis(triphenylphosphine)palladium(II) dichloride.), alkali metal carbonate (potassium carbonate, sodium carbonate, or cesium carbonate) or other alkali metal salt (sodium hydroxide, potassium hydroxide, dodium ethoxide, sodium methoxide, sodium tert-butoxide, potassium tert-butoxide, sodium hydride, sodium phosphate, potassium phosphate), and appropriate solvent or without solvent to give a compound of formula X-2.

Preparation Method XII

A compound of formula XII-4 may be prepared from a compound of formula XII-1.

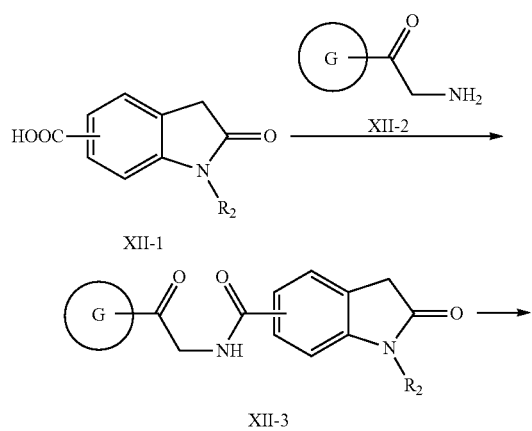

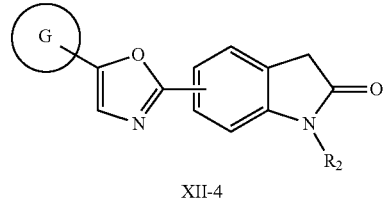

[In the scheme, $R_2$ is same as the above definition. G is defined as $R_{8a}$ or $R_{9a}$.]

A compound of formula XII-1 can react with a compound of formula XII-2 in the presence of coupling reagent (representative examples include, but are not limited to, N,N'-dicyclohexylcarbodiimide, N,N'-diisopropylcarbodiimide, or 1-ethyl-3-(3-dimethylaminopropyl.), primary or secondary amine (representative examples include, but are not limited to, 2-amino-1-phenylethanone, 2-amino-1-p-tolylethanone, 2-amino-1-(4-chlorophenyl)ethanone, 2-amino-1-(4-methoxyphenyl)ethanone, or 2-amino-1-(pyridin-4-yl)ethanone.), and appropriate solvent or without solvent to give a compound of formula XII-3. This amide formation reaction can be performed in the presence of appropriate additives (representative examples include, but are not limited to, 1-hydroxybenzotriazole, or N-hydroxysuccinimide.).

A compound of formula XII-3 can further react in the presence of acid (representative examples include, but are not limited to, trifluoroacetic acid, methanesulfonic acid, p-toluenesulfonic acid, benzenesulfonic acid, or sulfuric acid) to give a compound of formula XII-4.

Preparation Method XIII

A compound of formula XIII-6 may be prepared from a compound of formula XIII-1.

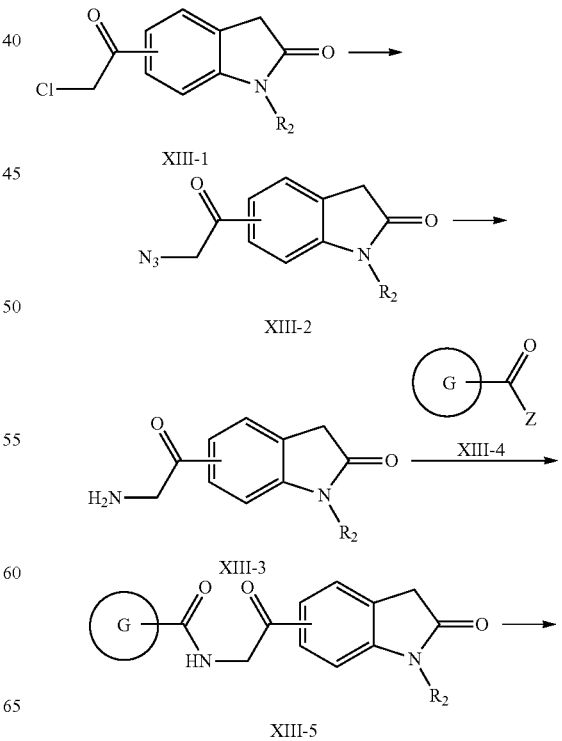

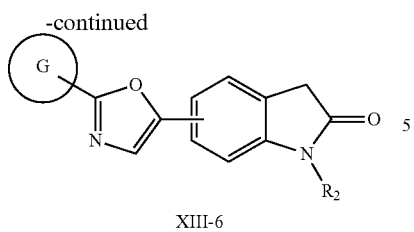

XIII-6

[In the scheme, the symbols have the same meaning as defined above.]

A compound of formula XIII-1 can react with azide salt (representative examples include, but are not limited to, sodium azide.), and appropriate solvent or without solvent to give a compound of formula XIII-2. This reaction can be preformed in the presence of additive (representative examples include, but are not limited to, potassium iodide, or tetrabutylammonium iodide).

A compound of formula XIII-2 can further react in the presence of metal catalyst (representative examples include, but are not limited to, palladium carbon, or platinum carbon.), and appropriate solvent or without solvent under hydrogen atmosphere to give a compound of formula XIII-3. The reaction can be performed in any hydrogen pressure which depends on reagent and target material. However, preferable pressure is between 1 to 10 atm, and even more preferably between 1 to 5 atm.

A compound of formula XIII-3 can further react with a compound of formula XIII-4 (wherein "Z" is defined as leaving group such as Cl, Br and the likes. Representative examples include, but are not limited to, benzoyl chloride, benzoyl bromide, 4-chlorobenzoyl chloride, 4-methoxybenzoyl chloride, 4-methylbenzoyl chloride, isonicotinoyl chloride, nicotinoyl chloride, picolinoyl chloride, or tetrahydro-2H-pyran-4-carbonyl chloride.), and appropriate solvent or without solvent to give a compound of formula XIII-5. This reaction can be preformed in the presence of additive (representative examples include, but are not limited to, diisopropylethylamine, pyridine, or triethylamine.).

A compound of formula XIII-5 can further react in the presence of acids (representative examples include, but are not limited to, trifluoroacetic acid, methanesulfonic acid, p-toluenesulfonic acid, benzenesulfonic acid, or sulfuric acid.), and appropriate solvent or without solvent to give a compound of formula XIII-6.

Preparation Method XIV

A compound of formula XIV-4 may be prepared from a compound of formula XIV-1.

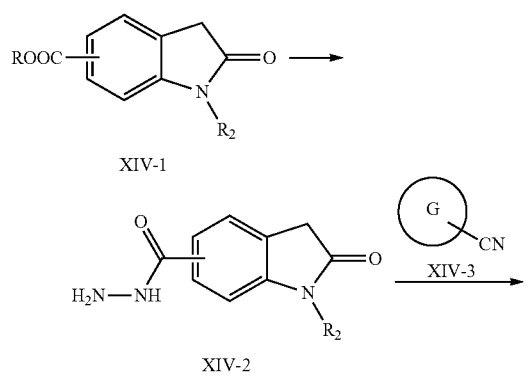

XIV-1

XIV-2

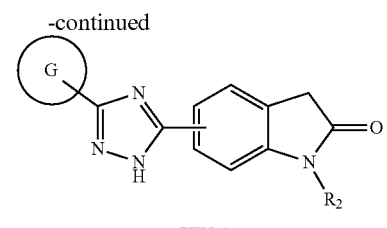

XIV-4

[In the scheme, R is alkyl. The symbols have the same meaning as defined above.]

A compound of formula XIV-1 can react with hydrazine (representative examples include, but are not limited to, hydrazine hydrate, or hydrazine) in the presence of solvent or without solvent to give a compound of formula XIV-2.

A compound of formula XIV-2 can react with aryl nitrile (representative examples include, but are not limited to, benzonitrile, 4-methylbenzonitrile, 4-chlorobenzonitrile, 4-methoxybenzonitrile, 3-methylbenzonitrile, isonicotinonitrile, or tetrahydro-2H-pyran-4-carbonitrile.) in the presence of alkali metal carbonate (representative examples include, but are not limited to, potassium carbonate, sodium carbonate, or cesium carbonate.) and appropriate solvent or without solvent to give a compound of formula XIV-4.

Preparation Method XV

A compound of formula XV-2 may be prepared from a compound of formula XIII-1.

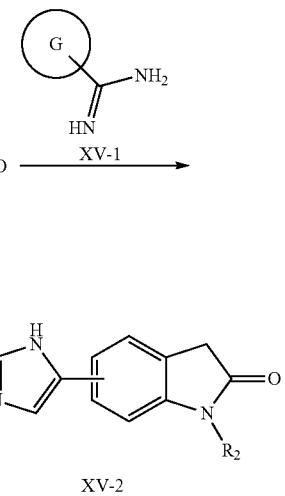

XIII-1

XV-2

[In the scheme, the symbols have the same meaning as defined above.]

A compound of formula XIII-1 can react with a compound of formula XV-1 (representative examples include, but are not limited to, benzimidamide, substituted benzimidamide, or isonicotinimidamide.), and appropriate solvent or without solvent to give a compound of formula XV-2. This reaction can be preformed in the presence of additive (representative examples include, but are not limited to, sodium iodide or potassium iodide.).

Preparation Method XVI

A compound of formula XVI-2 may be prepared from a compound of formula XIII-1.

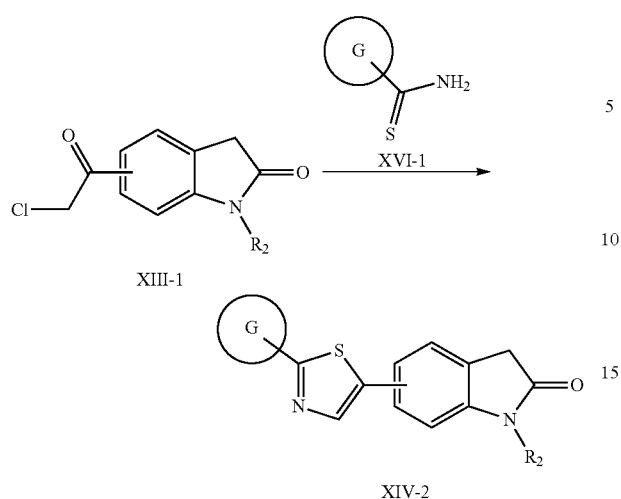

XIII-1

XIV-2

[In the scheme, the symbols have the same meaning as defined above.]

A compound of formula XIII-1 can react with a compound of formula XVI-1 (representative examples include, but are not limited to, benzothioamide, 4-methylbenzothioamide, 4-chlorobenzothioamide, 4-methoxybenzothioamide, 3-methylbenzothioamide, pyridine-4-carbothioamide, pyridine-3-carbothioamide, pyridine-2-carbothioamide or tert-butyl 4-carbamothioylpiperidine-1-carboxylate.), and appropriate solvent or without solvent to give a compound of formula XVI-2.

Preparation Method XVII

A compound of formula XVII-3 may be prepared from a compound of formula IV-1.

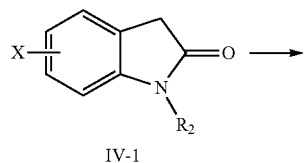

IV-1

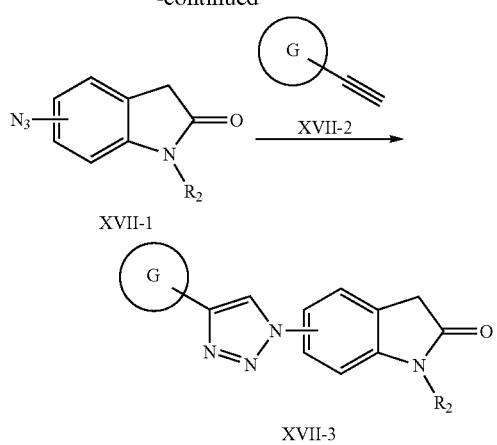

XVII-1

XVII-3

[In the scheme, the symbols have the same meaning as defined above.]

A compound of formula IV-1 can react with azide salt (representative examples include, but are not limited to, sodium azide, or hydrogen azide.) and a compound of formula XVII-2 (representative examples include, but are not limited to, phenyl acetylene, 1-ethynyl-4-methylbenzene, 4-chloro-1-ethynyl-benzene, or 4-ethynylpyridine.) in the presence of alkali base carbonate (representative examples include, but are not limited to, sodium carbonate, potassium carbonate, or cesium carbonate.), copper salt (representative examples include, but are not limited to, copper chloride (I), copper bromide (I), or copper iodide (I).), ascorbate (representative examples include, but are not limited to, sodium ascorbate, or potassium ascorbate.), amine (representative examples include, but are not limited to, N,N'-dimethylethylenediamine) and appropriate solvent or without solvent to give a compound of formula XVII-3.

Sodium Ascorbate

Preparation Method XVIII

A compound of formula XVIII-4 and XVIII-6 may be prepared from a compound of formula IV-1.

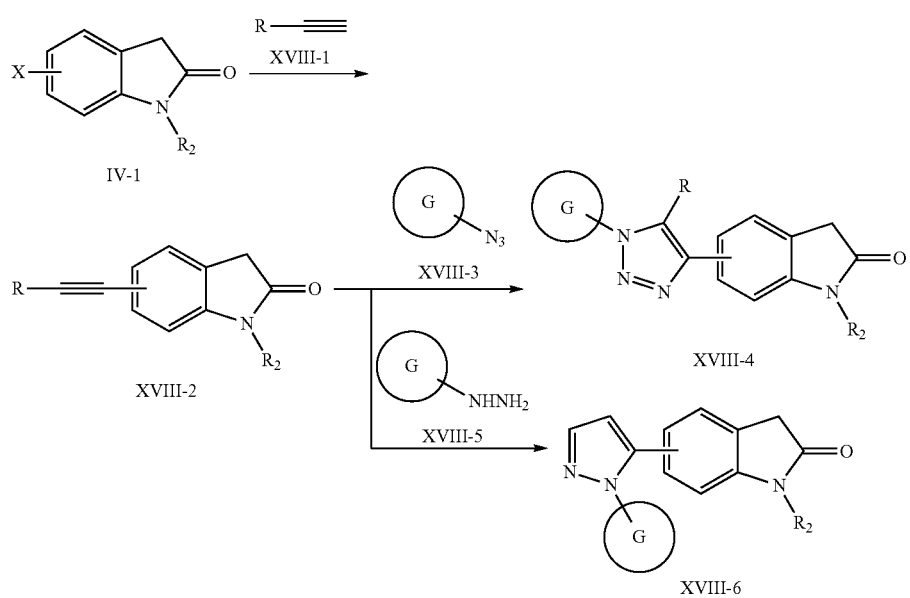

[In the scheme, the symbols have the same meaning as defined above.]

A compound of formula IV-1 (wherein R is alkyl, or trialkyl silyl) can react with a compound of formula XVIII-1 (representative examples include, but are not limited to, phenylacetylene, prop-1-yne, or 3,3-diethoxyprop-1-yne.) in the presence of transition metal catalyst (representative examples include, but are not limited to, tetrakis(triphenylphosphine) palladium(0), [1,1'-bis(diphenylphosphino)ferrocene]palladium(II) dichloride, or bis(triphenylphosphine)palladium(II) dichloride.), copper catalyst (representative examples include, but are not limited to, copper chloride (I), copper bromide (I), or copper iodide (I).), organic base (representative examples include, but are not limited to, diisopropylethyamine, or triethylamine.), and appropriate solvent or without solvent to give a compound of formula XVIII-2.

A compound of formula XVIII-2 can further react with a compound of formula XVIII-3 (representative examples include, but are not limited to, phenylazide, 1-azido-4-methylbenzene, 1-azido-4-chlorobenzene, or 4-azidopyridine.) in the presence of copper catalyst (representative examples include, but are not limited to, copper chloride (I), copper bromide (I), or copper iodide (I).), alkali metal carbonate (representative examples include, but are not limited to, sodium carbonate, potassium carbonate, or cesium carbonate.), amine (representative examples include, but are not limited to, N,N'-dimethylethylenediamine.) and appropriate solvent or without solvent to give a compound of formula XVIII-4.

A compound of formula XVIII-2 (wherein R contains ketone, aldehyde or their equivalent (representative examples include, but are not limited to, 5-(3,3-diethoxyprop-1-ynyl) indolin-2-one, or 5-(3,3-diethoxybut-1-ynyl)indolin-2-one.) next to triple bond) can react with a compound of formula XVIII-5 (representative examples include, but are not limited to, phenylhydrazine, p-tolylhydrazine, or p-cyanophenylhydrazine.) in the presence of appropriate solvent or without solvent to give a compound of formula XVIII-6. This reaction can be performed in the presence of acid (representative examples include, but are not limited to, sulfuric acid, p-toluenesulfonyl acid, or methanesulfonyl acid.).

The present invention encompasses a compound of formula (1) or a prodrug thereof, or a pharmaceutically acceptable salt thereof. It also encompasses a solvate thereof such as a hydrate or an ethanolate, etc. Further, the present invention encompasses every tautomer, every existing stereoisomer and every crystalline form of the compound of the present invention (1).

The term "prodrug of a compound of formula (1)" herein means a compound which is converted to a compound of formula (1) by reaction(s) by enzyme or gastric acid, etc. under the physiological condition in vivo, e.g. a compound which is converted to a compound of formula (1) by enzymatic oxidization, reduction, hydrolysis, etc.; a compound which is converted to a compound of formula (1) by hydrolysis by gastric acid, etc.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethane sulfonates, fumarates, glucoheptonoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides {e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Solvates of the compounds of the invention are also contemplated herein. Solvates of the compounds of the present invention include, for example, hydrates.

Compounds of the present invention, and salts thereof, may exist in their tautomeric form (for example, as an amide or imino ether). All such tautomeric forms are contemplated herein as part of the present invention.

The compounds of the present invention may form salts which are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. "Pharmaceutically acceptable salts" (i.e., non-toxic, physiologically acceptable) are preferred, although other salts are also useful, e.g., in isolation or purification steps which may be employed during preparation. Salts of the compounds of the present invention may be formed, for example, by reacting a compound I, II or III with an amount of acid or base, such as an equivalent amount, in a medium such as one in which the salt precipitates or in an aqueous medium followed by lyophilization.

All stereoisomers of the compounds of the present invention (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the present invention are, subsequent to their preparation, preferably isolated and purified to obtain a composition containing an amount by weight equal to or greater than 95% ("substantially pure" compound I), which is then used or formulated as described herein. In certain embodiments, the compounds of the present invention are more than 99% pure.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

The present invention also provides, in part, a method of treating, preventing or ameliorating a protein kinase related disorder in a mammal, comprising administering to the mammal in need thereof a therapeutically effective amount of a pharmaceutical composition comprising a compound of the present invention as described hereinabove. The mammal may be in need of the treatment or the treatment may be administered prophylactically for prevention or for amelioration of the protein kinase related disorder.

A "protein kinase related disorder" is any disease or deleterious condition in which a protein kinase plays a role. Examples include a serine-threonine kinase related disorder, a receptor tyrosine kinase related disorder, a non-receptor tyrosine kinase related disorder, an EGFR related disorder, an IGFR related disorder, a PDGFR related disorder and a flk related disorder. The compounds of the present invention may be used for any of these protein kinase related disorders.

In certain embodiments, the protein kinase related disorder is a cancer such as lung cancer, bladder cancer, head and neck cancer, melanoma, ovarian cancer, prostate cancer, breast cancer, small-cell lung cancer, glioma, colorectal cancer, non-small cell lung cancer, genitourinary cancer, pancreatic cancer, thyroid cancer, Hodgkin's lymphoma, non-Hodgkin's lymphoma, gastrointestinal cancer, gastric cancer, hepatoma, gastrointestinal stromal tumor, squamous cell carcinoma, renal cell carcinoma, astrocytoma, Kaposi's sarcoma, chronic myelogenous leukemia, acute myelogenous leukemia, myeloproliferative disorders, and glioblastoma.

According to one or more embodiments of the present invention, "cancer stem cell" ("CSC") or "cancer stem cells" ("CSCs") refer to a minute population of cancer cells that have self-renewal capability and are tumorigenic. They are also called "Cancer Initiating Cells", "Tumor Initiating Cells", "Cancer Stem-Like Cells", "Stem-Like Cancer Cells", "aggressive cancer cells", and "super malignant cancer cells", etc. The methods of isolating these cells include but not limited to enrichment by their ability of efflux Hoechst 33342, enrichment of surface markers such as CD133, CD44, and others, and enrichment by their tumorigenic property.

The term "CSCPK" or "CSCPKs" refer to protein kinase(s) that are essential for cancer stem cell survival or self-renewal.

In certain embodiments, the protein kinase is CSCPK. The compounds of the present invention are particularly useful for the treatment, prevention or amelioration of cancer, such as lung cancer, bladder cancer, head and neck cancer, melanoma, ovarian cancer, prostate cancer, breast cancer, small-cell lung cancer, glioma, colorectal cancer, non-small-cell lung cancer, genitourinary cancer, pancreatic cancer, thyroid cancer, Hodgkin's lymphoma, non-Hodgkin's lymphoma, gastrointestinal cancer, gastric cancer, hepatoma, gastrointestinal stromal tumor, squamous cell carcinoma, renal cell carcinoma, astrocytoma, Kaposi's sarcoma, chronic myelogenous leukemia, acute myelogenous leukemia, myeloproliferative disorders, and glioblastoma, by inhibiting CSCPKs.

In yet other embodiments, the protein kinase includes serine-threonine kinases, receptor tyrosine kinases and non-receptor tyrosine kinases.

In yet other embodiments, the protein kinase related disorder includes diabetes, an autoimmune disorder, a hyperproliferation disorder, angiogenesis, an inflammatory disorder, an immunological disorder, a cardiovascular disorder, restenosis, fibrosis, psoriasis, von Heppel-Lindau disease, osteoarthritis, neurodegeneration, infection, and rheumatoid arthritis.

The present invention provides, in part, a method of inhibiting/reducing/diminishing cancer stem cell survival and/or proliferation, self-renewal in a mammal by inhibiting or decreasing unwanted activity of several kinases including CSCPK.

The present invention also provides, in part, a method of inhibiting cancer stem cell niche, or stromal cell signaling by targeting CSCPKs.

The present invention further provides, in part, a method of treating cancer, inhibiting/reducing/diminishing cancer stem cell survival and/or proliferation.

The present invention also provides, in part, a method of modulating the catalytic activity of a protein kinase. The method comprises contacting said protein kinase with a compound of the present invention, or a pharmaceutically-acceptable salt thereof. In certain embodiments, the protein kinase includes a serine-threonine kinase, a receptor tyrosine kinase and a non-receptor tyrosine kinase.

The present invention also provides, in part, a pharmaceutical composition comprising a compound of the present invention as described hereinabove, or an enantiomer, diastereomer, tautomer, or pharmaceutically acceptable salt, solvate or prodrugs thereof, and a pharmaceutically-acceptable excipient, carrier, or diluent.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the mammal being treated and the particular mode of administration. The amount of active ingredient, which can be combined with a carrier material to produce a single dosage form, will generally be that amount of the compound which produces a therapeutic effect. Generally, out of 100%, this amount will range, for example, from about 0.1% to about 25% of active ingredient. [1] Therapeutic compositions or formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the alcohol or inhibitor according to the invention is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polypropylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of the compounds of the invention include pharmaceutically acceptable emulsions, micro-emulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, for example, hydroxypropyl-beta-cyclodextrin, may be used to solubilize compounds.

Besides inert diluents, the oral compositions can also include adjuvants such as wetting agents, emulsifying and suspending agents, sweetening, flavoring, coloring, perfuming and preservative agents. Suspensions, in addition to the alcohols or inhibitors according to the invention, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more alcohols or inhibitors according to the invention, with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention. Formulations of the present invention which are suitable for vaginal administration also include pessaries, tampons, creams, gels, pastes, foams or spray formulations containing such carriers as are known in the art to be appropriate.

Dosage forms for the topical or transdermal administration of an alcohol or other inhibitor according to the invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an alcohol or other inhibitor according to the invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of this invention.

Pharmaceutical compositions of this invention suitable for parenteral administration comprise one or more alcohols or inhibitors according to the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of the alcohol or inhibitor according to the invention, it is desirable to slow the absorption of the alcohol or inhibitor from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered composition is accomplished by dissolving or suspending the alcohol or inhibitor in an oil vehicle. One strategy for depot injections includes the use of polyethylene oxide-polypropylene oxide copolymers wherein the vehicle is fluid at room temperature and solidifies at body temperature.

The pharmaceutical compounds of this invention may be administered alone, or simultaneously, subsequently or sequentially with one or more active agents, other pharmaceutical agents, or with other anti-cancer or cytotoxic agent as described hereinabove, as well as in combination with a pharmaceutically-acceptable excipient, carrier, or diluent as described above.

The amount of pharmacological agent in the oral unit dosage form, with as a single or multiple dosage, is an amount that is effective for treating a neurological disorder. As one of skill in the art will recognize, the precise dose to be employed will depend on a variety of factors, examples of which include the condition itself, the seriousness of the condition being treated, the particular composition used, as well as various physical factors related to the individual being treated. In vitro or in vivo assays can optionally be employed to help identify optimal dosage ranges.

The compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compounds of the invention or a pharmaceutically acceptable salt thereof calculated as the free base, the compound being administered 1 to 4 times per day. Suitably the compounds will be administered for a period of continuous therapy, for example for a week or more.

EXAMPLES

The following preparations and examples are given to enable those skilled in the art to more clearly understand and to practice the present invention. They should not be considered as limiting the scope of the invention, but merely as being illustrative and representative thereof.

The synthesized compounds are identified by NMR, LCMS, IR, melting point, HPLC and so on.

The abbreviations used in NMR spectrums are following: s for singlet, d for doublet, t for triplet, m for multiplet, br for broad, brs for broad singlet, and J for binding constant.

Reference Example 1

Production of 5-(5-phenylthiophen-2-yl)indolin-2-one

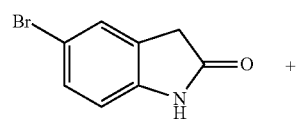

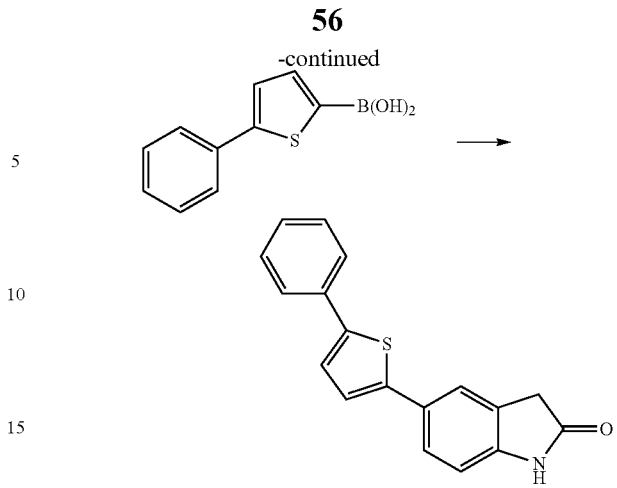

To a solution of 5-bromooxindole (100 mg, 0.572 mmol) in dioxane/$H_2O$ (3 ml/1 ml) was added $Pd(PPh_3)_4$ (55 mg, 0.047 mmol), 5-phenylthiophene-2-boronic acid (106 mg, 0.519 mmol) and potassium carbonate (196 mg, 1.42 mmol). The mixture was stirred at 120° C. for 1 hour under microwave irradiation. The residue was extracted with $CHCl_3$, and the organic layer was washed with $H_2O$ and brine, dried over $Na_2SO_4$ and concentrated in vacuo. The residue was purified by column chromatography ($CHCl_3$/MeOH) to give 5-(5-phenylthiophen-2-yl)indolin-2-one (44 mg) as a pale yellow solid.

MS m/z 292.4 (M+H).

Reference Examples 2 to 8

Reactions and treatments were carried out in the same manner as Reference example 1 using the corresponding starting material compounds, thereby giving the compounds of Reference example 2 to 8 shown in Table 1.

TABLE 1

| Reference Example | structure | Spectral data |
| --- | --- | --- |
| 2 | 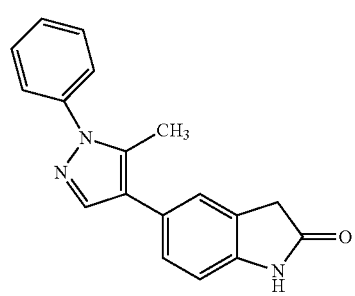 [SMILES: Cc1c(-c2ccc3c(c2)CC(=O)N3)cnn1-c1ccccc1] | LCMS m/z 290.3 (M + H) |
| 3 | 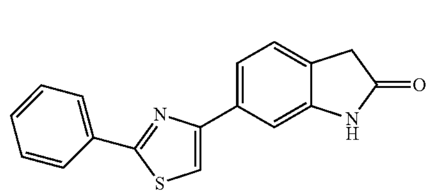 [SMILES: O=C1Cc2ccc(-c3csc(-c4ccccc4)n3)cc2N1] | 300 MHz $^1$H-NMR (DMSO-$d_6$, δ) 10.48 (s, 1H), 8.12 (s, 1H), 8.03-7.98 (m, 2H), 7.65-7.49 (m, 5H), 7.29 (d, 1H, J = 7.7 Hz), 3.52 (s, 2H) |

TABLE 1-continued

| Reference Example | structure | Spectral data |
|---|---|---|
| 4 | 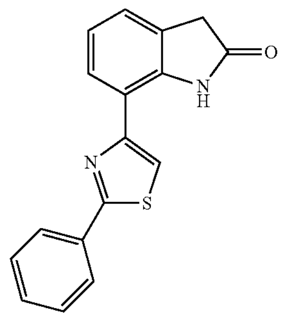 [SMILES: O=C1Cc2cccc(-c3csc(-c4ccccc4)n3)c2N1] | 300 MHz $^1$H-NMR (DMSO-$d_6$, δ) 9.97 (s, 1H), 8.20 (s, 1H), 8.06-8.00 (m, 2H), 7.75 (d, 1H, J = 7.5 Hz), 7.61-7.50 (m, 3H), 7.25 (d, 1H, J = 7.2 Hz), 7.06 (dd, 1H, J = 7.2, 7.5 Hz), 3.60 (s, 2H) |
| 5 | 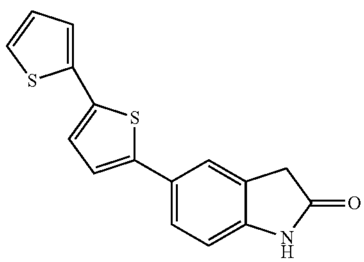 [SMILES: O=C1Cc2cc(-c3ccc(-c4cccs4)s3)ccc2N1] | LCMS m/z 298.2 (M + H) |
| 6 | 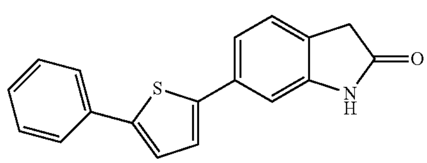 [SMILES: O=C1Cc2ccc(-c3ccc(-c4ccccc4)s3)cc2N1] | LCMS m/z 292.4 (M + H) |
| 7 | 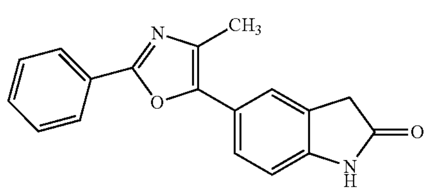 [SMILES: Cc1nc(-c2ccccc2)oc1-c1ccc2c(c1)CC(=O)N2] | LCMS m/z 291.3 (M + H) |
| 8 | 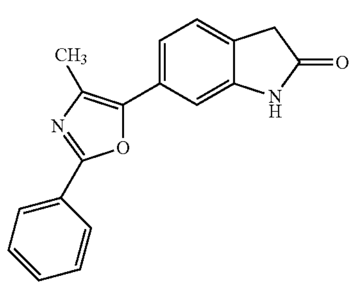 [SMILES: Cc1nc(-c2ccccc2)oc1-c1ccc2c(c1)NC(=O)C2] | LCMS m/z 291.3 (M + H) |

Reference Example 9

Production of
5-(5-phenyl-1,3,4-thiadiazol-2-yl)indolin-2-one

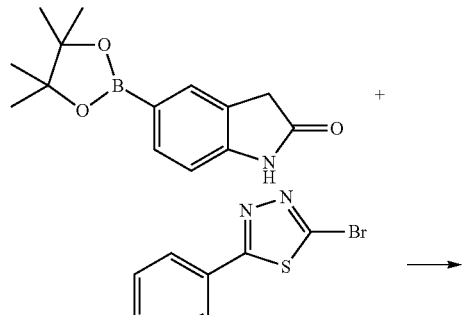

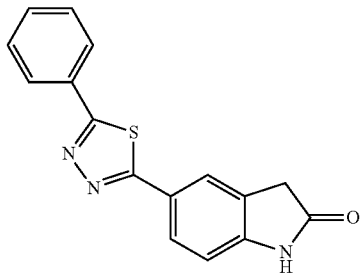

To a solution of 5-(4,4,5,5-tetramethyl-1,3,2-dioxaborolan-2-yl)indolin-2-one (98 mg, 0.38 mmol) in dioxane (0.76 ml) was added $PdCl_2$(dppf) $CH_2Cl_2$ (28 mg, 0.039 mmol), 2-bromo-5-phenyl-1,3,4-thiadiazole (138 mg, 0.57 mmol) and 2 M potassium carbonate (aq, 568 µL). The mixture was stirred at 90° C. for 4 hour. The residue was extracted with EtOAc, and the organic layer was washed with $H_2O$ and brine, dried over $Na_2SO_4$, and concentrated in vacuo. The residue was purified by column chromatography (n-hexane/EtOAc) to give 5-(5-phenyl-1,3,4-thiadiazol-2-yl)indolin-2-one (28 mg) as brown oil.

LCMS m/z 294.3 (M+H)

Reference Examples 10 to 14

Reactions and treatments were carried out in the same manner as Reference example 9 using the corresponding starting material compounds, thereby giving the compounds of Reference example 10 to 12 shown in Table 2.

TABLE 2

| Reference Example | structure | Spectral data |
|---|---|---|
| 10 | (phenyl-pyrazole-oxindole structure) | LCMS m/z 276.3 (M + H) |
| 11 | (pyridyl-thiophene-oxindole structure) | LCMS m/z 293.2 (M + H) |

TABLE 2-continued

| Reference Example | structure | Spectral data |
|---|---|---|
| 12 | 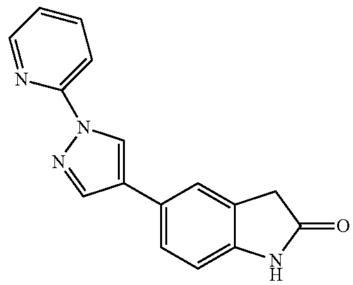 [SMILES: O=C1Cc2cc(-c3cnn(-c4ccccn4)c3)ccc2N1] | LCMS m/z 277.3 (M + H) |
| 13 | 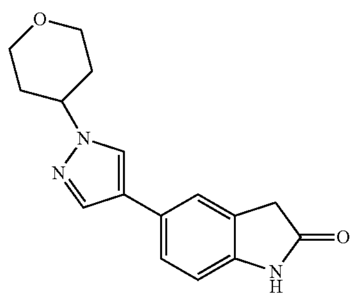 [SMILES: O=C1Cc2cc(-c3cnn(C4CCOCC4)c3)ccc2N1] | 300 MHz $^1$H-NMR (CDCl$_3$, δ) 7.61 (s, 1H), 7.46 (s, 1H), 4.40-4.30 (m, 1H), 4.33-4.09 (m, 2H), 3.50 (d, 2H, J = 2.4, 8.8 Hz), 2.11-1.93 (m, 2H). |
| 14 | 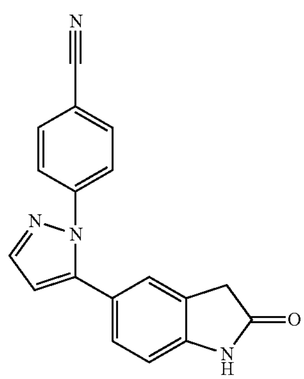 [SMILES: N#Cc1ccc(-n2nccc2-c2ccc3c(c2)CC(=O)N3)cc1] | 400 MHz $^1$H-NMR (CDCl$_3$, δ) 8.58 (brs, 1H), 7.78 (d, 1H, J = 1.8 Hz), 7.65 (dd, 2H, J = 1.9, 6.8 Hz), 7.47 (dd, 2H, J = 1.9, 6.8 Hz), 7.16 (s, 1H), 7.09 (dd, 1H, J = 1.6, 8.1 Hz), 6.88 (d, 1H, J = 1.6, 8.1 Hz), 6.50 (d, 1H, J = 1.8 Hz), 3.56 (s, 2H). |

Reference Example 15

Production of 5-(5-phenyloxazol-2-yl)indolin-2-one

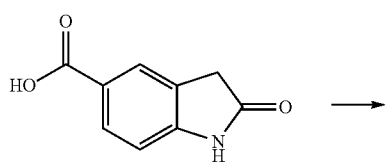

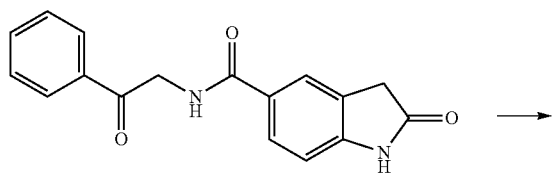

-continued

To a solution of 2-oxoindoline-5-carboxylic acid (1.3 g, 7.3 mmol) in DMF (50 ml) was added iPr$_2$NEt (3.8 ml, 22 mmol), HOBt (1.2 g, 8.8 mmol), WSCI (1.7 g, 8.8 mmol) and 2-amino-1-phenylethanone hydrochloride (1.3 g, 7.3 mmol). The reaction mixture was stirred for 2 h at room temperature. The mixture was poured into H$_2$O and EtOAc. The resulting precipitate was removed by filtration, and the filtrate was separated. The organic layer was washed with sat. NaHCO$_3$ solution, sat. NH$_4$Cl solution and brine, and then dried over Na$_2$SO$_4$. The solvent was evaporated and the residue (0.73 g)

was used for the next reaction without further purification. Sulfuric acid (5 ml) was added to the residue, and the mixture was heated for 2 h at 100° C. Ice was added, and the mixture was extracted with EtOAc. The organic layer was washed with $H_2O$ and brine, dried over $Na_2SO_4$ and evaporated. The residue was crystallized from EtOH to afford 5-(5-phenyloxazol-2-yl)indolin-2-one (0.27 g, 13%).

$^1$H NMR (300 MHz, DMSO-$d_6$) δ 10.68 (s, 1H), 7.96-7.91 (m, 2H), 7.84-7.80 (m, 2H), 7.77 (s, 1H), 7.52-7.47 (m, 2H), 7.37 (m, 1H), 6.97 (d, 1H, J=8.0 Hz), 3.60 (s, 2H).

Reference Example 16

Production of 5-(2-phenyloxazol-5-yl)indolin-2-one

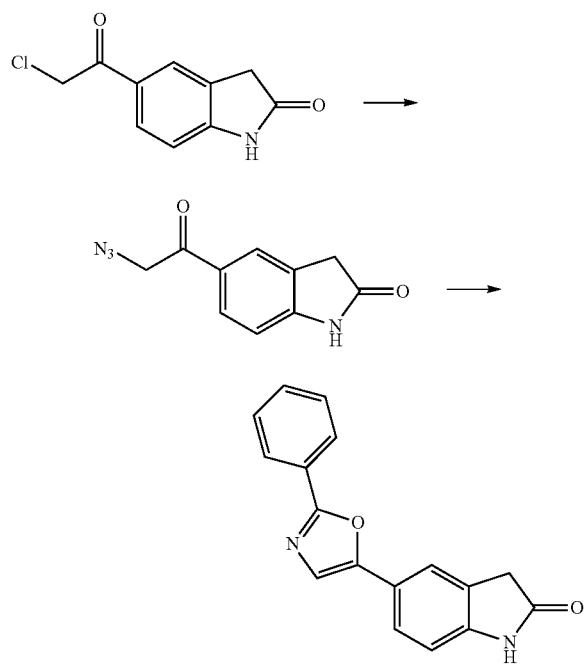

To a solution of 5-(2-chloroacetyl)indolin-2-one (1.0 g, 4.8 mmol) in DMF (20 ml) was added NaI (0.14 g, 0.96 mmol) and $NaN_3$ (0.37 g, 5.7 mmol), and the mixture was stirred for 2 h at room temperature. $H_2O$ and EtOAc were added to the mixture, and the resulting precipitate was filtered and dried to afford 5-(2-azidoacetyl)indolin-2-one (0.38 g, 37%).

$^1$H NMR (300 MHz, DMSO-$d_6$) δ 10.77 (s, 1H), 7.84 (dd, 1H, J=8.2, 1.6 Hz), 7.79 (d, 1H, J=1.6 Hz), 6.93 (d, 1H, J=8.2 Hz), 4.80 (s, 2H), 3.57 (s, 2H).

To a solution of 5-(2-azidoacetyl)indolin-2-one (0.20 g, 1.1 mmol) in DMF (5 ml) was added 10% Pd—C (0.20 g), and the mixture was stirred for 3.5 h at room temperature under $H_2$ atmosphere. The mixture was passed through Celite. To the filtrate was added benzoyl chloride (0.12 ml, 1.1 mmol) and iPr$_2$NEt (0.36 ml, 2.2 mmol), and the reaction mixture was stirred for 1 h at 0° C. $H_2O$ and EtOAc were added to the mixture, and insoluble solid was removed by filtration. The filtrate was separated and the organic layer was washed with $H_2O$ and brine, dried over $Na_2SO_4$ and evaporated. The residue was dissolved in sulfuric acid (2.0 ml) and the mixture was heated for 2 h at 90° C. The mixture was cooled to room temperature, and $H_2O$ was added. The mixture was extracted with EtOAc, washed with $H_2O$ and brine, dried over $Na_2SO_4$ and evaporated. Purification by column chromatography (EtOAc/hex) gave 5-(2-phenyloxazol-5-yl)indolin-2-one (0.07 g, 24%).

$^1$H NMR (400 MHz, DMSO-$d_6$) δ 10.58 (s, 1H), 8.08-8.05 (m, 2H), 7.72-7.65 (m, 3H), 7.58-7.50 (m, 3H), 6.92 (d, 1H, J=8.1 Hz), 3.57 (s, 2H).

Reference Example 17

Production of 5-(3-phenyl-1H-1,2,4-triazol-5-yl)indolin-2-one

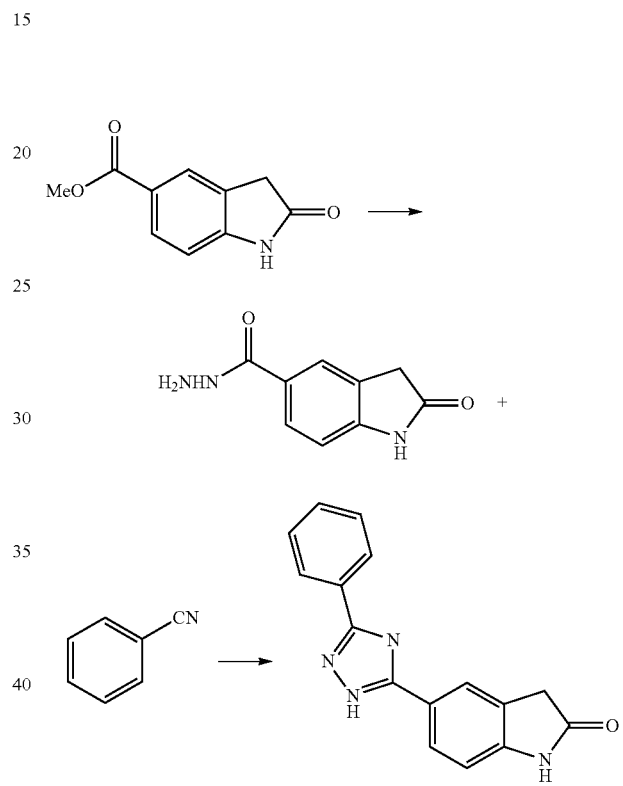

To a solution of methyl 2-oxoindoline-5-carboxylate (0.40 g, 4.8 mmol) in EtOH (8 ml) was added hydrazine monohydrate (2 ml), and the mixture was stirred for 6 h at 80° C. The mixture was cooled to room temperature, and the resulting precipitate was filtered and dried to afford 2-oxoindoline-5-carbohydrazide (0.25 g, 63%).

$^1$H NMR (400 MHz, DMSO-$d_6$) δ 9.58 (s, 1H), 7.71-7.67 (m, 2H), 6.83 (d, 1H, J=8.0 Hz), 4.41 (br, 2H), 3.51 (s, 2H).

To a solution of 2-oxoindoline-5-carbohydrazide (200 mg, 1.05 mmol) in n-BuOH/DMF (6 ml/2 ml) was added benzonitrile (324 mg, 3.14 mmol) and potassium carbonate (29 mg, 0.21 mmol). The mixture was heated at 150° C. for 3 hours under microwave irradiation. CHCl$_3$/MeOH (20 ml/1 ml) was added to the mixture and insoluble solid was removed by filtration. The filtrate was concentrated. $H_2O$ was added to the residue and extracted with CHCl$_3$. The organic layer was dried over $Na_2SO_4$ and concentrated in vacuo. Purification by column chromatography (CHCl$_3$/MeOH) gave 5-(3-phenyl-1H-1,2,4-triazol-5-yl)indolin-2-one (15 mg).

LCMS m/z 277.3 (M+H)

Reference Example 18

Production of 5-(2-phenyl-1H-imidazol-5-yl)indolin-2-one

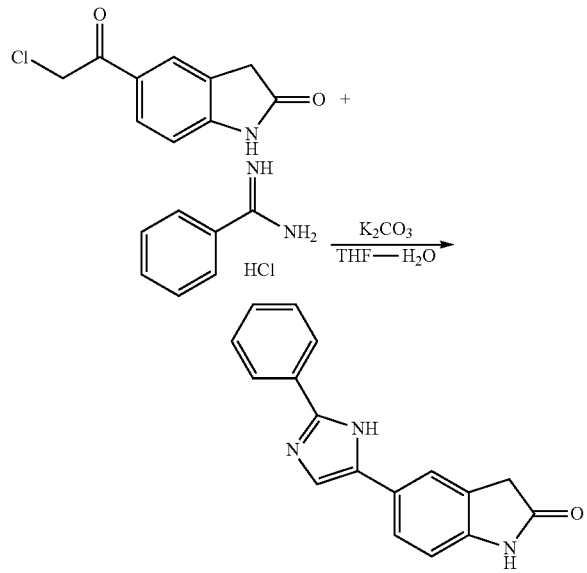

To a solution of 5-(2-chloroacetyl)indolin-2-one (100 mg, 0.477 mmol) in THF/H$_2$O (3 ml/1 ml) was added benzimidamide hydrochloride (75 mg, 0.477 mmol) and potassium carbonate (198 mg, 1.43 mmol). The mixture was stirred for 7 hours under reflux. The mixture was extracted with CHCl$_3$, and the organic layer washed with H$_2$O, dried over Na$_2$SO$_4$ and concentrated in vacuo. The residue purified by column chromatography (CHCl$_3$/MeOH) to give 5-(3-phenyl-1H-imidazol-5-yl)indolin-2-one (19 mg).
LCMS m/z 276.30 (M+H)

Reference Example 19

Production of 5-(4-phenyl-1H-1,2,3-triazol-1-yl) indolin-2-one

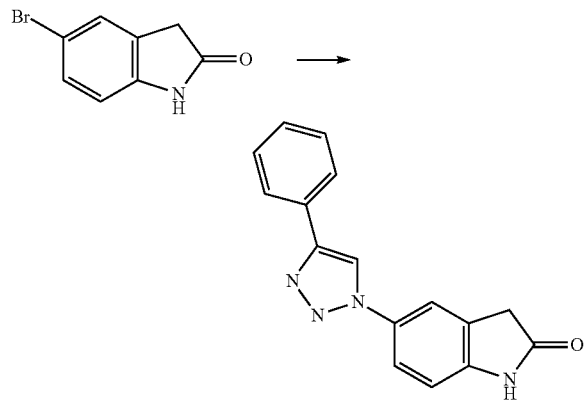

The mixture of 5-bromoindolin-2-one (530 mg, 2.5 mmol), N,N'-dimethylethylenediamine (44 mg, 0.5 mmol), ethynyl-benzene (274 μl, 2.5 mmol), CuI (48 mg, 0.25 mmol), sodium azide (325 mg, 5 mmol) and sodium ascorbate (99 mg, 0.5 mmol) in EtOH (7 ml), H$_2$O (3 ml) was heated to 80° C. for 18 h. All reagents were re-added and heated to 80° C. for 10 h. After confirming the reaction complete, reaction mixture was cooled to room temperature and EtOH was removed under reduced pressure. 20 ml of water was added and filtered. The filtrate was washed with water and hexane and dried under vacuo to give 5-(4-phenyl-1H-1,2,3-triazol-1-yl)indolin-2-one (450 mg).

Reference Example 20

Production of 5-(1-phenyl-1H-1,2,3-triazol-4-yl) indolin-2-one

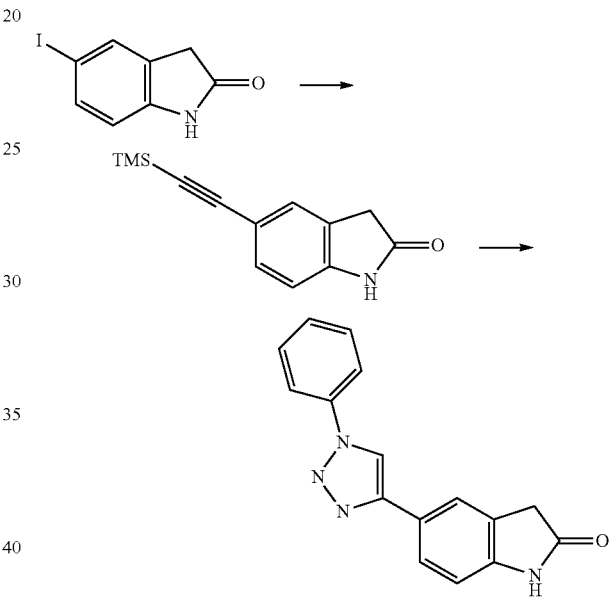

To a solution of 5-iodoindolin-2-one (518 mg, 2 mmol), TEA (3 ml) and CuI (38 mg) in DMF (3 ml) was added to PdCl$_2$(PPh$_3$)$_2$ (70 mg). The mixture was cooled to 0° C. and a solution of TMS-acetylene (1 ml). The mixture was maintained same temperature for 3 h, then warmed to rt. After stirring for overnight, the reaction mixture was concentrated in vacuo. The residue was purified by silica gel column chromatography to give 5-((trimethylsilyl)ethynyl)indolin-2-one (451 mg).

7.37-7.34 (2H, m), 6.80 (1H, d, J=9.0 Hz), 3.51 (2H, s), and 0.24 (9H, s).

To a mixture of iodobenzene (204 mg, 1 mmol), sodium azide (130 mg, 2 mmol), sodium carbonate (53 mg, 0.5 mmol), CuI (19 mg, 0.1 mmol), sodium ascorbate (20 mg) and N,N'-dimethylethylenediamine (18 ul, 0.2 mmol) in EtOH (1.5 ml) and water (0.5 ml) were added 5-((trimethylsilyl)ethynyl)indolin-2-one (115 mg, 0.5 mmol), and stirred at 80° C. for 2 h. After cooling to ambient temp, EtOH was removed under reduced pressure. The residue was suspended in EtOH and stirred for 1 h at rt and filtered. The filtrate was washed with water and hexane and dried under vacuo to give 5-(1-phenyl-1H-1,2,3-triazol-4-yl)indolin-2-one (106 mg).

Reference Example 21

Production of
5-(1-phenyl-1H-pyrazol-5-yl)indolin-2-one

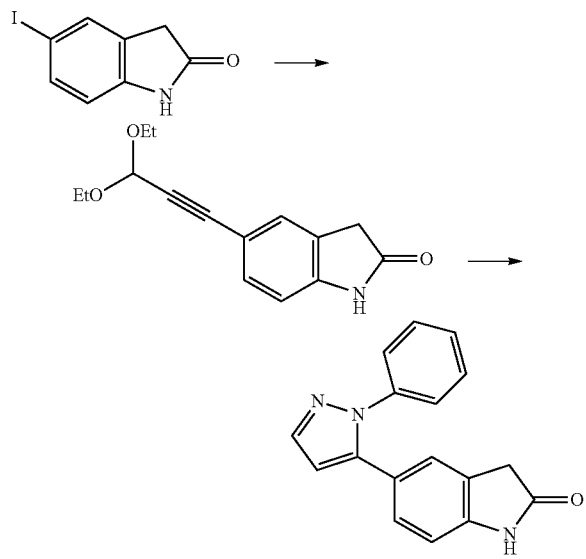

To a solution of 5-iodo-2-oxoindoline (497 mg, 1.9 mmol) in THF (20 ml) were added triethylamine (0.80 ml, 5.7 mmol), 3,3-diethoxyprop-1-yne (738 mg, 5.7 mmol), CuI (73 mg, 0.38 mmol) and Pd(PPh$_3$)$_4$ (222 mg, 0.19 mmol). The reaction mixture was stirred for 4 h at 50° C. The mixture was poured into H$_2$O and EtOAc. The mixture was separated into an aqueous layer and an organic layer. The aqueous layer was extracted with ethyl acetate 3 times. The combined organic layer was washed with sat. NaHCO$_3$ solution, and brine, and then dried over Na$_2$SO$_4$. The solvent was evaporated and the residue purified by column chromatography (EtOAc then CHCl$_3$/MeOH) to give 5-(3,3-diethoxyprop-1-ynyl)indolin-2-one as a brown solid (292 mg, 59%).

$^1$H NMR (400 MHz, DMSO-d$_6$) δ 7.73 (s, 1H), 7.19 (d, 1H, J=8.0 Hz), 7.16 (s, 1H), 6.63 (d, 1H, J=8.0 Hz), 5.31 (s, 1H), 3.64 (dq, 2H, J=9.4, 7.1 Hz), 3.48 (dq, 2H, J=9.4, 7.1 Hz), 3.34 (s, 2H), 1.10 (t, 6H, J=7.1 Hz).

To a solution of 5-(3,3-diethoxyprop-1-ynyl)indolin-2-one (100 mg, 0.39 mmol) in acetonitrile (5 ml) were added phenyl hydrazine (38 µL, 0.38 mmol) and sulfuric acid (52 µL, 0.98 mmol), and the mixture was stirred for 3 h at room temperature, then the mixture was stirred for 2 h at 50° C. The reaction mixture was poured into water (50 mL), and the resulting precipitate was filtered and dried. The precipitated was dissolved in acetonitrile (5 mL), then water (52 µL, 3.9 mmol) and sulfuric acid (93 µL, 1.75 mmol) were added. The mixture was heated at 80 C for 4 h. The mixture was cooled to room temperature, and then neutralized with sat. NaHCO$_3$. The mixture was extracted with CHCl$_3$/EtOAc 3 times. The combined organic extracts were washed with sat. NaCl, dried over Na$_2$SO$_4$, and evaporated in vacuo. The residue purified by column chromatography (EtOAc/n-hexane) to give the title compound as a brown solid (44 mg, 41%).

$^1$H NMR (400 MHz, CDCl$_3$) δ 8.28 (brs, 1H), 7.73 (d, 1H, J=1.8 Hz), 7.39-7.28 (m, 5H), 7.13-7.08 (m, 2H), 6.81 (d, 1H, J=8.0 Hz), 6.48 (d, 1H, J=1.8 Hz), 3.51 (s, 2H).

MS m/z 276.3 (M+H)

Reference Example 22

Production of 5-(1-(tetrahydro-2H-pyran-4-yl)piperidin-4-yl)indolin-2-one

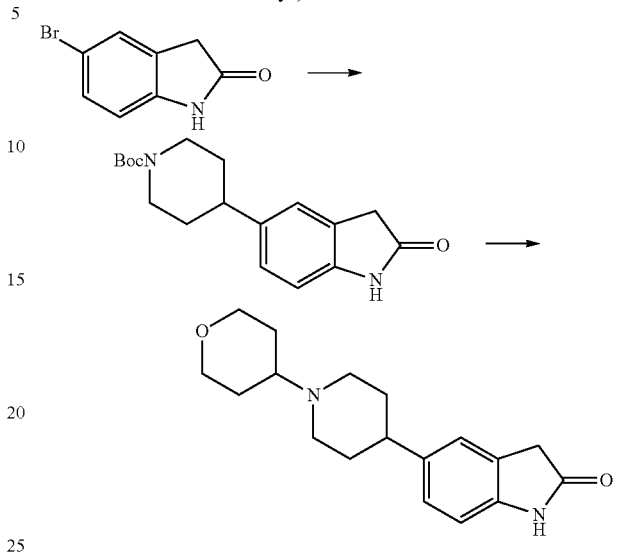

To a suspension of 5-bromoindolin-2-one (600 mg, 2.83 mmol) in 1,4-Dioxane (9 ml) and H$_2$O (3 ml) were added tert-butyl 4-(4,4,5,5-tetramethyl-1,3,2-dioxaborolan-2-yl)-5,6-dihydropyridine-1(2H)-carboxylate (1.05 g, 3.40 mmol), Pd(PPh$_3$)$_4$ (164 mg, 0.142 mmol) and K$_2$CO$_3$ (1.17 g, 8.50 mmol). After stirring at 120° C. in microwave reactor for 1 h, the reaction mixture was diluted with sat. NaHCO$_3$ aq. and extracted with CHCl$_3$. The organic layer was dried over Na$_2$SO$_4$ and concentrated. The residue was purified by column chromatography (CHCl$_3$/MeOH) to give tert-butyl 4-(2-oxoindolin-5-yl)-5,6-dihydropyridine-1(2H)-carboxylate (912 mg) as mixture with triphenylphosphin oxide.

LCMS m/z 315 (M+H)

To a solution of tert-butyl 4-(2-oxoindolin-5-yl)-5,6-dihydropyridine-1(2H)-carboxylate (912 mg, 2.90 mmol) in THF (10 ml) and MeOH (10 ml) was added 10% Pd/C (453 mg) and stirred at room temperature under H$_2$ (1 atom) atmosphere for 7 h. The reaction mixture was filtered through a Celite pad and concentrated. The residue was purified by column chromatography (CHCl$_3$/MeOH) to afford tert-butyl 4-(2-oxoindolin-5-yl)piperidine-1-carboxylate (846 mg, 92%).

$^1$H NMR (300 MHz, DMSO-d$_6$) δ 10.25 (s, 1H), 7.65-7.49 (m, 1H), 7.07 (s, 1H), 7.00 (d, 1H, J=7.8 Hz), 6.71 (d, 1H, J=7.8 Hz), 4.10-3.96 (m, 2H), 3.41 (s, 2H), 2.86-2.66 (m, 2H), 2.66-2.50 (m, 1H), 1.75-1.62 (m, 2H), 1.51-1.30 (m, 2H), 1.40 (s, 9H).

To a solution of TFA (10 ml) was added tert-butyl 4-(2-oxoindolin-5-yl)piperidine-1-carboxylate (789 mg, 2.49 mmol) and stirred at room temperature for 30 min. The reaction mixture was concentrated. The residue was diluted with 1N HCl and extracted with CHCl$_3$. The aqueous layer was added with 28% NH$_3$ aq until pH 8 and extracted with CHCl$_3$/EtOH (3/1). The organic layer was dried over Na$_2$SO$_4$ and concentrated to give 5-(piperidin-4-yl)indolin-2-one (409 mg, 76%).

LCMS m/z 217 (M+H)

To a solution of 5-(piperidin-4-yl)indolin-2-one (64.6 mg, 0.299 mmol) in THF (1.5 ml) and MeOH (3 ml) were added dihydro-2H-pyran-4 (3H)-one (0.132 ml, 1.34 mmol), acetic acid (0.170 ml, 29.5 mmol) and NaBH$_3$(CN) (61.6 mg, 0.931 mmol). After stirring at room temperature for 4 days, the reaction mixture was concentrated. The residue was diluted with sat. NaHCO₃ aq. and extracted with CHCl₃. The organic layer was dried over Na₂SO₄ and concentrated. The residue was purified by column chromatography (CHCl₃/MeOH) to give 5-(1-(tetrahydro-2H-pyran-4-yl)piperidin-4-yl)indolin-2-one (84.9 mg, 95%).

¹H NMR (300 MHz, DMSO-d₆) δ 10.23 (s, 1H), 7.06 (s, 1H), 7.00 (d, 1H, J=7.9 Hz), 6.70 (d, 1H, J=7.9 Hz), 3.89-3.85 (m, 2H), 3.40 (s, 2H), 3.30-3.20 (m, 2H), 2.99-2.92 (m, 2H), 2.50-2.31 (m, 2H), 2.21-2.13 (m, 2H), 1.74-1.62 (m, 4H), 1.61-1.36 (m, 4H).

Reference Example 23

Reactions and treatments were carried out in the same manner as Reference example 22 using the corresponding starting material compounds, thereby giving the compounds of Reference example 23 shown in Table 3.

TABLE 3

| Reference Example | structure | Spectral data |
|---|---|---|
| 23 | 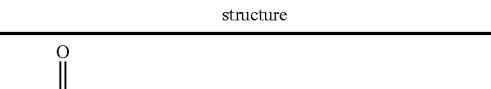 | 300 MHz ¹H-NMR (DMSO-d₆, δ) 10.24 (s, 1H), 7.06 (s, 1H), 7.00 (d, 1H, J = 8.1 Hz), 6.69 (d, 1H, J = 8.1 Hz), 4.42-4.34 (m, 1H), 3.91-3.77 (m, 2H), 3.72-3.56 (m, 2H), 3.40 (s, 2H), 3.16-3.07 (m, 1H), 3.01-2.86 (m, 4H), 2.45-2.30 (m, 1H), 2.27-2.16 (m, 2H), 1.96 (s, 3H), 1.79-1.45 (m, 3H), 1.45-1.13 (m, 2H). |

Reference Example 24

Production of 5-(1-(pyrimidin-2-yl)piperidin-4-yl) indolin-2-one

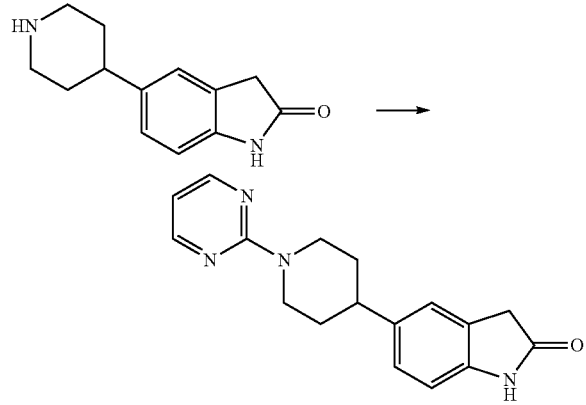

To a solution of 5-(piperidin-4-yl)indolin-2-one (39.8 mg, 0.184 mmol) in EtOH 3 ml) were added 2-chloropyrimidine (33.7 mg, 0.294 mmol) and iPr₂NEt (0.095 ml, 0.551 mmol). After stirring at 80° C. for 6 h, the reaction mixture was concentrated. The residue was purified by column chromatography (CHCl₃/MeOH) to give 5-(1-(pyrimidin-2-yl)piperidin-4-yl)indolin-2-one (47.9 mg, 88%).

¹H NMR (300 MHz, CDCl₃) δ 8.35 (s, 1H), 8.33 (s, 1H), 7.54 (brs, 1H), 7.08 (s, 1H), 7.04 (d, 1H, J=7.9 Hz), 6.77 (d, 1H, J=7.9 Hz), 6.58-6.47 (m, 1H), 4.99-4.90 (m, 2H), 3.49 (s, 2H), 3.03-2.91 (m, 2H), 2.81-2.69 (m, 1H), 1.98-1.88 (m, 2H), 1.73-1.50 (m, 2H).

Reference Example 25

Production of 5-(1-phenylpiperidin-4-yl)indolin-2-one

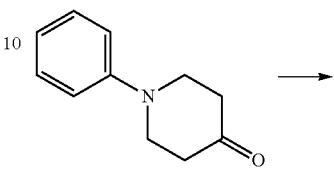

-continued

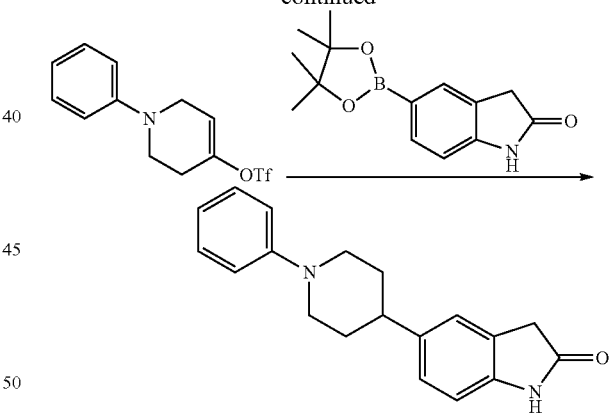

To a solution of LHMDS (3.2 ml, 1.10 M in hexane, 3.52 mmol) in THF (30 ml) was added a solution of 1-phenylpiperidin-4-one (559 mg, 3.19 mmol) in THF (7 ml) at −78° C. over 3 min. After stirring at the same temperature for 30 min, PhNTf₂ (1.48 g, 4.15 mmol) was added. After stirring at −78° C. for 20 min, then the reaction mixture was stirred at 0° C. for 20 min. The reaction mixture was quenched by sat. NH₄Cl aq. and extracted with CHCl₃. The organic layer was dried over Na₂SO₄ and concentrated. The residue was purified by column chromatography (hexane/EtOAc) to give 1-phenyl-1,2,3,6-tetrahydropyridin-4-yl trifluoromethanesulfonate (563 mg, 58%).

¹H NMR (300 MHz, CDCl₃) δ 7.32-7.24 (m, 2H), 6.97-6.87 (m, 3H), 5.90-5.86 (m, 1H), 3.87-3.82 (m, 2H), 3.50 (t, 2H, J=5.6 Hz), 2.62-2.56 (m, 2H).

To a solution of 1-phenyl-1,2,3,6-tetrahydropyridin-4-yl trifluoromethanesulfonate (104 mg, 0.339 mmol) in 1,4-Dioxane (3 ml) and H$_2$O (1 ml) were added 5-(4,4,5,5-tetramethyl-1,3,2-dioxaborolan-2-yl)indolin-2-one (97.6 mg, 0.377 mmol), Pd(PPh$_3$)$_4$ (38.8 mg, 0.00336 mmol), LiCl (47.1 mg, 1.11 mmol) and K$_2$CO$_3$ (140 mg, 1.01 mmol). After stirring at 120° C. in microwave reactor for 1 h, the reaction mixture was quenched by sat. NaHCO$_3$ aq. The resulting mixture was extracted with CHCl$_3$, the organic layer was washed with brine, dried over Na$_2$SO$_4$ and concentrated. The residue was purified by column chromatography (CHCl$_3$/MeOH) to give 5-(1-phenyl-1,2,3,6-tetrahydropyridin-4-yl)indolin-2-one (75.8 mg) as mixture of triphenylphosphine oxide.

MS m/z 291 (M+H)

To a solution of 5-(1-phenyl-1,2,3,6-tetrahydropyridin-4-yl)indolin-2-one (75.8 mg, 0.261 mmol) in THF (3 ml) and MeOH (3 ml) was added 10% Pd/C (210 mg) and stirred at room temperature under H$_2$ (1 atom) atmosphere for 2 h. The reaction mixture was filtered through a Celite pad and concentrated. The residue was purified by column chromatography (CHCl$_3$/MeOH) to afford 5-(1-phenylpiperidin-4-yl)indolin-2-one (51.2 mg) as mixture of triphenylphosphine oxide.

MS m/z 293 (M+H)

Reference Example 26

Production of (Z)—N-(2-(diethylamino)ethyl)-2,4-dimethyl-5-((2-oxo-5-(4,4,5,5-tetramethyl-1,3,2-dioxaborolan-2-yl)indolin-3-ylidene)methyl)-1H-pyrrole-3-carboxamide

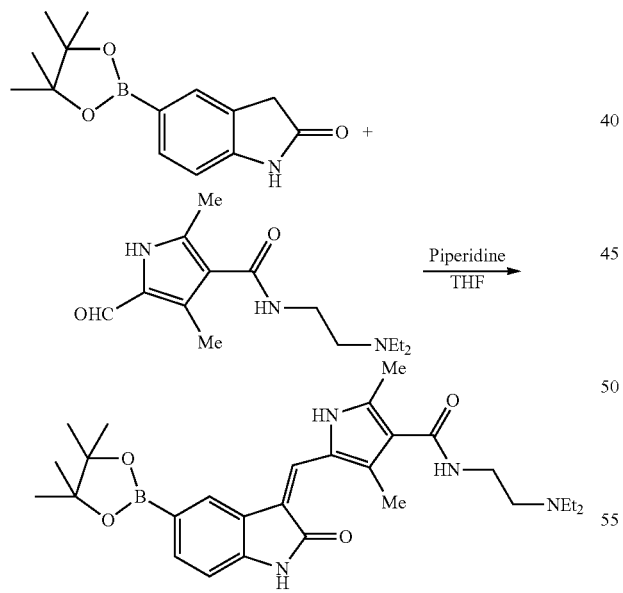

To a solution of 5-(4,4,5,5-tetramethyl-1,3,2-dioxaborolan-2-yl)indolin-2-one (195 mg, 0.75 mmol) in EtOH (3 ml) was added N-(2-(diethylamino)ethyl)-5-formyl-2,4-dimethyl-1H-pyrrole-3-carboxamide (200 mg, 0.76 mmol) and piperidine (82 μL, 0.83 mmol). The mixture was stirred at 80° C. for 1 hour. After cooled down to room temperature, the reaction mixture was concentrated, filtrated, and washed with EtOH to give (Z)—N-(2-(diethylamino)ethyl)-2,4-dimethyl-5-((2-oxo-5-(4,4,5,5-tetramethyl-1,3,2-dioxaborolan-2-yl)indolin-3-ylidene)methyl)-1H-pyrrole-3-carboxamide (218 mg) as yellow solid.

MS m/z 507.6 (M+H)

Reference Example 27

Production of (Z)-5-((5-bromo-2-oxoindolin-3-ylidene)methyl)-N-(2-(diethylamino)ethyl)-2,4-dimethyl-1H-pyrrole-3-carboxamide

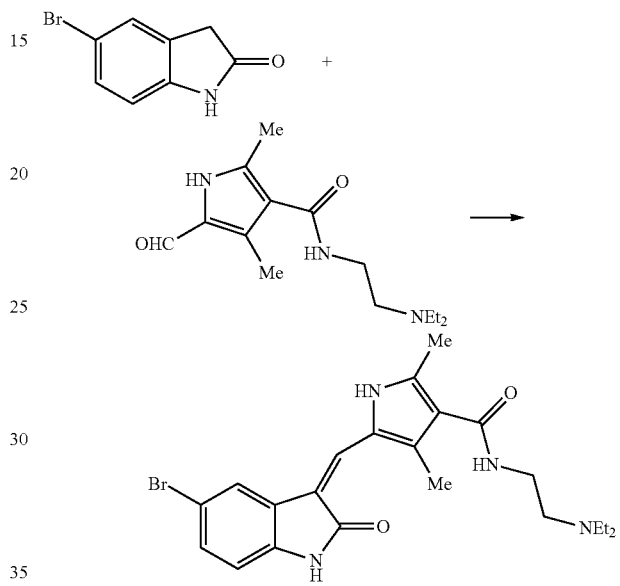

To the solution of 5-bromoindolin-2-one (262 mg, 1.24 mmol) in EtOH (5 ml) was added N-(2-(diethylamino)ethyl)-5-formyl-2,4-dimethyl-1H-pyrrole-3-carboxamide (298 mg, 1.12 mmol) and piperidine (112 μL, 1.13 mmol). The mixture was stirred at 80° C. for 1 hour. After cooled down to room temperature, the reaction mixture was concentrated, filtrated, and washed with EtOH to give (Z)-5-((5-bromo-2-oxoindolin-3-ylidene)methyl)-N-(2-(diethylamino)ethyl)-2,4-dimethyl-1H-pyrrole-3-carboxamide (368 mg) as orange solid.

MS m/z 459.4/461.4 (M+H)

Example 1

Production of (Z)—N-(2-(diethylamino)ethyl)-2,4-dimethyl-5-((2-oxo-5-(5-phenylthiophen-2-yl)indolin-3-ylidene)methyl)-1H-pyrrole-3-carboxamide

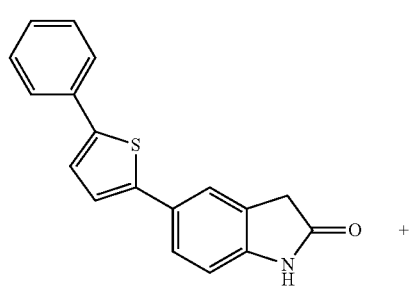

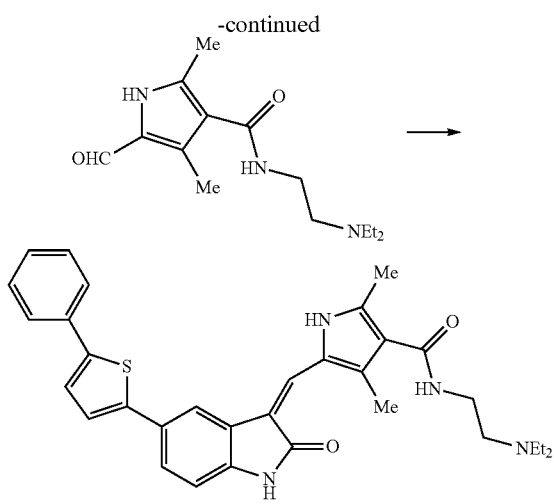

To a solution of No (23 mg, 0.079 mmol) in THF/EtOH (1 ml/1 ml) was added No (25.2 mg, 0.095 mmol) and piperidine (0.7 mg, 0.008 mmol). The mixture was stirred at 80° C. for 10 hours. After cooled down to the room temperature, the reaction mixture was concentrated, filtrated, and washed with EtOH to give (Z)—N-(2-(diethylamino)ethyl)-2,4-dimethyl-5-((2-oxo-5-(5-phenylthiophen-2-yl)indolin-3-ylidene)methyl)-1H-pyrrole-3-carboxamide (18 mg) as an orange solid.

$^1$H NMR (300 MHz, DMSO-$d_6$) δ 13.67 (s, 1H), 11.02 (s, 1H), 8.31 (s, 1H), 7.81 (s, 1H), 7.70-7.76 (m, 2H), 7.51 (s, 2H), 7.42-7.45 (m, 4H), 7.32-7.39 (m, 1H), 6.90-6.93 (m, 1H), 3.25-3.34 (m, 4H), 2.4-2.6 (m, 10H), 0.94-0.99 (m, 6H); MS m/z 539.70 (M+H).

Examples 2 to 50

Reactions and treatments were carried out in the same manner as in Example 1 using the corresponding starting material compounds, thereby giving the compounds of Examples 2 to 50 shown in Table 4.

TABLE 4

| Example | structure | Spectral data |
|---|---|---|
| 2 | 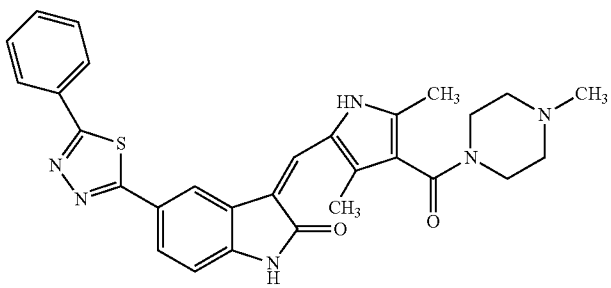 [SMILES: Cc1[nH]c(/C=C2\C(=O)Nc3ccc(-c4nnc(-c5ccccc5)s4)cc32)c(C)c1C(=O)N1CCN(C)CC1] | 300 MHz $^1$H-NMR (CDCl$_3$, δ) 13.29 (s, 1H), 8.48 (s, 1H), 8.19 (d, 1H), 7.99-7.96 (m, 1H), 7.66 (dd, 1H, J = 8.4, 1.8 Hz), 7.48-7.45 (m, 5H), 6.95 (d, 1H, J = 8.1 Hz), 3.74-3.47 (brs, 4H), 2.38-2.24 (m, 13H) |
| 3 | 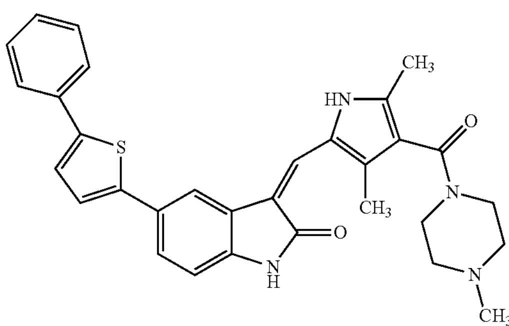 [SMILES: Cc1[nH]c(/C=C2\C(=O)Nc3ccc(-c4ccc(-c5ccccc5)s4)cc32)c(C)c1C(=O)N1CCN(C)CC1] | 300 MHz $^1$H-NMR (DMSO-$d_6$, δ) 13.62 (s, 1H), 11.02 (s, 1H), 8.17 (s, 1H), 7.80 (s, 1H), 7.70-7.68 (m, 2H), 7.55-7.51 (m, 2H), 7.45-7.41 (m, 3H), 7.32-7.29 (m, 1H), 6.94-6.92 (m, 1H), 3.47-3.42 (m, 4H), 2.49 (s, 3H), 2.32 (s, 3H), 2.30-2.27 (m, 4H), 2.19 (s, 3H) |
| 4 | 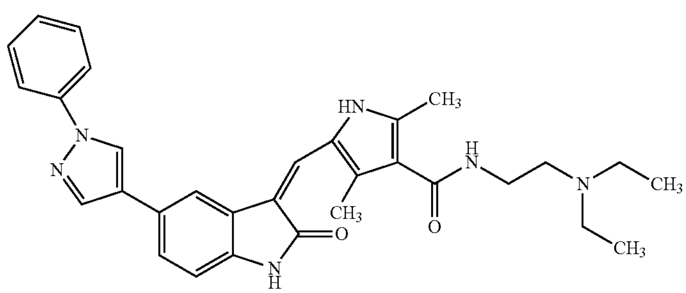 [SMILES: CCN(CC)CCNC(=O)c1c(C)[nH]c(/C=C2\C(=O)Nc3ccc(-c4cnn(-c5ccccc5)c4)cc32)c1C] | 300 MHz $^1$H-NMR (CDCl$_3$, δ) 13.29 (s, 1H), 8.53 (s, 1H), 7.67 (d, 2H, J = 8.4 Hz), 7.50 (s, 1H), 7.40 (t, 2H, J = 7.8 Hz), 7.30-7.23 (m, 3H), 6.83 (d, 1H, J = 7.8 Hz), 6.70 (brs, 1H), 3.48 (d, 2H, J = 5.4 Hz), 2.68-2.57 (m, 6H), 2.49 (s, 3H), 2.39 (s, 3H), 1.02 (t, 6H, J = 6.9 Hz) |

TABLE 4-continued

| Example | structure | Spectral data |
|---|---|---|
| 5 | 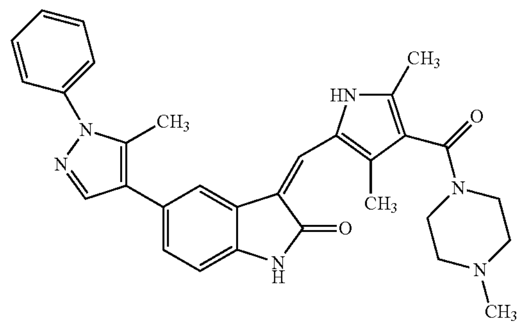 [SMILES: Cc1[nH]c(/C=C2\C(=O)Nc3ccc(-c4cnn(-c5ccccc5)c4C)cc32)c(C)c1C(=O)N1CCN(C)CC1] | 300 MHz ¹H-NMR (CDCl₃, δ) 13.63 (s, 1H), 8.14 (s, 1H), 7.78 (s, 1H), 7.45-7.42 (m, 4H), 7.40-7.36 (m, 2H), 7.24-7.17 (m, 2H), 6.95-6.92 (m, 1H), 3.74-3.72 (m, 4H), 2.63-2.56 (m, 4H), 2.42 (s, 3H), 2.38 (s, 3H), 2.32 (s, 3H), 2.30 (s, 3H) |
| 6 | 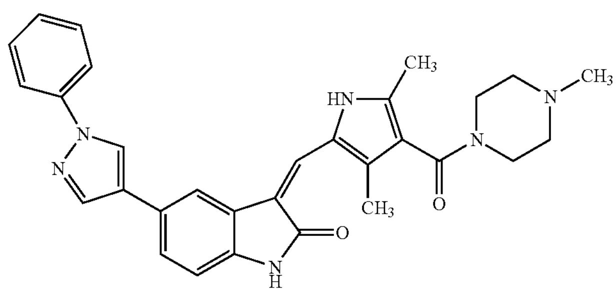 [SMILES: Cc1[nH]c(/C=C2\C(=O)Nc3ccc(-c4cnn(-c5ccccc5)c4)cc32)c(C)c1C(=O)N1CCN(C)CC1] | 300 MHz ¹H-NMR (CDCl₃, δ) 13.34 (s, 1H), 8.15 (s, 1H), 7.98 (s, 1H), 7.73 (d, 2H, J = 7.5 Hz), 7.60 (s, 1H), 7.46-7.41 (m, 3H), 7.32 (t, 2H, J = 7.5 Hz), 6.90 (d, 1H, J = 7.8 Hz), 3.69 (brs, 4H), 2.42-2.33 (m, 14H) |
| 7 | 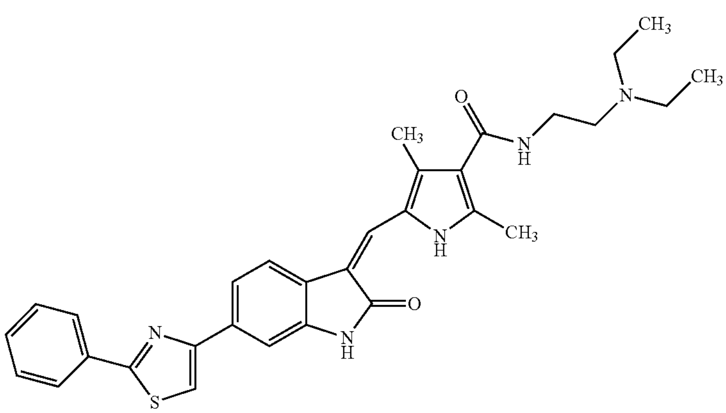 [SMILES: CCN(CC)CCNC(=O)c1c(C)[nH]c(/C=C2\C(=O)Nc3cc(-c4csc(-c5ccccc5)n4)ccc32)c1C] | 300 MHz ¹H-NMR (DMSO-d₆, δ) 13.63 (s, 1H), 11.01 (s, 1H), 8.15 (s, 1H), 8.05-8.00 (m, 2H), 7.87 (d, 1H, J = 8.1 Hz), 7.72-7.68 (m, 2H), 7.58-7.50 (m, 2H), 7.46-7.41 (m, 1H), 3.38-3.25 (m, 4H), 2.60-2.47 (m, 4H), 2.45 (s, 3H), 2.43 (s, 3H), 0.98 (t, 6H, J = 7.0 Hz) |
| 8 | 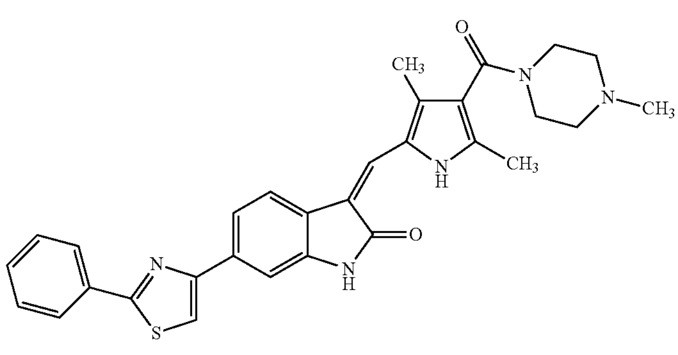 [SMILES: Cc1[nH]c(/C=C2\C(=O)Nc3cc(-c4csc(-c5ccccc5)n4)ccc32)c(C)c1C(=O)N1CCN(C)CC1] | 300 MHz ¹H-NMR (DMSO-d₆, δ) 13.57 (s, 1H), 11.01 (s, 1H), 8.15 (s, 1H), 8.04-8.00 (m, 2H), 7.86 (d, 1H, J = 8.1 Hz), 7.70 (dd, 1H, J = 1.5, 6.6 Hz), 7.66 (s, 1H), 7.58-7.51 (m, 5H), 3.55-3.35 (m, 4H), 2.37-2.23 (m, 4H), 2.29 (s, 3H), 2.27 (s, 3H), 2.18 (s, 3H) |

TABLE 4-continued
| Example | structure | Spectral data |
|---|---|---|
| 9 | 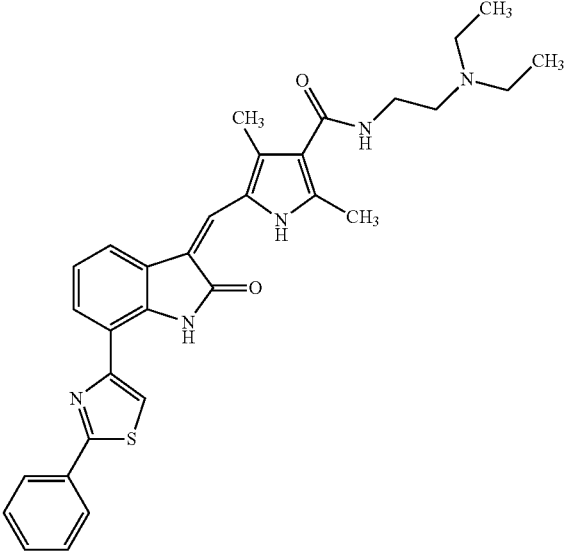 [SMILES: CCN(CC)CCNC(=O)c1c(C)[nH]c(/C=C2\C(=O)Nc3c2cccc3-c2csc(-c3ccccc3)n2)c1C] | 300 MHz $^1$H-NMR (DMSO-$d_6$, δ) 13.65 (s, 1H), 10.41 (s, 1H), 8.24 (s, 1H), 8.08-8.04 (m, 2H), 7.87 (d, 1H, J = 7.5 Hz), 7.75 (s, 1H), 7.72 (d, 1H, J = 8.3 Hz), 7.62-7.54 (m, 3H), 7.47-7.43 (m, 1H), 7.14 (dd, 1H, J = 7.7, 7.9 Hz), 3.36-3.23 (m, 4H), 2.56-2.45 (m, 4H), 2.46 (s, 3H), 2.44 (s, 3H), 0.97 (t, 6H, J = 7.1 Hz) |
| 10 | 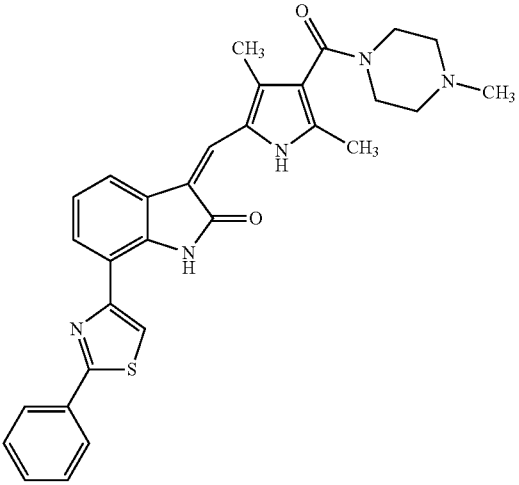 [SMILES: Cc1[nH]c(/C=C2\C(=O)Nc3c2cccc3-c2csc(-c3ccccc3)n2)c(C)c1C(=O)N1CCN(C)CC1] | 300 MHz $^1$H-NMR (DMSO-$d_6$, δ) 13.60 (s, 1H), 10.41 (s, 1H), 8.25 (s, 1H), 8.08-8.05 (m, 2H), 7.86 (d, 1H, J = 7.7 Hz), 7.73 (s. 1H), 7.71 (d, 1H, J = 8.8 Hz), 7.62-7.54 (m, 3H), 7.14 (t, 1H, J = 7.6 Hz), 3.57-3.37 (m, 4H), 2.32-2.25 (m, 4H), 2.30 (s, 3H), 2.28 (s, 3H), 2.18 (s, 3H) |
| 11 | 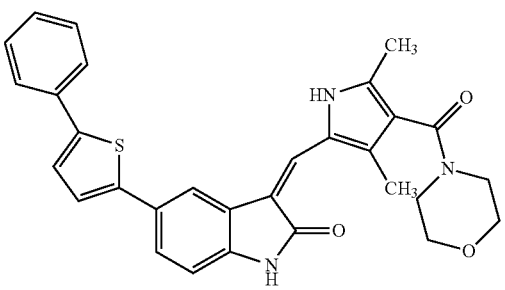 [SMILES: Cc1[nH]c(/C=C2\C(=O)Nc3ccc(-c4ccc(-c5ccccc5)s4)cc32)c(C)c1C(=O)N1CCOCC1] | 300 MHz $^1$H-NMR (DMSO-$d_6$, δ) 13.62 (s, 1H), 11.02 (s, 1H), 8.17 (s, 1H), 7.80 (s, 1H), 7.70-7.67 (m, 2H), 7.53-7.49 (m, 2H), 7.49-7.42 (m, 3H), 7.32-7.30 (m, 1H), 6.94-6.91 (m, 1H), 3.60-3.30 (m, 8H), 2.30 (s, 3H), 2.28 (s, 3H) |

TABLE 4-continued
| Example | structure | Spectral data |
|---|---|---|
| 12 | 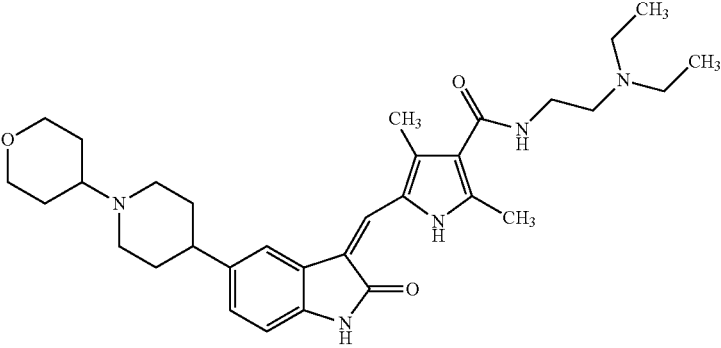 [SMILES: CCN(CC)CCNC(=O)c1c(C)[nH]c(/C=C2\C(=O)Nc3ccc(C4CCN(C5CCOCC5)CC4)cc32)c1C] | 300 MHz $^1$H-NMR (DMSO-d$_6$, δ) 13.66 (s, 1H), 10.77 (s, 1H), 7.75 (s, 1H), 7.67 (s, 1H), 7.38 (t, 1H, J = 5.5 Hz), 6.96 (brd, 1H, J = 7.9 Hz), 6.75 (d, 1H, J = 7.9 Hz), 3.92-3.85 (m, 2H), 3.34-3.22 (m, 6H), 3.03-2.97 (m, 2H), 2.57-2.39 (m, 6H), 2.42 (s, 3H), 2.42 (s, 3H), 2.23-2.12 (m 2H), 1.76-1.65 (m, 6H), 1.52-1.36 (m, 2H), 0.97 (t, 6H, J = 7.2 Hz) |
| 13 | 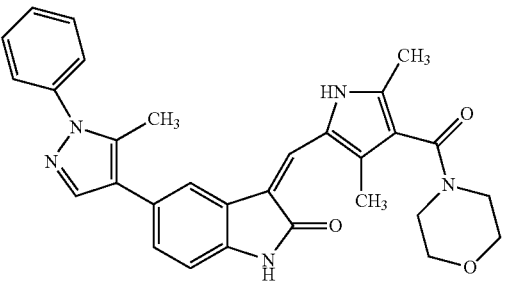 [SMILES: Cc1[nH]c(/C=C2\C(=O)Nc3ccc(-c4cnn(-c5ccccc5)c4C)cc32)c(C)c1C(=O)N1CCOCC1] | 300 MHz $^1$H-NMR (CDCl$_3$, δ) 13.35 (s, 1H), 8.14-8.11 (m, 1H), 7.74 (s, 1H), 7.51-7.45 (m, 4H), 7.42-7.38 (m, 2H), 7.29-7.21 (m, 2H), 6.96-6.90 (m, 1H), 3.80-3.40 (m, 8H), 2.43 (s, 3H), 2.40 (s, 3H), 2.24 (s, 3H) |
| 14 | 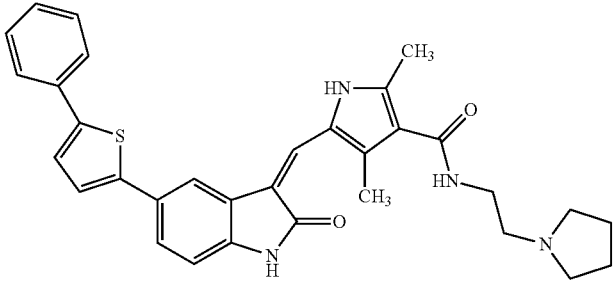 [SMILES: Cc1[nH]c(/C=C2\C(=O)Nc3ccc(-c4ccc(-c5ccccc5)s4)cc32)c(C)c1C(=O)NCCN1CCCC1] | 300 MHz $^1$H-NMR (DMSO-d$_6$, δ) 13.66 (s, 1H), 11.02 (s, 1H), 8.19 (s, 1H), 7.81 (s, 1H), 7.70-7.67 (m, 2H), 7.45-7.42 (m, 2H), 7.40-7.32 (m, 3H), 7.30-7.27 (m, 1H), 6.93-6.91 (m, 1H), 3.60-3.30 (m, 4H), 2.71-2.65 (m, 4H), 2.50 (s, 3H), 2.49 (s, 3H), 1.70-1.60 (m, 4H) |
| 15 | 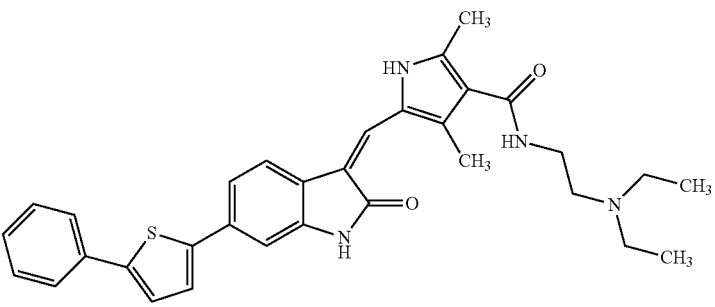 [SMILES: CCN(CC)CCNC(=O)c1c(C)[nH]c(/C=C2\C(=O)Nc3cc(-c4ccc(-c5ccccc5)s4)ccc32)c1C] | LCMS m/z 539.70 (M + H) |
| 16 | 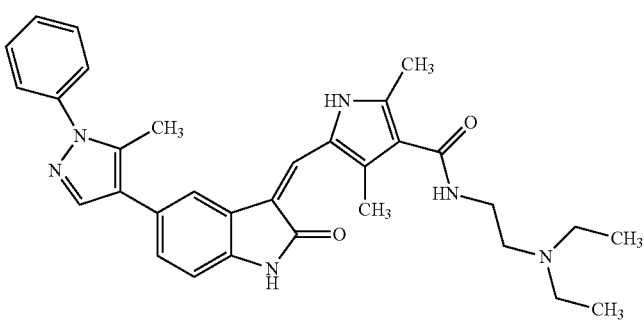 [SMILES: CCN(CC)CCNC(=O)c1c(C)[nH]c(/C=C2\C(=O)Nc3ccc(-c4cnn(-c5ccccc5)c4C)cc32)c1C] | 300 MHz $^1$H-NMR (CDCl$_3$, δ) 13.37 (s, 1H), 8.70 (s, 1H), 7.77 (s, 1H), 7.49-7.47 (m, 4H), 7.40-7.36 (m, 2H), 7.20-7.17 (m, 1H), 6.94-6.85 (m, 2H), 3.58-3.56 (m, 2H), 2.78-2.71 (m, 6H), 2.56 (s, 3H), 2.42 (s, 3H), 2.41 (s, 3H), 1.12-1.08 (m, 6H) |

TABLE 4-continued

| Example | structure | Spectral data |
|---|---|---|
| 17 | 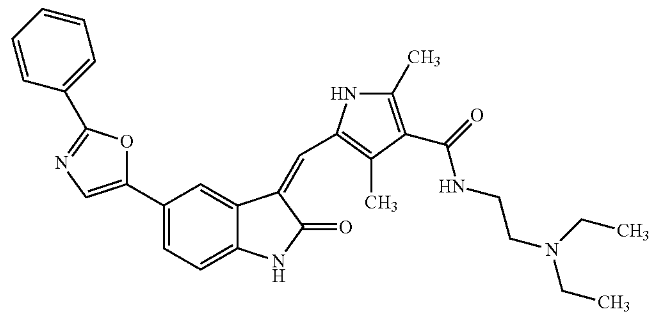 [SMILES: CCN(CC)CCNC(=O)c1c(C)[nH]c(/C=C2\C(=O)Nc3ccc(-c4ncc(-c5ccccc5)o4)cc32)c1C] | 400 MHz ¹H-NMR (DMSO-d$_6$, δ) 13.67 (s, 1H), 11.11 (br, 1H), 8.29 (d, 1H, J = 1.5 Hz), 8.15-8.10 (m, 2H), 7.83 (s, 1H), 7.73 (s, 1H), 7.65-7.43 (m, 5H), 7.00 (d, 1H, J = 8.1 Hz), 3.35-3.26 (m, 4H), 2.58-2.45 (m, 10H), 0.98 (t, 6H, J = 7.1 Hz) |
| 18 | 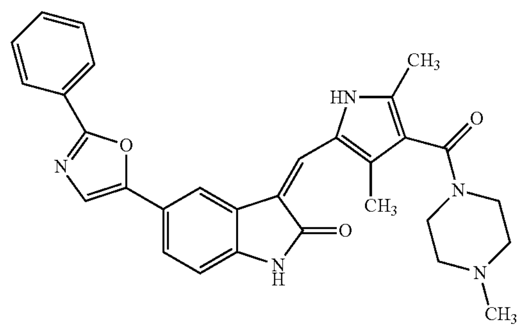 | 400 MHz ¹H-NMR (DMSO-d$_6$, δ) 13.61 (s, 1H), 11.10 (br, 1H), 7.81 (s, 1H), 7.73 (s, 1H), 7.65-7.51 (m, 4H), 7.00 (d, 1H, J = 8.1 Hz), 3.7-3.3 (m, 4H), 2.35-2.22 (m, 4H), 2.34 (s, 3H), 2.31 (s, 3H), 2.19 (s, 3H) |
| 19 | 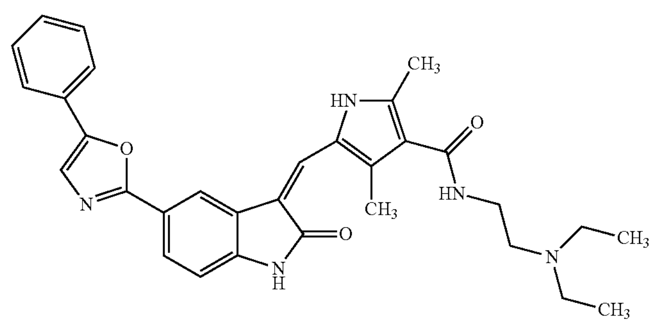 | 400 MHz ¹H-NMR (CDCl$_3$, δ) 13.35 (s, 1H), 8.36 (br, 1H), 8.20 (d, 1H, J = 1.4 Hz), 7.93 (dd, 1H, J = 8.1, 1.4 Hz), 7.75-7.70 (m, 2H), 7.52 (s, 1H), 7.48-7.30 (m, 4H), 6.99 (d, 1H, J = 8.1 Hz), 6.62 (br, 1H), 3.52 (m, 2H), 2.70 (t, 2H, J = 5.8 Hz), 2.62 (q, 4H, J = 7.1 Hz), 2.59 (s, 3H), 2.48 (s, 3H), 1.06 (t, 6H, J = 7.1 Hz) |
| 20 | 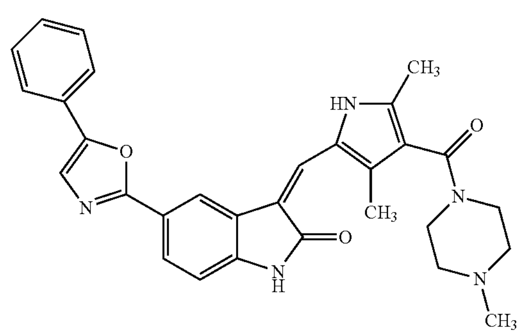 | 400 MHz ¹H-NMR (CDCl$_3$, δ) 13.32 (s, 1H), 8.22 (d, 1H, J = 1.6 Hz), 8.14 (br, 1H), 7.93 (dd, 1H, J = 8.1, 1.6 Hz), 7.76-7.72 (m, 2H), 7.52 (s, 1H), 7.49-7.32 (m, 4H), 7.00 (d, 1H, J = 8.1 Hz), 4.0-3.3 (m, 4H), 2.6-2.3 (m, 4H), 2.40 (s, 3H), 2.34 (s, 3H), 2.33 (s, 3H) |

TABLE 4-continued
| Example | structure | Spectral data |
|---|---|---|
| 21 | 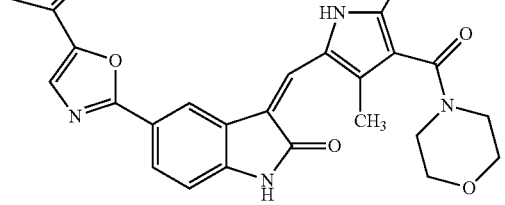 | 400 MHz ¹H-NMR (CDCl₃, δ) 13.34 (s, 1H), 8.24 (br, 1H), 7.96-7.91 (m, 2H), 7.77-7.72 (m, 2H), 7.53 (s, 1H), 7.49-7.32 (m, 4H), 7.00 (d, 1H, J = 8.1 Hz), 4.0-3.3 (m, 8H), 2.41 (s, 3H), 2.36 (s, 3H) |
| 22 | 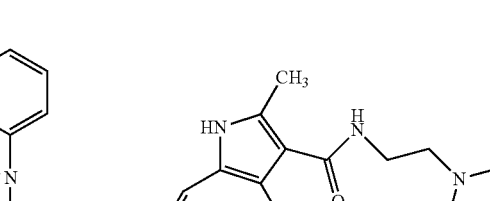 | 400 MHz ¹H-NMR (CDCl₃, δ) 13.26 (s, 1H), 7.69 (s, 1H), 7.67 (d, 1H, J = 1.8 Hz), 7.30-7.23 (m, 6H), 7.17 (s, 1H), 6.90 (dd, 1H, J = 1.6, 8.1 Hz), 6.73 (d, 1H, J = 8.1 Hz), 6.47 (d, 1H, J = 1.8 Hz), 3.55-3.40 (m, 2H), 2.73-2.47 (m, 6H), 2.53 (s, 3H), 2.39 (s, 3H), 1.09-0.91 (m, 6H). |
| 23 | 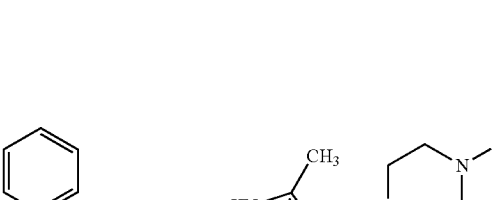 | 400 MHz ¹H-NMR (CDCl₃, δ) 13.27 (s, 1H), 8.05 (s, 1H), 7.76 (d, 1H, J = 1.8 Hz), 7.39-7.31 (m, 6H), 7.21 (s, 1H), 6.99 (dd, 1H, J = 1.6, 8.1 Hz), 6.81 (d, 1H, J = 8.1 Hz), 6.55 (d, 1H, J = 1.8 Hz), 3.95-3.37 (br, 4H), 2.56-2.30 (m, 4H), 2.41 (s, 3H), 2.35 (s, 3H), 2.27 (s, 3H). |
| 24 | 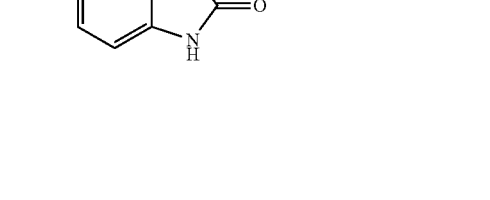 | 400 MHz ¹H-NMR (CDCl₃, δ) 13.22 (s, 1H), 7.84 (s, 1H), 7.71 (d, 1H, J = 1.8 Hz), 7.55 (dt, 2H, J = 1.9, 8.7 Hz), 7.41 (dt, 2H, J = 1.9, 8.7 Hz), 7.35 (1H, d, J = 1.5 Hz), 7.22 (s, 1H), 6.84 (dd, 1H, J = 1.5, 8.0 Hz), 6.78 (d, 1H, J = 8.0 Hz), 6.48 (d, 1H, J = 1.8 Hz), 3.90-3.30 (br, 4H), 2.47-2.20 (m, 4H), 2.33 (s, 3H), 2.27 (s, 3H), 2.17 (s, 3H). |

TABLE 4-continued

| Example | structure | Spectral data |
|---|---|---|
| 25 | 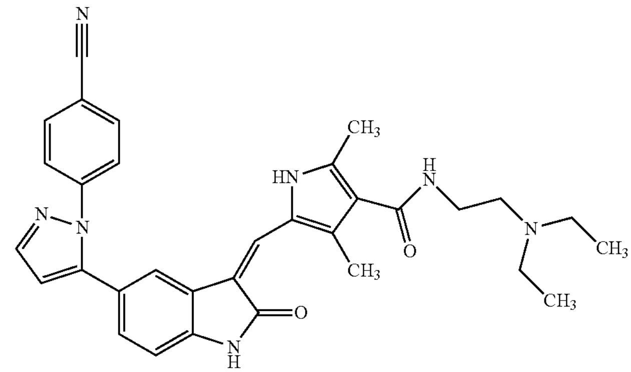 [SMILES: CCN(CC)CCNC(=O)c1c(C)[nH]c(/C=C2\C(=O)Nc3ccc(-c4ccnn4-c4ccc(C#N)cc4)cc32)c1C] | 400 MHz $^1$H-NMR (CDCl$_3$, δ) 13.30 (s, 1H), 7.96 (s, 1H), 7.71 (d, 1H, J = 1.8 Hz), 7.55 (dt, 2H, J = 2.1, 8.7 Hz), 7.41 (dt, 2H, J = 2.1, 8.7 Hz), 7.36 (1H, d, J = 1.5 Hz), 7.26 (s, 1H), 6.83 (dd, 1H, J = 1.5, 8.0 Hz), 6.78 (d, 1H, J = 8.0 Hz), 6.48 (d, 1H, J = 1.8 Hz), 3.47-3.40 (m, 2H), 2.65-2.49 (m, 6H), 2.53 (s, 3H), 2.38 (s, 3H), 0.98 (t, 6H, J = 6.9 Hz). |
| 26 | 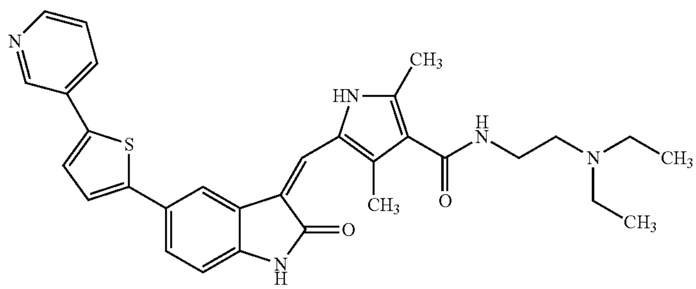 [SMILES: CCN(CC)CCNC(=O)c1c(C)[nH]c(/C=C2\C(=O)Nc3ccc(-c4ccc(-c5cccnc5)s4)cc32)c1C] | 300 MHz $^1$H-NMR (CDCl$_3$, δ) 13.38 (s, 1H), 8.86 (s, 1H), 8.48 (d, 1H, J = 4.5 Hz), 8.21 (s, 1H), 7.84 (d, 1H, J = 7.5 Hz), 7.63 (s, 1H), 7.43-7.34 (m, 2H), 7.30-7.25 (m, 2H), 6.92 (d, 1H, J = 8.1 Hz), 3.72 (brs, 2H), 3.03-2.92 (m, 6H), 2.59 (s, 3H), 2.52 (s, 3H), 1.26 (d, 6H, J = 5.1 Hz) |
| 27 | 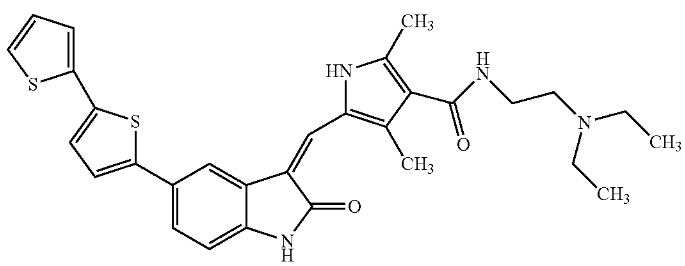 [SMILES: CCN(CC)CCNC(=O)c1c(C)[nH]c(/C=C2\C(=O)Nc3ccc(-c4ccc(-c5cccs5)s4)cc32)c1C] | 400 MHz $^1$H-NMR (CDCl$_3$, δ) 13.33 (s, 1H), 7.80 (s, 1H), 7.60 (d, 1H, J = 1.6 Hz), 7.40 (s, 1H), 7.35 (dd, 1H, J = 1.7, 8.1 Hz), 7.16-7.12 (m, 3H), 7.08 (d, 1H, J = 3.7 Hz), 6.97 (dd, 1H, J = 3.7, 5.1 Hz), 6.84 (d, 1H, J = 8.1 Hz), 3.69-3.63 (m, 2H), 3.54-3.40 (m, 2H), 2.72-2.49 (m, 4H), 2.54 (s, 3H), 2.47 (s, 3H), 1.08-0.95 (m, 6H). |
| 28 | 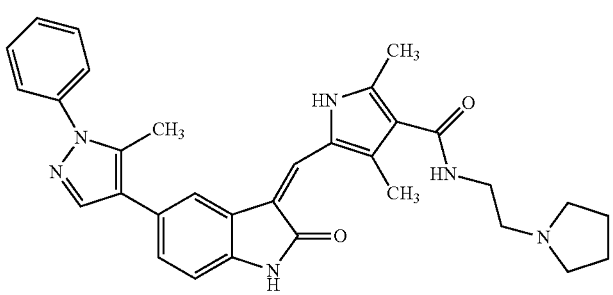 [SMILES: Cc1[nH]c(/C=C2\C(=O)Nc3ccc(-c4cnn(-c5ccccc5)c4C)cc32)c(C)c1C(=O)NCCN1CCCC1] | 300 MHz $^1$H-NMR (CDCl$_3$, δ) 13.22 (s, 1H), 9.63 (s, 1H), 7.76 (s, 1H), 7.46-7.37 (m, 5H), 7.19-7.11 (m, 3H), 6.90-6.88 (m, 1H), 3.69-3.60 (m, 2H), 3.05-2.80 (m, 6H), 2.51 (s, 3H), 2.41 (s, 3H), 2.21 (s, 3H), 2.02-1.91 (m, 4H) |

TABLE 4-continued

| Example | structure | Spectral data |
|---|---|---|
| 29 | 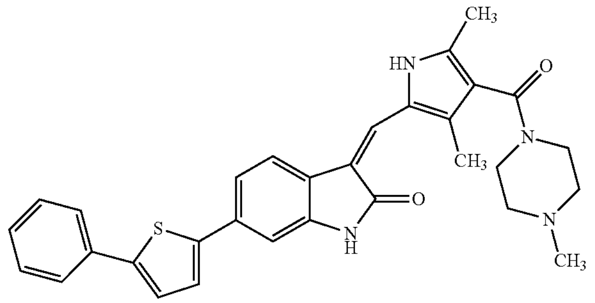 [SMILES: Cc1[nH]c(/C=C2\C(=O)Nc3cc(-c4ccc(-c5ccccc5)s4)ccc32)c(C)c1C(=O)N1CCN(C)CC1] | LCMS m/z 523.66 (M + H) |
| 30 | 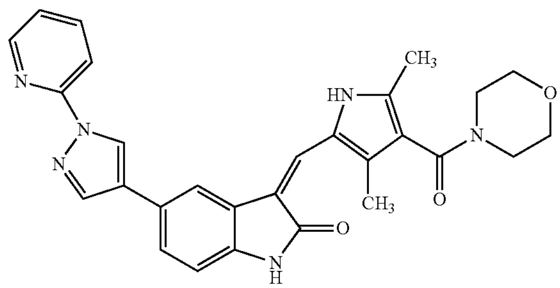 [SMILES: Cc1[nH]c(/C=C2\C(=O)Nc3ccc(-c4cnn(-c5ccccn5)c4)cc32)c(C)c1C(=O)N1CCOCC1] | 300 MHz $^1$H-NMR (CDCl$_3$, δ) 13.34 (s, 1H), 8.82 (s, 1H), 8.43 (d, 1H, J = 4.2 Hz), 8.01 (t, 2H, J = 3.6 Hz), 7.86-7.81 (m, 2H), 7.67 (s, 1H), 7.42-7.37 (m, 2H), 7.20 (t, 1H, J = 6.3 Hz), 6.91 (d, 1H, J = 7.8 Hz), 3.69 (brs, 8H), 2.89 (s, 3H), 2.36 (s, 3H) |
| 31 | 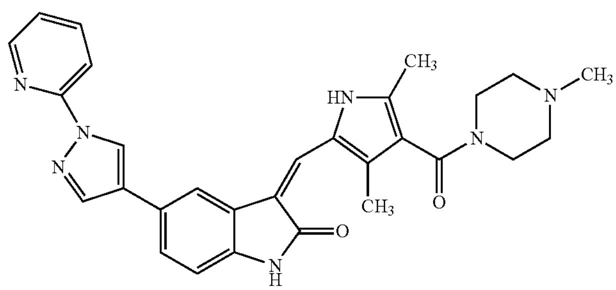 [SMILES: Cc1[nH]c(/C=C2\C(=O)Nc3ccc(-c4cnn(-c5ccccn5)c4)cc32)c(C)c1C(=O)N1CCN(C)CC1] | 300 MHz $^1$H-NMR (DMSO-d$_6$, δ) 13.61 (s, 1H), 10.93 (s, 1H), 9.09 (s, 1H), 8.50 (d, 1H, J = 4.8 Hz), 8.32 (s, 1H), 8.25 (s, 1H), 8.00-7.95 (m, 2H), 7.78 (s, 1H), 7.54 (d, 1H, J = 8.4 Hz), 7.37 (t, 1H, J = 5.4 Hz), 6.89 (d, 1H, J = 7.8 Hz), 3.47 (brs, 4H), 2.32-2.26 (m, 13H) |
| 32 | 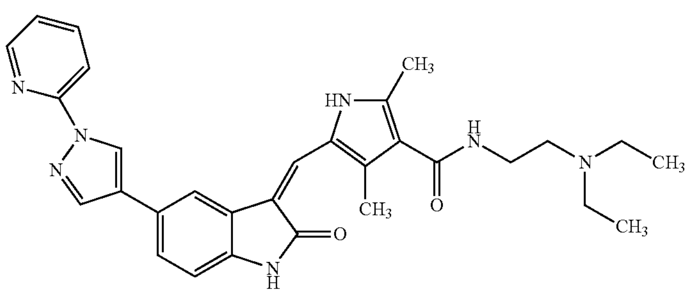 [SMILES: CCN(CC)CCNC(=O)c1c(C)[nH]c(/C=C2\C(=O)Nc3ccc(-c4cnn(-c5ccccn5)c4)cc32)c1C] | 300 MHz $^1$H-NMR (CDCl$_3$, δ) 13.38 (s, 1H), 8.79 (s, 1H), 8.42 (d, 1H, J = 3.6 Hz), 8.11 (s, 1H), 8.00-7.97 (m, 2H), 7.81 (t, 1H, J = 6.9 Hz), 7.64 (s, 1H), 7.42 (s, 1H), 7.19 (d, 1H, J = 6.6 Hz), 6.91 (d, 1H, J = 7.8 Hz), 3.56 (brs, 4H), 2.79-2.70 (m, 6H), 2.58 (s, 3H), 2.51 (s, 3H), |
| 33 | 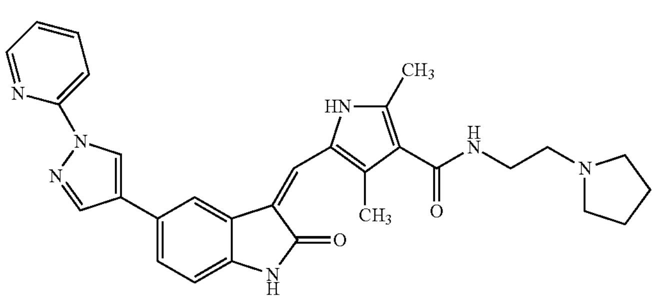 [SMILES: Cc1[nH]c(/C=C2\C(=O)Nc3ccc(-c4cnn(-c5ccccn5)c4)cc32)c(C)c1C(=O)NCCN1CCCC1] | 300 MHz $^1$H-NMR (CDCl$_3$, δ) 13.34 (s, 1H), 8.78 (s, 1H), 8.40 (d, 1H, J = 3.9 Hz), 8.30 (s, 1H), 7.99-7.95 (m, 2H), 7.80 (t, 1H, J = 7.5 Hz), 7.62 (s, 1H), 7.38-7.35 (m, 2H), 7.18 (d, 1H, J = 7.2 Hz), 6.89 (d, 1H, J = 7.8 Hz), 3.70 (brs, 2H), 3.02 (brs, 6H), 2.56 (s, 3H), 2.47 (s, 3H), 1.96 (brs, 4H) |

TABLE 4-continued
| Example | structure | Spectral data |
|---|---|---|
| 34 | 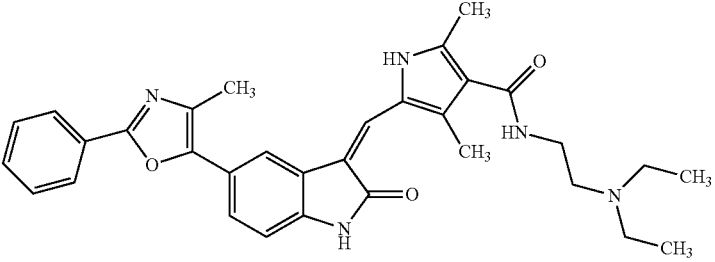 [SMILES: CCN(CC)CCNC(=O)c1c(C)[nH]c(/C=C2\C(=O)Nc3ccc(-c4oc(-c5ccccc5)nc4C)cc32)c1C] | 300 MHz $^1$H-NMR (DMSO-$d_6$, δ) 13.71 (s, 1H), 11.09 (s, 1H), 8.10-8.07 (m, 3H), 7.82 (s, 1H), 7.53-7.45 (m, 5H), 7.03-7.00 (m, 1H), 3.34-3.27 (m, 7H), 2.45-2.39 (m, 10H), 0.99-0.94 (m, 6H) |
| 35 | 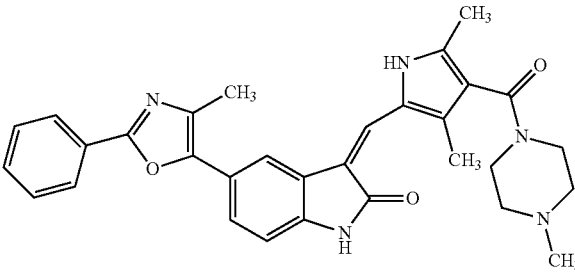 | 300 MHz $^1$H-NMR (DMSO-$d_6$, δ) 13.64 (s, 1H), 11.86 (s, 1H), 8.12-8.07 (m, 2H), 7.81 (s, 1H), 7.58-7.48 (m, 5H), 7.09-7.03 (m, 1H), 3.96-3.45 (m, 7H), 2.50-2.47 (m, 4H), 2.34 (s, 3H), 2.27 (s, 3H), 2.14 (s, 3H) |
| 36 | 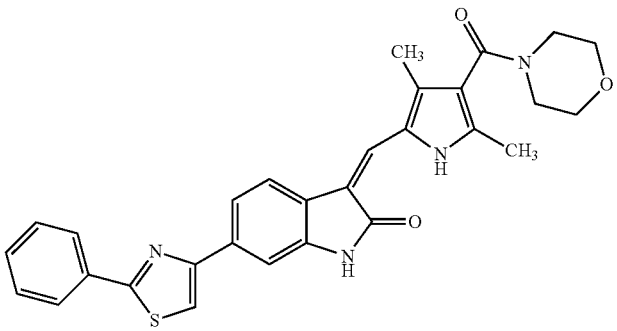 [SMILES: Cc1[nH]c(/C=C2\C(=O)Nc3cc(-c4csc(-c5ccccc5)n4)ccc32)c(C)c1C(=O)N1CCOCC1] | 300 MHz $^1$H-NMR (DMSO-$d_6$, δ) 13.59 (s, 1H), 11.02 (s, 1H), 8.15 (s, 1H), 8.05-8.00 (m, 2H), 7.87 (d, 1H, J = 8.3 Hz), 7.72-7.67 (m, 2H), 7.58-7.53 (m, 4H), 3.65-3.53 (m, 4H), 2.31 (s, 3H), 2.29 (s, 3H) |
| 37 | 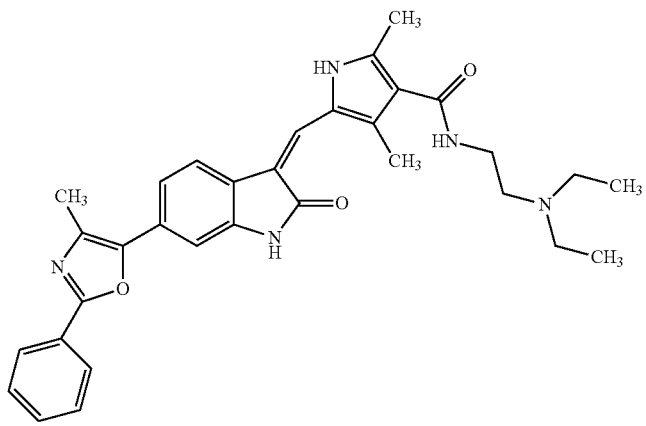 [SMILES: CCN(CC)CCNC(=O)c1c(C)[nH]c(/C=C2\C(=O)Nc3cc(-c4oc(-c5ccccc5)nc4C)ccc32)c1C] | LCMS m/z 538.65 (M + H) |

| Example | structure | Spectral data |
|---|---|---|
| 38 | 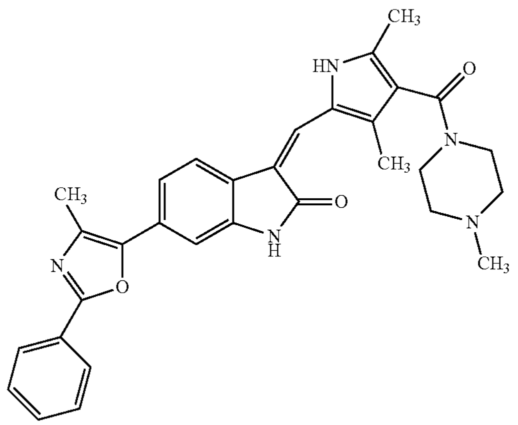 [SMILES: Cc1nc(-c2ccccc2)oc1-c1ccc2c(c1)NC(=O)/C2=C\c1[nH]c(C)c(C(=O)N2CCN(C)CC2)c1C] | LCMS m/z 522.61 (M + H) |
| 39 | 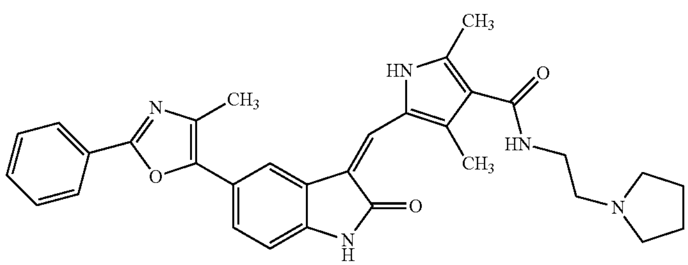 [SMILES: Cc1nc(-c2ccccc2)oc1-c1ccc2c(c1)/C(=C/c1[nH]c(C)c(C(=O)NCCN3CCCC3)c1C)C(=O)N2] | LCMS m/z 536.64 (M + H) |
| 40 | 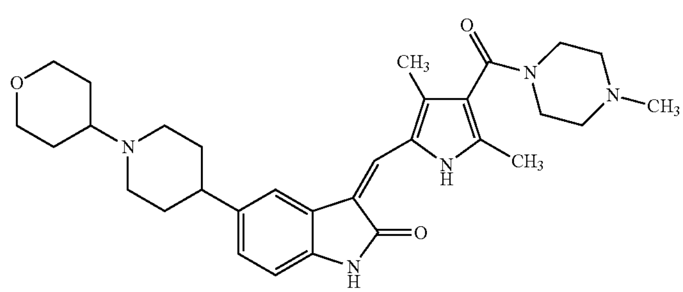 [SMILES: Cc1[nH]c(/C=C2\C(=O)Nc3ccc(C4CCN(C5CCOCC5)CC4)cc32)c(C)c1C(=O)N1CCN(C)CC1] | 300 MHz $^1$H-NMR (DMSO-$d_6$, δ) 13.60 (s, 1H), 10.76 (s, 1H), 7.73 (s, 1H), 7.65 (s, 1H), 6.96 (dd, 1H, J = 7.9, 8.4 Hz), 6.75 (d, 1H, J = 7.9 Hz), 3.92-3.84 (m, 2H), 3.57-3.35 (m, 4H), 3.04-2.96 (m, 2H), 2.52-2.35 (m, 3H), 2.32-2.15 (m, 7H), 2.26 (s, 3H), 2.26 (s, 3H), 2.18 (s, 3H), 1.78-1.64 (m, 6H), 1.52-1.37 (m, 2H) |
| 41 | 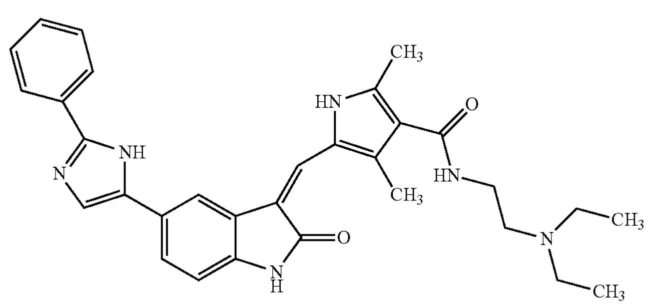 [SMILES: CCN(CC)CCNC(=O)c1c(C)[nH]c(/C=C2\C(=O)Nc3ccc(-c4cnc(-c5ccccc5)[nH]4)cc32)c1C] | 300 MHz $^1$H-NMR (DMSO-$d_6$, δ) 13.68 (s, 1H), 12.61 (s, 1H), 10.93 (s, 1H), 8.18 (s, 1H), 8.03-8.01 (m, 2H), 7.78-7.70 (m, 2H), 7.51-7.44 (m, 2H), 7.32-7.37 (m, 1H), 6.91-6.89 (m, 1H), 3.34-3.30 (m, 4H), 2.64-2.60 (m, 4H), 2.50-2.48 (m, 6H), 0.99-0.96 (m, 6H) |

TABLE 4-continued

| Example | structure | Spectral data |
|---|---|---|
| 42 | 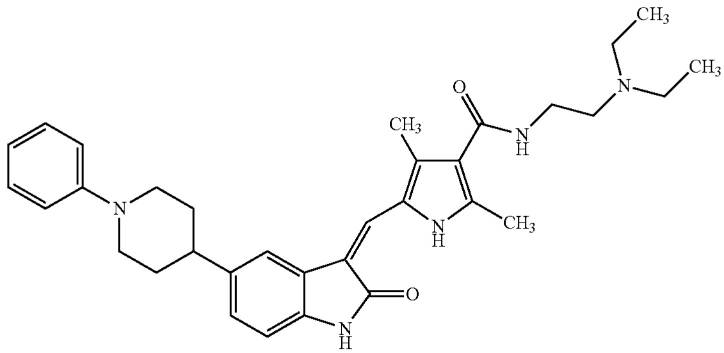 [SMILES: CCN(CC)CCNC(=O)c1c(C)[nH]c(/C=C2\C(=O)Nc3ccc(C4CCN(c5ccccc5)CC4)cc32)c1C] | 300 MHz ¹H-NMR (DMSO-d$_6$, δ) 13.68 (s, 1H), 10.80 (s, 1H), 7.78 (s, 1H), 7.68 (s, 1H), 7.24-7.19 (m, 2H), 7.04-6.95 (m, 3H), 6.80-6.74 (m, 2H), 3.84-3.76 (m, 2H), 3.35-3.22 (m, 3H), 2.78-2.53 (m, 6H), 2.50-2.36 (m, 2H), 2.43 (s, 3H), 2.42 (s, 3H), 1.91-1.81 (m, 4H), 1.01 (brs, 6H) |
| 43 | 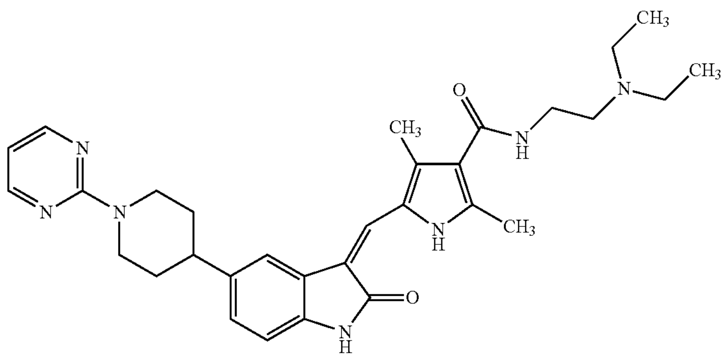 [SMILES: CCN(CC)CCNC(=O)c1c(C)[nH]c(/C=C2\C(=O)Nc3ccc(C4CCN(c5ncccn5)CC4)cc32)c1C] | 300 MHz ¹H-NMR (DMSO-d$_6$, δ) 13.66 (s, 1H), 10.79 (s, 1H), 8.36 (s, 1H), 8.34 (s, 1H), 7.73 (s, 1H), 7.65 (s, 1H), 7.40-7.36 (m, 1H), 6.99 (brd, 1H, J = 7.9 Hz), 6.77 (d, 1H, J = 7.9 Hz), 6.58 (t, 1H, J = 4.6 Hz), 4.90-4.80 (m, 2H), 3.30-3.20 (m, 2H), 2.98-2.86 (m, 2H), 2.86-2.69 (m, 1H), 2.56-2.44 (m, 6H), 2.42 (s, 3H), 2.40 (s, 3H), 1.89-1.78 (m, 2H), 1.72-1.55 (m, 2H), 0.96 (t, 6H, J = 7.0 Hz) |
| 44 | 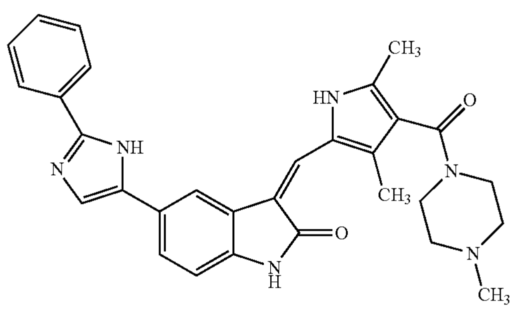 [SMILES: Cc1[nH]c(/C=C2\C(=O)Nc3ccc(-c4cnc(-c5ccccc5)[nH]4)cc32)c(C)c1C(=O)N1CCN(C)CC1] | 300 MHz ¹H-NMR (DMSO-d$_6$, δ) 13.62 (s, 1H), 12.60 (s, 1H), 10.90 (s, 1H), 8.14 (s, 1H), 8.02-7.99 (m, 2H), 7.71-7.67 (m, 2H), 7.51-7.44 (m, 2H), 7.37-7.32 (m, 1H), 6.90-6.87 (m, 1H), 3.45-3.33 (m, 4H), 2.50-2.48 (m, 4H), 2.29 (s, 3H), 2.19 (s, 3H), 2.14 (s, 3H) |
| 45 | 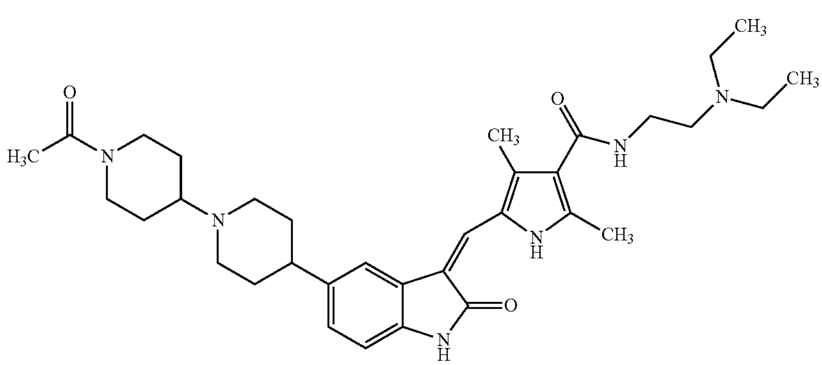 [SMILES: CCN(CC)CCNC(=O)c1c(C)[nH]c(/C=C2\C(=O)Nc3ccc(C4CCN(C5CCN(C(C)=O)CC5)CC4)cc32)c1C] | 300 MHz ¹H-NMR (DMSO-d$_6$, δ) 13.66 (s, 1H), 10.77 (s, 1H), 7.75 (s, 1H), 7.67 (s, 1H), 7.38 (t, 1H, J = 5.6 Hz), 6.96 (brd, 1H, J = 7.9 Hz), 6.75 (d, 1H, J = 7.9 Hz), 4.43-4.36 (m, 1H), 3.86-3.80 (m, 1H), 3.35-3.23 (m, 4H), 2.98-2.93 (m, 2H), 2.55-2.38 (m, 8H), 2.42 (s, 3H), 2.42 (s, 3H), 2.30-2.15 (m, 2H), 1.98 (s, 3H), 1.70-1.64 (m, 6H), 1.48-1.15 (m, 2H), 0.96 (t, 6H, J = 7.2 Hz) |

TABLE 4-continued

| Example | structure | Spectral data |
|---|---|---|
| 46 | 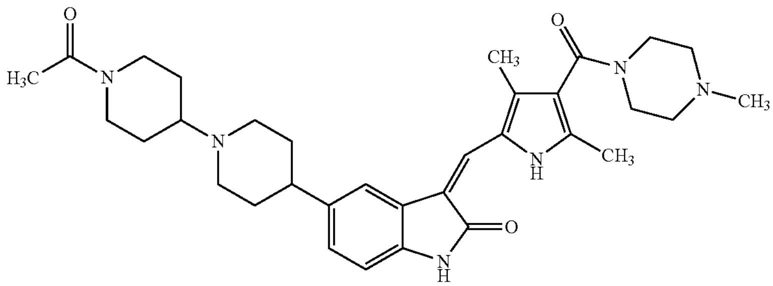 [SMILES: CC(=O)N1CCC(N2CCC(c3ccc4c(c3)/C(=C/c3[nH]c(C)c(C(=O)N5CCN(C)CC5)c3C)C(=O)N4)CC2)CC1] | 300 MHz ¹H-NMR (DMSO-d₆, δ) 13.60 (s, 1H), 10.77 (s, 1H), 7.73 (s, 1H), 7.65 (s, 1H), 6.96 (d, 1H, J = 7.9 Hz), 6.75 (brd, 1H, J = 7.9 Hz), 4.43-4.35 (m, 1H), 3.88-3.78 (m, 1H), 3.60-3.38 (m, 4H), 3.04-2.90 (m, 2H), 2.56-2.20 (m, 8H), 2.26 (s, 3H), 2.26(s, 3H), 2.19 (s, 3H), 2.00-1.91 (m, 2H), 1.98 (s, 3H), 1.70-1.65 (m, 6H), 1.48-1.18 (m, 2H) |
| 47 | 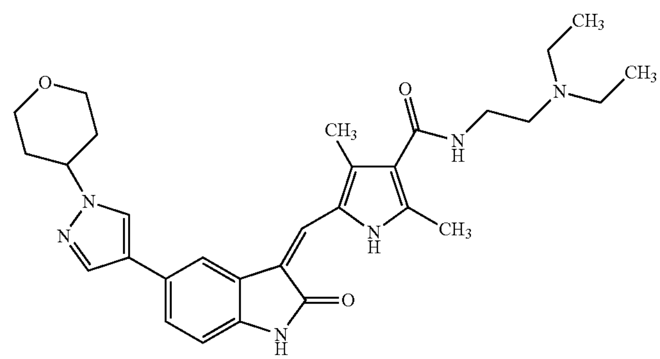 [SMILES: CCN(CC)CCNC(=O)c1c(C)[nH]c(/C=C2\C(=O)Nc3ccc(-c4cnn(C5CCOCC5)c4)cc32)c1C] | 300 MHz ¹H-NMR (DMSO-d₆, δ) 13.64 (s, 1H), 10.88 (s, 1H), 8.19 (s, 1H), 8.00 (s, 1H), 7.90 (s, 1H), 7.68 (s, 1H), 7.45-7.38 (m, 1H), 7.35 (d, 1H, J = 7.9 Hz), 6.85 (d, 1H, J = 7.9 Hz), 4.44-4.33 (m, 1H), 4.02-3.91 (m, 2H), 3.52-3.43 (m, 2H), 3.32-3.24 (m, 2H), 2.58-2.48 (m, 6H), 2.44 (s, 3H), 2.44 (s, 3H), 2.06-1.89 (m, 4H), 0.97 (t, 6H, J = 7.0 Hz) |
| 48 | 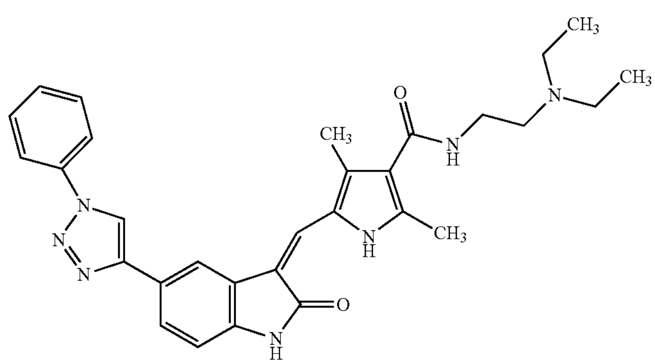 [SMILES: CCN(CC)CCNC(=O)c1c(C)[nH]c(/C=C2\C(=O)Nc3ccc(-c4cn(-c5ccccc5)nn4)cc32)c1C] | 300 MHz ¹H-NMR (DMSO-d₆, δ) 13.64 (s, 1H), 11.06 (s, 1H), 9.18 (s, 1H), 8.30 (s, 1H), 7.96 (d, 2H, J = 9 Hz), 7.75-7.45 (m, 6H), 7.00 (d, 1H, J = 9 Hz), 3.39-3.26 (m, 4H), 2.56-2.45 (m, 10H), and 0.97 (t, J = 7.5 Hz). |
| 49 | 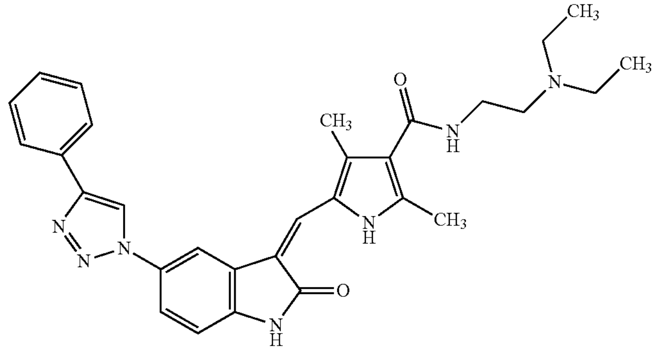 [SMILES: CCN(CC)CCNC(=O)c1c(C)[nH]c(/C=C2\C(=O)Nc3ccc(-n4cc(-c5ccccc5)nn4)cc32)c1C] | LCMS m/z 524.5 (M + H) |

TABLE 4-continued

| Example | structure | Spectral data |
|---|---|---|
| 50 | 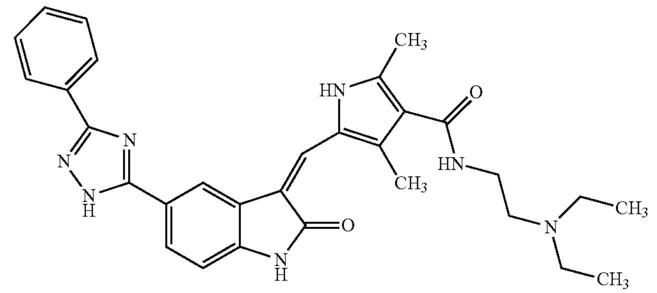 | 300 MHz ¹H-NMR (DMSO-d$_6$, δ) 13.64 (s, 1H), 11.14 (s, 1H), 8.41 (s, 1H), 8.12-8.11 (m, 2H), 7.87-7.85 (m, 1H), 7.84 (s, 1H), 7.55-7.48 (m, 4H), 7.03-7.01 (m, 1H), 3.34-3.25 (m, 4H), 2.54-2.45 (m, 10H), 0.99-0.95 (m, 6H) |

Example 51

Production of (Z)—N-(2-(diethylamino)ethyl)-2,4-dimethyl-5-((2-oxo-5-(4-phenylthiazol-2-yl)indolin-3-ylidene)methyl)-1H-pyrrole-3-carboxamide

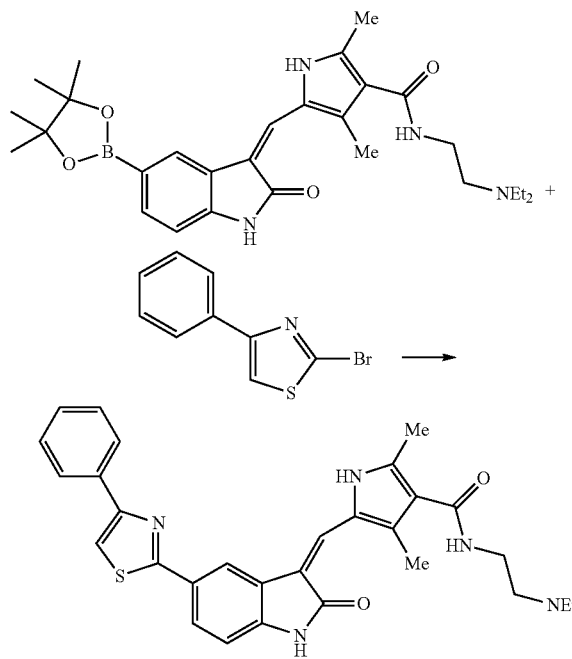

To a solution of No (40 mg, 0.079 mmol) in DMF/H$_2$O (3 ml/1 ml) was added Pd(PPh$_3$)$_4$ (9.1 mg, 0.008 mmol), 5-phenylthiophene-2-boronic acid (23 mg, 0.095 mmol) and potassium carbonate (33 mg, 0.237 mmol). The mixture was stirred at 110° C. for 1 hour under microwave irradiation. The mixture was extracted with CHCl$_3$, and the organic layer was washed with H$_2$O, dried over Na$_2$SO$_4$ and concentrated in vacuo. The residue was purified by column chromatography (CHCl$_3$/MeOH) to give (Z)—N-(2-(diethylamino)ethyl)-2,4-dimethyl-5-((2-oxo-5-(4-phenylthiazol-2-yl)indolin-3-ylidene)methyl)-1H-pyrrole-3-carboxamide (10 mg) as yellow solid.

¹H NMR (300 MHz, DMSO-d$_6$) δ 13.70 (s, 1H), 11.20 (s, 1H), 8.43 (s, 1H), 8.07-8.11 (m, 3H), 7.79-7.90 (m. 2H), 7.39-7.50 (m, 4H), 7.02 (m, 1H), 3.25-3.35 (m, 4H), 2.4-2.6 (m, 10H), 0.95-0.99 (m, 6H); MS m/z 540.69 (M+H).

Examples 52 to 55

Reactions and treatments were carried out in the same manner as in Example 1 using the corresponding starting material compounds, thereby giving the compounds of Examples 52 to 55 shown in Table 5.

TABLE 5

| Example | structure | Spectral data |
|---|---|---|
| 52 | 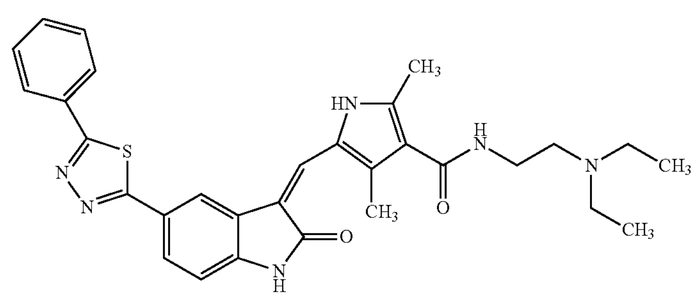 | 300 MHz ¹H-NMR (CDCl$_3$, δ) 13.24 (s, 1H), 8.03 (s, 1H), 7.89 (t, 1H, J = 3.3 Hz), 7.83 (s, 1H), 7.58 (t, 1H, J = 9.0 Hz), 7.41-7.27 (m, 4H), 6.91-6.82 (m, 1H), 3.62 (brs, 2H), 2.93-2.82 (m, 6H), 2.62-2.36 (m, 6H), 1.18-1.15 (m, 6H) |

TABLE 5-continued

| Example | structure | Spectral data |
|---|---|---|
| 53 | 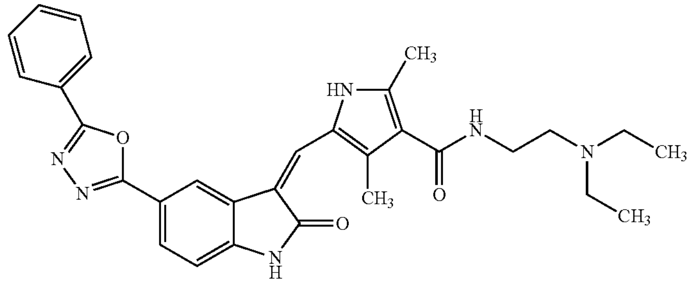 [SMILES: CCN(CC)CCNC(=O)c1c(C)[nH]c(/C=C2\C(=O)Nc3ccc(-c4nnc(-c5ccccc5)s4)cc32)c1C] | 300 MHz ¹H-NMR (CD₃OD, δ) 8.34 (s, 1H), 8.16 (d, 2H, J = 7.8 Hz), 7.92 (d, 1H, J = 8.4 Hz), 7.65-7.60 (m, 5H), 7.08 (d, 1H, J = 8.1 Hz), 3.59 (t, 2H, J = 6.6 Hz), 2.99-2.88 (m, 6H), 2.52 (s, 3H), 2.50 (s, 3H), 1.22 (t, 6H, J = 7.2 Hz) |
| 54 | 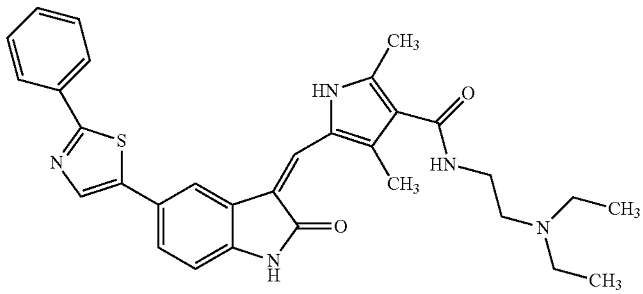 [SMILES: CCN(CC)CCNC(=O)c1c(C)[nH]c(/C=C2\C(=O)Nc3ccc(-c4cnc(-c5ccccc5)s4)cc32)c1C] | 300 MHz ¹H-NMR (DMSO-d₆, δ) 13.64 (s, 1H), 11.07 (s, 1H), 8.28 (s, 1H), 8.23 (s, 1H), 7.96-7.94 (m, 2H), 7.83 (s, 1H), 7.55-7.42 (m, 4H), 6.97-6.94 (m, 1H), 3.38-3.25 (m, 4H), 2.56-2.40 (m, 10H), 0.99-0.95 (m, 6H) |
| 55 | 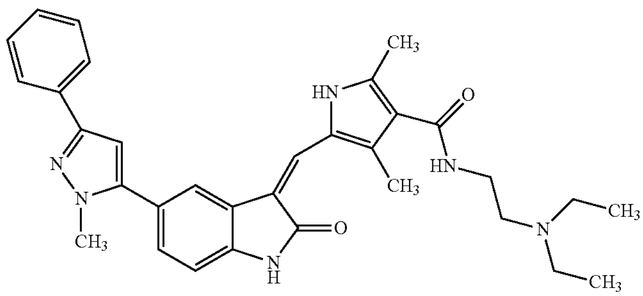 [SMILES: CCN(CC)CCNC(=O)c1c(C)[nH]c(/C=C2\C(=O)Nc3ccc(-c4cc(-c5ccccc5)nn4C)cc32)c1C] | 300 MHz ¹H-NMR (DMSO-d₆, δ) 13.65 (s, 1H), 11.25 (s, 1H), 7.86 (s, 1H), 7.75 (s, 1H), 7.55 (s, 1H), 7.44-7.41 (m, 3H), 7.27-7.21 (m, 3H), 6.91-6.89 (m, 1H), 6.78-6.75 (m, 1H), 3.96 (s, 3H), 3.34-3.28 (m, 4H), 2.55-2.50 (m, 4H), 2,45 (s, 3H), 2.34 (s, 3H), 0.99-0.97 (m, 6H) |

Example 56

Production of (Z)—N-(2-(diethylamino)ethyl)-2,4-dimethyl-5-((2-oxo-5-(5-phenylfuran-2-yl)indolin-3-ylidene)methyl)-1H-pyrrole-3-carboxamide

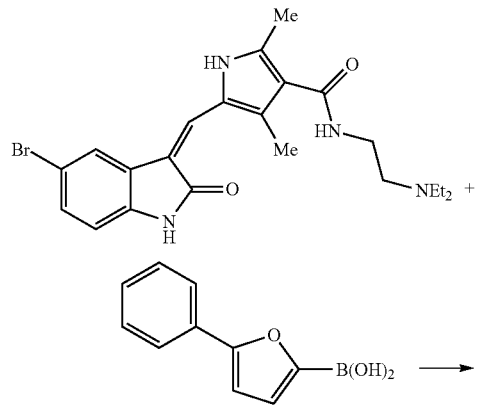

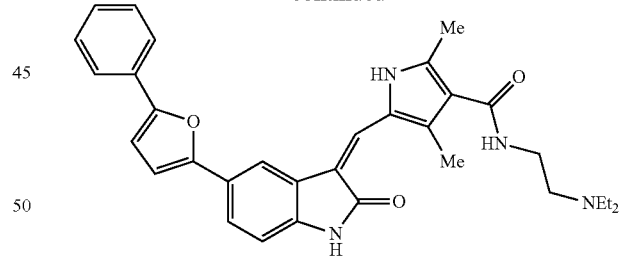

To a solution of No (31 mg, 0.068 mmol) in DMF/H₂O (0.75 ml/0.25 ml) was added Pd(PPh₃)₄ (15.9 mg, 0.014 mmol), 5-phenylfuran-2-boronic acid (17 mg, 0.090 mmol) and potassium carbonate (14 mg, 0.100 mmol). The mixture was stirred at 120° C. for 1 hour under microwave irradiation. The mixture was concentrated in vacuo. The residue was purified by reverse phase column chromatography (H₂O/CH₃CN) to give (Z)—N-(2-(diethylamino)ethyl)-2,4-dimethyl-5-((2-oxo-5-(5-phenylfuran-2-yl)indolin-3-ylidene)methyl)-1H-pyrrole-3-carboxamide (12 mg) as an orange solid.

¹H NMR (300 MHz, CDCl₃) δ 7.76-7.72 (m, 3H), 7.55 (d, 1H, J=9.9 Hz), 7.45-7.37 (m, 3H), 7.27-7.24 (m, 3H), 6.91 (d,

1H, J=8.4 Hz), 6.72 (d, 1H, J=3.3 Hz), 6.67 (d, 1H, J=3.6 Hz), 3.57 (brs, 2H), 2.71 (brs, 4H), 2.58 (s, 3H), 2.52 (s, 3H), 1.11 (brs, 6H).

Test Example 1

Biological Assays

Compounds of the present invention can be tested according to the protocol described.

Cell Culture: FaDu (ATCC, Manassas, Va.) was maintained in Dulbecco's Modified Eagle Medium (DMEM) (Invitrogen, Carlsbad, Calif.) supplemented with 10% fetal bovine serum (FBS) (Gemini Bio-Products, West Sacramento, Calif.) and 5% penicillin/streptomycin/amphotercin B (Invitrogen).

Cell Viability Determination: For colony formation assay, cells were plated in 6 well plates at 2000 cells per well. Twenty-four hours after plating, cells were treated with compound. Colonies were allowed to develop for 7-10 days, at which they were stained with modified Giemsa stain (Sigma). Stained colonies were then counted to determine $IC_{50}$.

Western Blot Analysis: Cultured cells were harvested and lysed in whole-cell extract buffer (50 mM Tris-HcL pH 7.5, 150 mM NaCl, 1.0% NP-40, 1 mM EDTA, 0.1 mM sodium orthovanadate, IX protease inhibitor cocktail (Roche)) by incubation for 30 minutes on ice. Soluble proteins were separated by centrifugation at 13,000×g in a microcentrifuge, and supernatants were stored at −70° C. Proteins were separated by sodium dodecyl sulfate-polyacrylamide gel electrophoresis analysis and transferred to a polyvinylidene difluoride membrane (Biorad, Hercules, Calif.) by electroblotting.

CSC isolation with surface markers: Sorting tumor cells based primarily upon the differential expression of the surface marker(s), such as CD44 or CD133, have accounted for the majority of the highly tumorigenic CSCs described to date. $CD44^{high}$ cells were isolated by FACS according to the methods described in Ponti et al, with slight modification [Ponti, D., et al, *Isolation and in vitro propagation of tumorigenic breast cancer cells with stem/progenitor cell properties*. Cancer Res, 2005. 65(13); p. 5506-11.], Briefly, after trypsinization and recovery of cells for 30 minutes at 37° C. in growth media, cells were pelleted at 400×g and were resuspended in PBS with 2% FBS and ImM EDTA at $1×10^6$ cells/mL. Cells were then incubated on ice with a 1:100 dilution of CD44-FITC (BD Biosicences, San Diego, Calif.) for 15 minutes. Alternatively, CD24-PE (BD Bioscences, San Diego, Calif.) (1:100) was utilized for negative selection. After washing three times, cells were resuspended at 2×10 VmL and passed through a 40 .mu.M mesh before sorting.

Sphere assay: A reliable method of measuring the self-renewal capacity of cell population if the ability to be cultured as spheres in the absence of serum or attachment. $CD44^{high}$ FaDu cancer stem cells were cultured in ultra low attachment plates in cancer stem cell media (DMEM/F12, B27 Neurobasal supplement, 20 ng/ml EGF, 10 ng/rnl FGF, 4 .mu.g/ml insulin, and 0.4% BSA) to allow spheres formation. Typically, sphere formation was evaluated by microscopy after 10-14 days in culture and spheres with >50 cells were scored.

TABLE 5

| Example | colonyformation $IC_{50}$ (µM) | sphere $IC_{50}$ (µM) |
|---|---|---|
| 4 | 6.3 | 0.6 |
| 6 | 3.6 | 0.3 |
| 7 | 1.8 | 0.6 |
| 9 | 3.8 | 1.3 |
| 10 | 5.4 | 3 |
| 12 | 24 | >50 |
| 30 | >100 | 8.9 |
| 31 | 3.7 | 0.2 |
| 32 | 0.5 | 0.05 |
| 33 | 2.5 | 1.7 |
| 38 | 6.2 | 2 |
| 42 | 1.9 | 1.3 |
| 43 | 6.5 | 1.9 |
| 45 | 22 | >50 |
| 47 | 6.2 | 9.1 |

As shown in Table 5, compounds of present invention show a potent inhibitory activity for sphere formation of CSC.

Test Example 2

Solubility

Compounds of the present invention can be tested according to the protocol described.

A solution of compounds (10 mM in dimethylsulfoxide, 2 µL) was diluted with 50% acetonitrile (198 µL), and this solution was used as a standard solution.

On the other hand, a solution of compounds (10 mM in dimethylsulfoxide, 15 µL) was transferred to a 96 well plate, then solvent was removed in vacuo. Dimethyl sulfoxide (3 µL) was added to dissolve a residual solid, and then buffer solution (pH7.4 or 1.2, 300 µL) was added. The mixture was vigorously stirred for 90 min, then leave it for 16-20 h. An insoluble material was removed, then the solution was analyzed by HPLC. The concentration of compound, which was corresponding to a solubility of the compound, was determined by the comparison with area value between sample and the standard solution.

TABLE 6

| Example | pH 1.2 (mg/mL) | pH 7.4 (mg/mL) |
|---|---|---|
| 12 | >0.2000 | >0.2000 |
| 26 | >0.2000 | <0.0005 |
| 41 | 0.186 | 0.0003 |
| 42 | >0.2000 | 0.011 |
| 43 | 0.163 | 0.0004 |
| 48 | 0.147 | <0.0003 |
| 49 | 0.109 | 0.013 |
| 50 | 0.154 | 0.007 |
| 51 | >0.2000 | <0.0005 |
| 52 | 0.163 | 0.004 |
| 53 | >0.2000 | 0.061 |
| 55 | 0.043 | 0.0005 |

INDUSTRIAL APPLICABILITY

A compound of formula (1), or a pharmaceutically acceptable salt thereof is useful a CSCPKs inhibitor to inhibit, reduce or diminish cancer stem cell survival and/or proliferation in a mammal. A compound of formula (1), or a pharmaceutically acceptable salt thereof is also useful an anti cancer agent.

The invention claimed is:
1. A compound of formula 1:

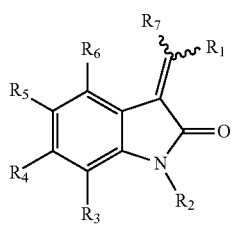
(1)

or a pharmaceutically acceptable salt thereof, wherein:
$R_1$ is optionally substituted heteroaryl, or optionally substituted heteroalicyclic;
$R_2$ is hydrogen, optionally substituted alkyl, optionally substituted alkylcarbonyl, optionally substituted alkoxycarbonyl, or optionally substituted aminocarbonyl;
$R_2$ and $R_4$ are each independently hydrogen, halogen, cyano, nitro, hydroxy, optionally substituted alkyl, optionally substituted alkoxy, optionally substituted amino, optionally substituted alkoxycarbonyl, optionally substituted alkylcarbonyl, optionally substituted aminocarbonyl, or

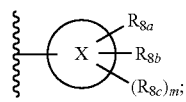

$R_5$ is hydrogen, halogen, cyano, nitro, hydroxy, optionally substituted alkyl, optionally substituted alkoxy, optionally substituted amino, optionally substituted alkoxycarbonyl, optionally substituted alkylcarbonyl, optionally substituted aminocarbonyl, or

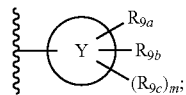

$R_6$ is hydrogen, halogen, cyano, nitro, hydroxy, amino, optionally substituted alkyl, optionally substituted alkoxy, optionally substituted amino, optionally substituted alkoxycarbonyl, optionally substituted alkyl carbonyl, or optionally substituted aminocarbonyl; and
$R_7$ is hydrogen, optionally substituted alkyl, or optionally substituted cycloalkyl,
wherein:
at least one of $R_3$, $R_4$ and $R_5$ is

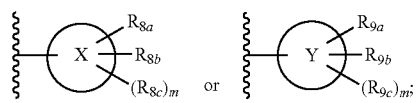

X is piperidine;
Y is optionally substituted five membered heteroaryl, provided that the five membered heteroaryl is not

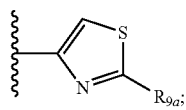

$R_{8a}$ is optionally substituted aryl, optionally substituted heteroaryl, or optionally substituted heteroalicyclic;
$R_{8b}$ and $R_{8c}$ are each independently hydrogen, alkyl, halogen, cyano, amino, nitro, hydroxy, trifluoromethyl, optionally substituted aryl, optionally substituted heteroaryl, or optionally substituted heteroalicyclic;
$R_{9a}$ is optionally substituted aryl, optionally substituted heteroaryl, or optionally substituted heteroalicyclic;
$R_{9b}$ and $R_{9c}$ are each independently hydrogen, alkyl, halogen, cyano, amino, nitro, hydroxy, or trifluoromethyl;
m is an integer from 0 to 2; and
n is an integer from 0 to 2.

2. A compound of formula 1:

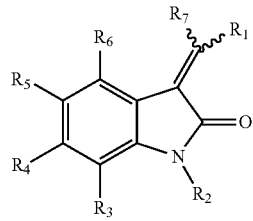
(1)

or a pharmaceutically acceptable salt thereof, wherein:
or a pharmaceutically acceptable salt thereof, wherein:
$R_1$ is optionally substituted heteroaryl, or optionally substituted heteroalicyclic;
$R_2$ is hydrogen, optionally substituted alkyl, optionally substituted alkylcarbonyl, optionally substituted alkoxycarbonyl, or optionally substituted aminocarbonyl;
$R_3$ and $R_4$ are each independently hydrogen, halogen, cyano, nitro, hydroxy, optionally substituted alkyl, optionally substituted alkoxy, optionally substituted amino, optionally substituted alkoxycarbonyl, optionally substituted alkylcarbonyl, optionally substituted aminocarbonyl, or

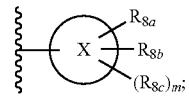

$R_5$ is hydrogen, halogen, cyano, nitro, hydroxy, optionally substituted alkyl, optionally substituted alkoxy, optionally substituted amino, optionally substituted alkoxycarbonyl, optionally substituted alkylcarbonyl, optionally substituted aminocarbonyl, or

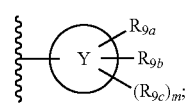

$R_6$ is hydrogen, halogen, cyano, nitro, hydroxy, amino, optionally substituted alkyl, optionally substituted alkoxy, optionally substituted amino, optionally substituted alkoxycarbonyl, optionally substituted alkyl carbonyl, or optionally substituted aminocarbonyl; and
$R_7$ is hydrogen, optionally substituted alkyl, or optionally substituted cycloalkyl,
wherein:
at least one of $R_3$, $R_4$ and $R_5$ is

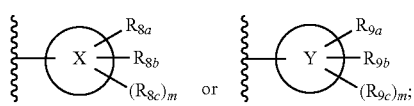

X is

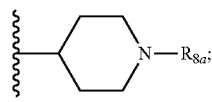

Y is optionally substituted five membered heteroaryl, provided that the five membered heteroaryl is not

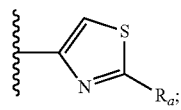

$R_{8a}$ is 4-piperazinyl (said piperidinyl is substituted with alkyl or alkylcarbonyl), 4-tetrahydropyranyl, phenyl, pyrazinyl, pyrimidinyl, pyridazinyl, or pyridiyl (said phenyl, pyrazinyl, pyrimidinyl, pyridazinyl, or pyridyl is optionally substituted with halogen, hydroxy, cyano, amino, nitro, alkyl, alkoxy, alkoxycarbonyl, alkylcarbonyl, or aminocarbonyl);

$R_{8b}$ and $R_{8c}$ are each independently hydrogen, alkyl, halogen, cyano, amino, nitro, hydroxy, trifluoromethyl, optionally substituted aryl, optionally substituted heteroaryl, or optionally substituted heteroalicyclic;

$R_{9a}$ is optionally substituted aryl, optionally substituted heteroaryl, or optionally substituted heteroalicyclic;

$R_{9b}$ and $R_{9c}$ are each independently hydrogen, alkyl, halogen, cyano, amino, nitro, hydroxy, or trifluoromethyl;

m is an integer from 0 to 2; and n is an integer from 0 to 2.

3. The compound according to claim 2, or a pharmaceutically acceptable salt thereof, wherein:

$R_5$ is hydrogen, halogen, cyano, nitro, hydroxy, alkyl, alkoxy, amino, alkylcarbonyl, alkoxycarbonyl, aminocarbonyl, or

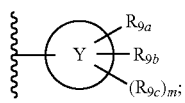

wherein said alkyl, alkoxy, amino, alkylcarbonyl, alkoxycarbonyl, and aminocarbonyl are optionally substituted with one or more substituents selected from the group consisting of alkyl, alkenyl, alkynyl, hydroxy, amino, nitro, cyano, halogen, alkoxy, alkylcarbonyl, alkoxycarbonyl, aminocarbonyl, aryl, heteroaryl, cycloalkyl, and heteroalicyclic.

4. The compound according to claim 3, or a pharmaceutically salt thereof, wherein $R_5$ is hydrogen or

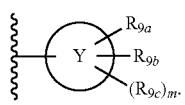

5. The compound according to claim 2, or a pharmaceutically acceptable salt thereof:

Y is pyrrole, furan, thiophene, imidazole, pyrazole, oxazole, isoxazole, thiazole, isothiazole, triazole, thiadiazole, oxadiazole, pyrrolidine, piperidine, azepane, tetrahydrofuran, oxane, or oxepane.

6. The compound according to claim 5, or a pharmaceutically acceptable salt thereof, wherein Y is pyrrole, furan, thiophene, imidazole, pyrazole, oxazole, isoxazole, thiazole, isothiazole, triazole, thiadiazole, or oxadiazole.

7. The compound according to claim 6, or a pharmaceutically acceptable salt thereof, wherein Y is furan, thiophene, imidazole, pyrazole, oxazole, thiazole, triazole, thiadiazole, or oxadiazole.

8. The compound according to claim 5, or a pharmaceutically acceptable salt thereof, wherein Y is piperidine.

9. The compound according to claim 2, or a pharmaceutically acceptable salt thereof, wherein:

$R_{9a}$ is piperidinyl, pyranyl, phenyl, thiophenyl, or pyridyl, wherein said pheny and pyridyl are optionally substituted with hydroxy, amino, nitro, cyano, alkyl, alkoxyl, trifluoromethyl, or halogen.

10. The compound according to claim 2, or a pharmaceutically acceptable salt thereof, wherein:

$R_{9b}$ and $R_{9c}$ are each independently hydrogen, methyl, ethyl, halogen, cyano, amino, nitro, hydroxy, or trifluoromethyl.

11. The compound according to claim 10, or a pharmaceutically acceptable salt thereof, wherein $R_{9b}$ is hydrogen, methyl, ethyl, halogen, cyano, amino, nitro, hydroxy, or trifluoromethyl.

12. The compound according to claim 2, or a pharmaceutically acceptable salt thereof, wherein:

m is 0.

13. A compound of formula 1:

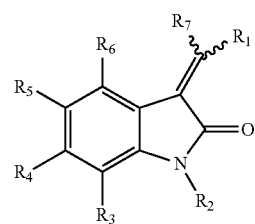

(1)

or a pharmaceutically acceptable salt thereof, wherein:

$R_1$ is optionally substituted heteroaryl, or optionally substituted heteroalicyclic;

$R_2$ is hydrogen, optionally substituted alkyl, optionally substituted alkylcarbonyl, optionally substituted alkoxycarbonyl, or optionally substituted aminocarbonyl;

$R_3$ and $R_4$ are each independently hydrogen, halogen, cyano, nitro, hydroxy, optionally substituted alkyl, optionally substituted alkoxy, optionally substituted amino, optionally substituted alkoxycarbonyl, optionally substituted alkylcarbonyl, optionally substituted aminocarbonyl, or

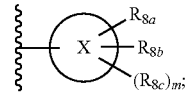

$R_5$ is

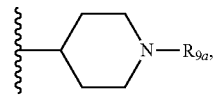

$R_6$ is hydrogen, halogen, cyano, nitro, hydroxy, amino, optionally substituted alkyl, optionally substituted alkoxy, optionally substituted amino, optionally substituted alkoxycarbonyl, optionally substituted alkyl carbonyl, or optionally substituted aminocarbonyl; and $R_7$ is hydrogen, optionally substituted alkyl, or optionally substituted cycloalkyl, wherein:

at least one of $R_3$, $R_4$ and $R_5$ is

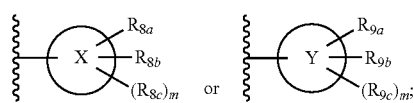

X is optionally substituted five membered heteroaryl or optionally substituted heteroalicyclic;

Y is optionally substituted five membered heteroaryl, provided that the five membered heteroaryl is not

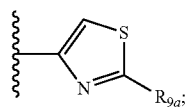

$R_{8a}$ is optionally substituted aryl, optionally substituted heteroaryl, or optionally substituted heteroalicyclic;

$R_{8b}$ and $R_{8c}$ are each independently hydrogen, alkyl, halogen, cyano, amino, nitro, hydroxy, trifluoromethyl, optionally substituted aryl, optionally substituted heteroaryl, or optionally substituted heteroalicyclic;

$R_{9a}$ is 4-piperazinyl (said piperidinyl is substituted with alkyl or alkylcarbonyl), 4-tetrahydropyranyl, phenyl, pyrazinyl, pyrimidinyl, pyridazinyl, or pyridiyl (said phenyl, pyrazinyl, pyrimidinyl, pyridazinyl, or pyridyl is optionally substituted with halogen, hydroxy, cyano, amino, nitro, alkyl, alkoxy, alkoxycarbonyl, alkylcarbonyl, or aminocarbonyl);

$R_{9b}$ and $R_{9c}$ are each independently hydrogen, alkyl, halogen, cyano, amino, nitro, hydroxy, or trifluoromethyl;

m is an integer from 0 to 2; and n is an integer from 0 to 2.

14. The compound according to claim 13, or a pharmaceutically acceptable salt thereof, wherein:

$R_3$ is

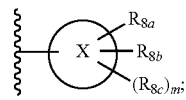

$R_4$ is hydrogen; and $R_5$ is hydrogen.

15. The compound according to claim 13, or a pharmaceutically acceptable salt thereof, wherein:

$R_3$ is hydrogen;

$R_4$ is

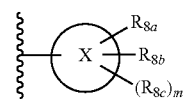

and;

$R_5$ is hydrogen.

16. The compound according to claim 13, or a pharmaceutically acceptable salt thereof, wherein:

$R_3$ is hydrogen;

$R_4$ is hydrogen; and $R_5$ is

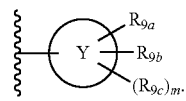

17. A compound selected from the group consisting of:

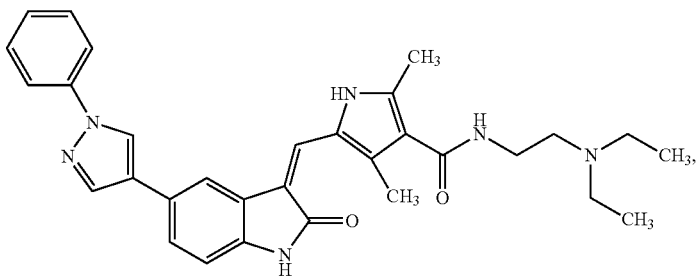

-continued
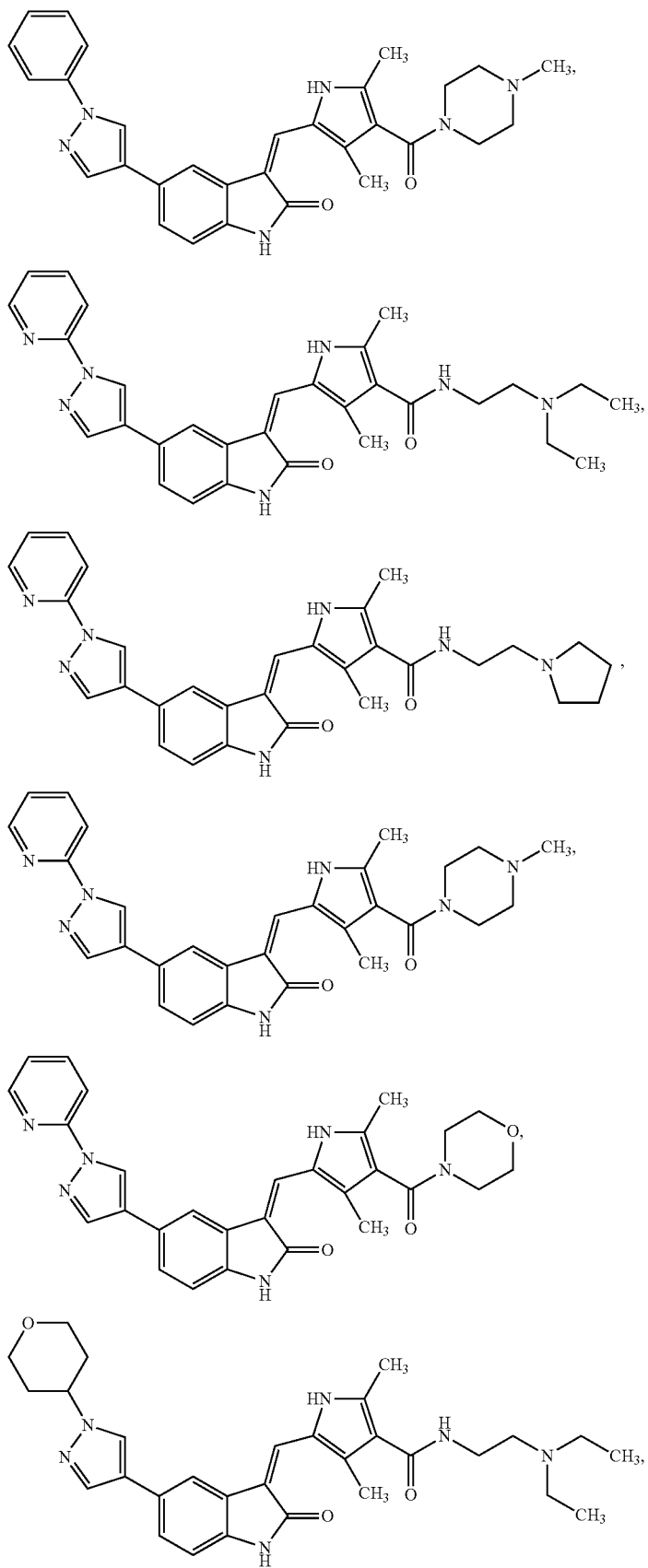

-continued
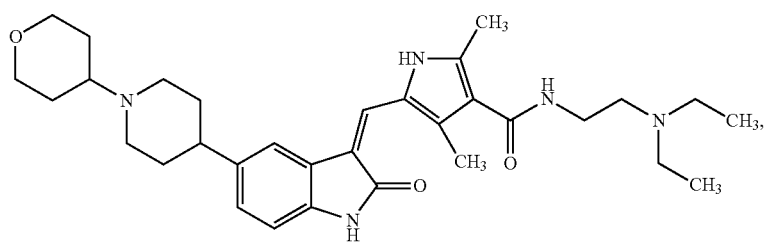
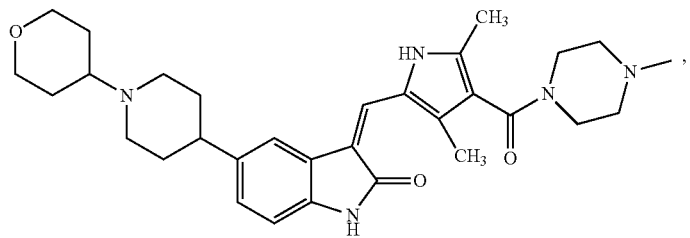
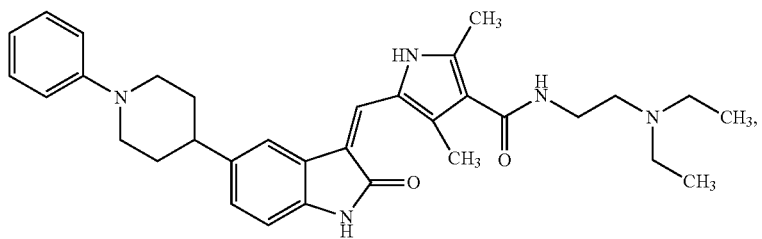
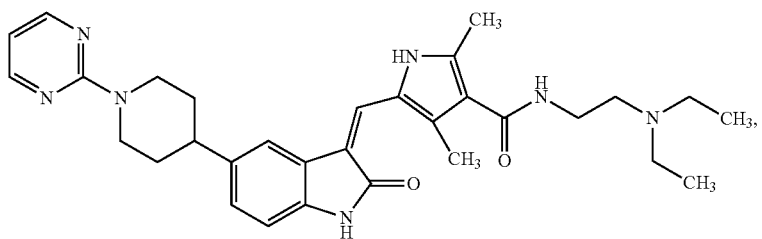
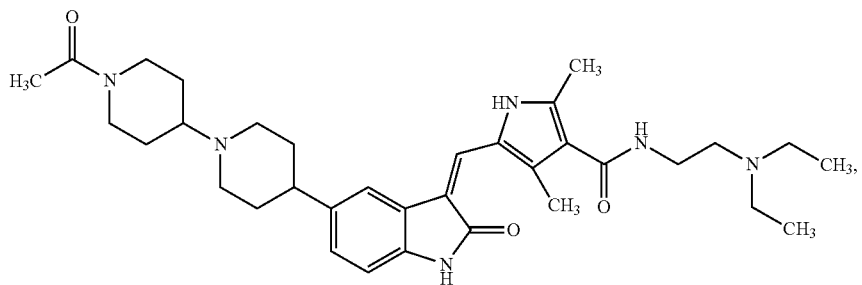
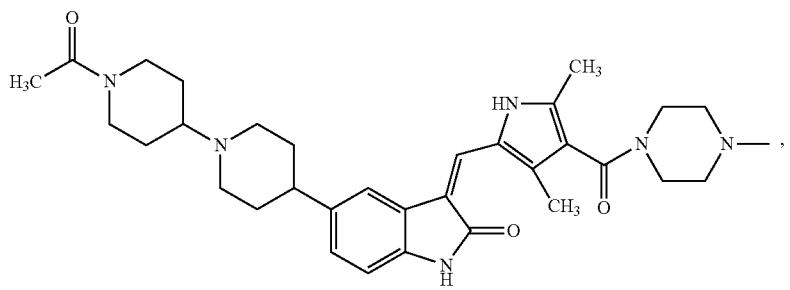

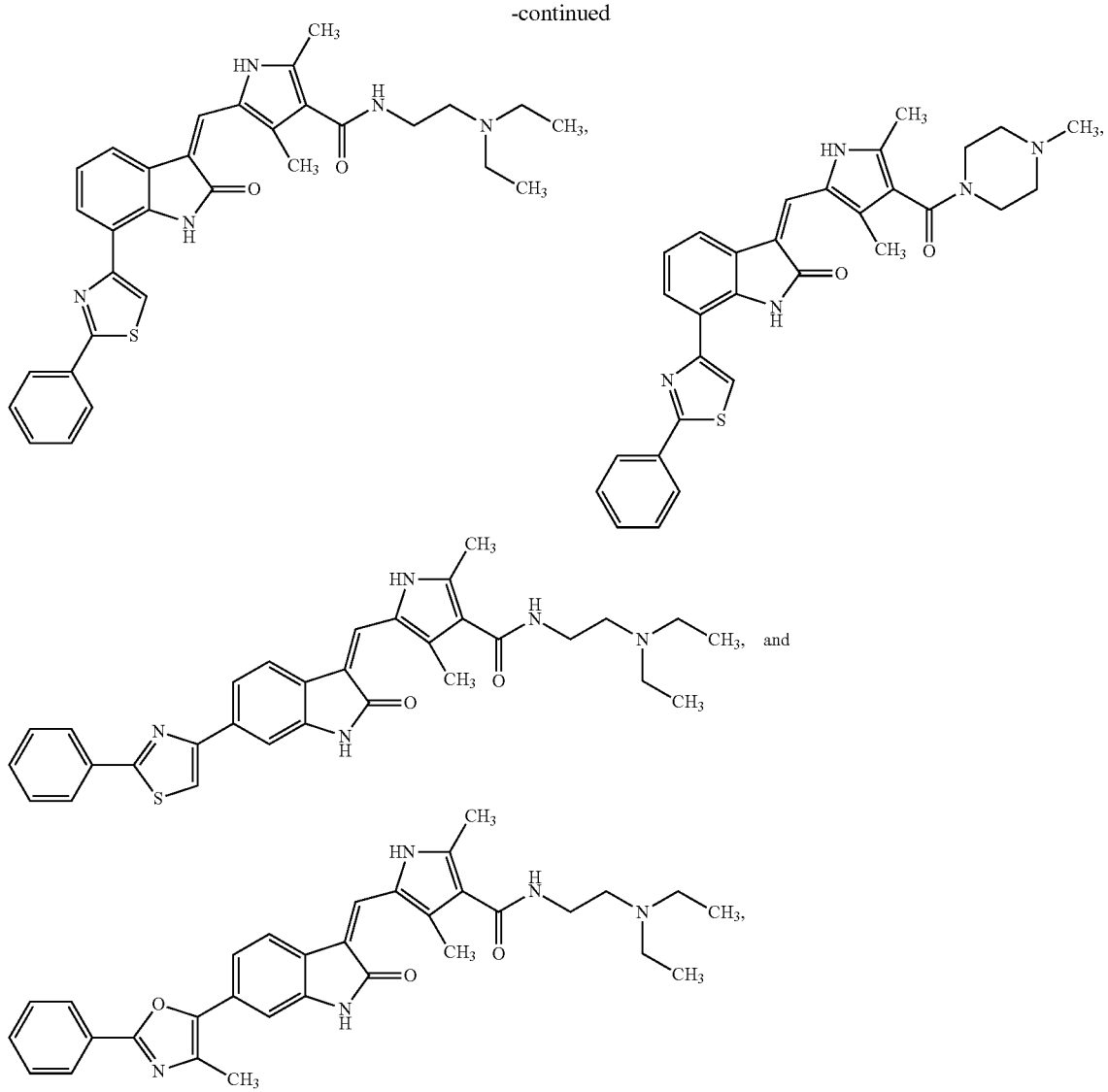
or a pharmaceutically acceptable salt thereof.
18. A pharmaceutical composition comprising the compound of any one of claims 1, 2, 3-12, 13, and 14-17, or a pharmaceutically acceptable salt thereof.
* * * * *